United States Patent [19]

Inai et al.

[11] Patent Number: 5,496,844
[45] Date of Patent: Mar. 5, 1996

[54] INDOLE DERIVATIVES

[75] Inventors: Masatoshi Inai; Tadanao Shibutani; Jun Kanaya, all of Itano; Masako Moritake, Tokushima; Akie Tanaka, Naruto, all of Japan

[73] Assignee: Otsuka Pharmaceutical Factory, Inc., Tokushima, Japan

[21] Appl. No.: 335,833

[22] PCT Filed: Apr. 28, 1993

[86] PCT No.: PCT/JP93/00560

§ 371 Date: Nov. 8, 1994

§ 102(e) Date: Nov. 8, 1994

[87] PCT Pub. No.: WO93/23374

PCT Pub. Date: Nov. 25, 1993

[30] Foreign Application Priority Data

May 8, 1992 [JP] Japan .................. 4-116126

[51] Int. Cl.$^6$ .................. A61K 31/40; C07D 209/04
[52] U.S. Cl. .................. 514/415; 514/414; 514/419; 514/235.2; 514/323; 514/339; 514/365; 514/383; 514/384; 514/397; 548/465; 548/469; 548/494; 548/509; 548/181; 548/266.4; 548/312.1; 546/201; 546/273; 544/143; 544/144
[58] Field of Search .................. 548/465, 469, 548/494, 509, 312.1, 266.4, 181; 514/397, 383, 384, 365, 235.2, 323, 339, 414, 415, 419; 544/143, 144; 546/201, 273

[56] References Cited

U.S. PATENT DOCUMENTS 3,564,009  2/1971  Yamamoto et al. .............. 260/326.16
4,543,360  9/1985  von Angerer et al. .............. 514/415
4,661,511  4/1987  von Angerer et al. .............. 514/415
4,943,572  7/1990  van Angerer .............. 514/235.2
5,023,254  6/1991  von Angerer .............. 514/235.5

OTHER PUBLICATIONS

*J. Med. Chem.*, 27, p. 1439 (1984), von Angerer et al., 2 Phenylindoles . . . , in the Rat.

*Chemical Abstracts*, vol. 99 (1983), Studies . . . aromatic amines., Tao et al., p. 570.

Primary Examiner—Joseph K. McKane
Attorney, Agent, or Firm—Sughrue, Mion, Zinn, Macpeak & Seas

[57] ABSTRACT

The present invention provides indole derivatives of the general formula:

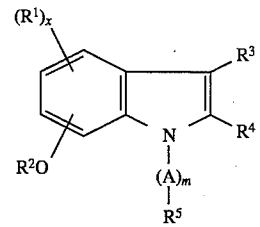

The indole derivatives of the invention have potent antiestrogen activity and are useful as drugs for the treatment of estrogen-dependent diseases, such as anovulatory infertility, prostatic hypertrophy, osteoporosis, breast cancer, endometrial cancer and melanoma.

8 Claims, No Drawings

INDOLE DERIVATIVES

This application is a 371 of pcT/SP93/0056 filed Apr. 28, 1993.

TECHNICAL FIELD

The present invention relates to novel indole derivatives.

PRIOR ART

The indole derivatives of the invention are novel compounds not yet described in the literature.

DISCLOSURE OF INVENTION

It is an object of the invention to provide compounds useful as drugs, as mentioned later herein.

According to the invention, indole derivatives of the general formula (1) shown below are provided.

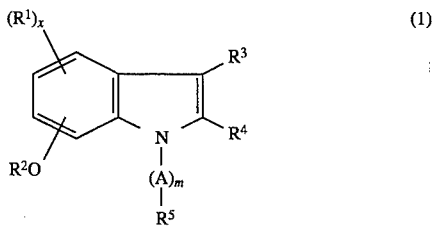

In the above formula, $R^1$ is a halogen atom, $R^2$ is a hydrogen atom, a lower alkyl group, a lower alkanoyl group or a benzoyl group, $R^3$ is a hydrogen atom, a lower alkyl group or a halogen atom, $R^4$ is a thienyl group or a group of the formula

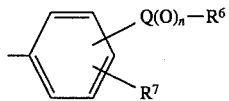

(in which $R^6$ is a lower alkyl group, a cycloalkyl group, a phenyl group which may optionally have a lower alkyl group as a substituent, a phenyl-lower alkyl group or a pyridyl group, $R^7$ is a hydrogen atom or a lower alkyl group, Q is a sulfur or selenium atom and n is an integer of 0 to 2), A is an alkylene group, m is an integer of 0 to 1, $R^5$ is a hydrogen atom, an alkyl group or a benzoyl group having a hydroxyl group or a group of the formula —O—B—$R^8$ (in which B is a lower alkylene group and $R^8$ is a phenyl, di-lower alkyl-amino, 1-pyrrolidinyl, piperidino, 1-imidazolyl or 1,2,4-triazol-1-yl group) as a substituent when m is 0 or, when m is 1, $R^5$ is a lower alkoxycarbonyl group, a carboxyl group, a hydroxyl group, a group of the formula —C(=O)—N($R^9$)—$R^{10}$ (in which $R^9$ and $R^{10}$ are the same or different and each is a hydrogen atom, a lower alkyl group, a cycloalkyl group which may optionally have a benzene ring condensed thereto, a phenyl group, a phenyl-lower alkyl group or a lower alkylsulfonyl group or $R^9$ and $R^{10}$ are bound to each other either directly or via an oxygen or sulfur atom to form, together with the adjacent nitrogen atom, a heterocyclic group which may optionally be substituted with a lower alkoxycarbonyl or carboxyl group), a group of the formula —$CH_2$—N($R^{11}$)—$R^{12}$ (in which $R^{11}$ and $R^{12}$ are the same or different and each is a hydrogen atom, a lower alkyl group, a cycloalkyl group which may optionally have a benzene ring condensed thereto, a phenyl group, a phenyl-lower alkyl group or a lower alkanoyl group or $R^{11}$ and $R^{12}$ are bound to each other either directly or via an oxygen or sulfur atom to form, together with the adjacent nitrogen atom, a heterocyclic group which may optionally be substituted with a lower alkoxycarbonyl or carboxyl group), a group of the formula —$OR^{13}$ (in which $R^{13}$ is a lower alkylcarbamoylphenyl group, a lower alkylaminomethylphenyl group, a lower alkylaminomethylphenyl group, a 1-pyrrolidinylcarbonylphenyl group, a 1-pyrrolidinylmethylphenyl group, a 2-di-lower alkylaminoethyl group or a 2-hydroxyl-2-lower alkylaminoethyl group) or a phenyl group which may optionally have a hydroxyl, lower alkoxy, 1-pyrrolidinylcarbonyl or 1-pyrrolidinylmethyl group as a substituent, and x is an integer of 0 to 2.

As the groups appearing in the above general formula (1), there may be mentioned the following examples. The lower alkyl group includes straight or branched lower alkyl groups such as methyl, ethyl, propyl, isopropyl, butyl, isobutyl, tert-butyl, pentyl and hexyl. The alkyl group includes heptyl, octyl, nonyl, decyl and the like in addition to the lower alkyl groups mentioned above. The lower alkanoyl group includes, among others, acetyl, propionyl, butyryl, valeryl, pivaloyl, hexanoyl and heptanoyl.

As the cycloalkyl group, there may be mentioned cyclopropyl, cyclobutyl, cyclopentyl, cyclohexyl, cycloheptyl, cyclooctyl, etc.

Thus, the cycloalkyl group which may optionally have a benzene ring condensed thereto includes, in addition to the cycloalkyl groups mentioned above, 1-indanyl, 2-indanyl, 1,2,3,4-tetrahydronaphthalen-1-yl, 1,2,3,4-tetrahydronaphthalen-2-yl, etc.

The phenyl-lower alkyl group is, for example, benzyl, 2-phenylethyl, 1-phenylethyl, 3-phenylpropyl, 4-phenylbutyl, 5-phenylpentyl or 6-phenylhexyl.

The lower alkoxy group is, for example, methoxy, ethoxy, propoxy, isopropoxy, butoxy, pentyloxy or hexyloxy.

The phenyl group which may optionally have a lower alkyl group as a substituent includes, in addition to phenyl, 4-methylphenyl, 3-methylphenyl, 2-methylphenyl, 2,4-dimethylphenyl, 3,4-dimethylphenyl, 3,4,5-trimethylphenyl, 4-ethylphenyl, 4-propylphenyl, 4-butylphenyl, 4-pentylphenyl, 4-hexylphenyl, 4-isopropylphenyl and the like.

The pyridyl group includes 2-pyridyl, 3-pyridyl and 4-pyridyl, and the thienyl group includes 2-thienyl and 3-thienyl.

The lower alkoxycarbonyl group is, for example, methoxycarbonyl, ethoxycarbonyl, propoxycarbonyl, butoxycarbonyl, pentyloxycarbonyl or hexyloxycarbonyl.

The lower alkylsulfonyl group is, for example, methylsulfonyl, ethylsulfonyl, propylsulfonyl, butylsulfonyl, pentylsulfonyl or hexylsulfonyl.

The lower alkylene group is, for example, methylene, ethylene, trimethylene, tetramethylene, pentamethylene or hexamethylene, and the alkylene group includes, in addition to these lower alkylene groups, heptamethylene, octamethylene, nonamethylene, decamethylene, undecamethylene, etc.

The halogen atom includes a fluorine atom, a chlorine atom, a bromine atom and an iodine atom.

The di-lower alkylamino group is, for example, dimethylamino, diethylamino, dipropylamino, dibutylamino, dipentylamino or dihexylamino.

The lower alkylcarbamoylphenyl group is, for example, 4-methylcarbamoylphenyl, 4-ethylcarbamoylphenyl, 4-propylcarbamoylphenyl, 4-isopropylcarbamoyl phenyl, 4-butylcarbamoylphenyl, 4-pentylcarbamoylphenyl or 4-hexylcarbamoylphenyl.

The 1-pyrrolidinylcarbonylphenyl group includes 2-(1-pyrrolidinylcarbonyl)phenyl, 3-(1-pyrrolidinylcarbonyl)phenyl and 4-(1-pyrrolidinylcarbonyl)phenyl.

The 1-pyrrolidinylmethylphenyl group includes 2-(1-pyrrolidinylmethyl)phenyl, 3-(1-pyrrolidinylmethyl)phenyl and 4-(1-pyrrolidinylmethyl)phenyl.

The 2-di-lower alkylaminoethyl group is, for example, 2-dimethylaminoethyl, 2-diethylaminoethyl, 2-dipropylaminoethyl, 2-dibutylaminoethyl, 2-dipentylaminoethyl or 2-dihexylaminoethyl.

The 2-hydroxy-2-lower alkylaminoethyl group is, for example 2-hydroxy-2-methylaminoethyl, 2-hydroxy-2-ethylaminoethyl, 2-hydroxy-2-propylaminoethyl, 2-hydroxy-2-isopropylaminoethyl, 2-hydroxy-2-butylaminoethyl, 2-hydroxy-2-pentylaminoethyl or 2-hydroxy-2-hexylaminoethyl.

As the benzoyl group having a hydroxyl group or a group of the formula —O—B—$R^8$ as a substituent, there may be mentioned 4-hydroxybenzoyl, 3-hydroxybenzoyl, 2-hydroxybenzoyl, 4-benzyloxybenzoyl, 4-(2-phenylethoxy)benzoyl, 4-(3-phenylpropoxy)benzoyl, 4-dimethylaminomethoxybenzoyl, 4-(2-dimethylaminoethoxy)benzoyl, 4-(3-dimethylaminopropoxy)benzoyl, 4-(2-diethylaminoethoxy)benzoyl, 4-(1-pyrrolidinylmethoxy)benzoyl, 4-[2-(1-pyrrolidinyl)ethoxy]benzoyl, 4-[3-(1-pyrrolidinyl)propoxy]benzoyl, 4-piperidinomethoxybenzoyl, 4-(2-piperidinoethoxy)benzoyl, 4-(3-piperidinopropoxy)benzoyl, 4-(1-imidazolylmethoxy)benzoyl, 4-[2-(1-imidazolyl)ethoxy]benzoyl, 4-[3-(1-imidazolyl)propoxy]benzoyl, 4-(1,2,4-triazol-1-ylmethoxy)benzoyl, 4-[2-(1,2,4-triazol-1-yl)ethoxy]benzoyl and 4-[3-(1,2,4-triazol-1-yl)propoxy]benzoyl, among others.

As the heterocyclic group which $R^9$ and $R^{10}$, or $R^{11}$ and $R^{12}$, may form together with the adjacent nitrogen atom, there may be mentioned 1-pyrrolidinyl, piperidino, 4-morpholino, 3-thiazolidinyl, etc.

As the phenyl group which may optionally have a hydroxyl, lower alkoxy, 1-pyrrolidinylcarbonyl or 1-pyrrolidinylmethyl group as a substituent, there may be mentioned, for instance, 4-hydroxyphenyl, 3-hydroxyphenyl, 2-hydroxyphenyl, 4-methoxyphenyl, 3-methoxyphenyl, 2-methoxyphenyl, 4-ethoxyphenyl, 4-propoxyphenyl, 4-butoxyphenyl, 4-pentyloxyphenyl, 4-hexyloxyphenyl, 4-(1-pyrrolidinylcarbonyl)phenyl and 4-(1-pyrrolidinylmethyl)phenyl.

The lower alkylaminomethylphenyl group is, for example, methylaminomethylphenyl, ethylaminomethylphenyl, propylaminomethylphenyl, butylaminomethyl phenyl, pentylaminomethylphenyl or hexylaminomethylphenyl.

The indole derivatives of the invention, which are represented by the above general formula (1), have potent antiestrogen activity and are useful as drugs for the treatment of estrogen-dependent diseases such as anovulatory infertility, prostatic hypertrophy, osteoporosis, breast cancer, endometrial cancer and melanoma. The indole derivatives of the invention do not produce those adverse effects that are observed with conventional steroid preparations and the like. Therefore, said indole derivatives are useful as safe drugs.

The indole derivatives of the invention can be produced by a variety of methods, typical examples of which are shown below in terms of reaction formula.

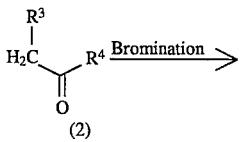

(2)

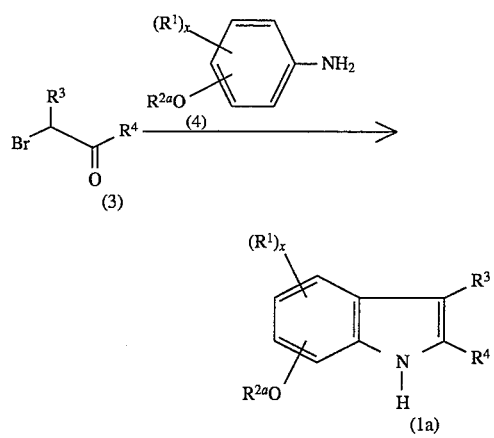

In the above formula, $R^{2a}$ is a lower alkyl group, a lower alkanoyl group or a benzoyl group and $R^1$, $R^3$, $R^4$ and x are defined above For the bromination of compound (2) as shown above in Reaction Formula 1, the compound (2) is reacted with 1 to 1.1 equivalents, relative to compound (2), of bromine in an inert solvent, such as dichloromethane, 1,2-dichloroethane, chloroform or carbon tetrachloride, in the presence of a catalytic amount of a Lewis acid. As said Lewis acid, there may be mentioned anhydrous aluminum chloride, tin tetrachloride, ferric chloride and the like. Among them, anhydrous aluminum chloride is preferred. The reaction is carried out at a temperature of 0° C. to 50° C. for 30 minutes to 5 hours.

Then, the thus-obtained compound (3) is reacted with the aniline derivative (4), whereby the compound (1a) of the invention can be obtained. The reaction is carried out at a temperature of 150° C. to 180° C. for 1 to 3 hours, using, as a solvent, a tertiary amine such as N,N-dimethylaniline, pyridine, collidine or lutidine and using 2 to 5 moles of aniline derivative (4) per mole of compound (3).

[Reaction Formula 2]

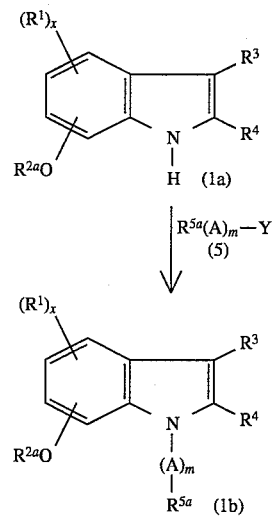

In the above formula, $R^1$, $R^{2a}$, $R^3$, $R^4$, A, m and x are as defined above, $R^{5a}$ is an alkyl group or a benzoyl group having a group of the formula —O—B—$R^8$ ($R^8$ and B being as defined above) when m is 0 or, when m is 1, $R^{5a}$ is a lower alkoxycarbonyl group, a group of the formula —C(═O)—

$N(R^{9a})$—$R^{10a}$ (in which $R^{9a}$ and $R^{10a}$ are the same or different and each is a hydrogen atom, a lower alkyl group, a cycloalkyl group which may have a benzene ring condensed thereto, a phenyl group, a phenyl-lower alkyl group or a lower alkylsulfonyl group or $R^{9a}$ and $R^{10a}$ are bound to each other either directly or via an oxygen or sulfur atom to form, together with the adjacent nitrogen atom, a heterocyclic group which may optionally be substituted with a lower alkoxycarbonyl group), a group of the formula —$OR^{13a}$ (in which $R^{13a}$ is a lower alkyl carbamoylphenyl or 1-pyrrolidinylcarbonylphenyl group) or a phenyl group which may optionally have a lower alkoxy group or a 1-pyrrolidinylcarbonyl group as a substituent, and Y is a halogen atom.

The compound (1b) can be derived by reacting the compound (1a) with the compound (5), as shown above in Reaction Formula 2. The reaction can be carried out in an aprotic inert solvent, such as N,N-dimethylformamide (DMF) or N,N-dimethylacetamide, in the presence of a base, such as sodium hydride, sodium amide or sodium methoxide. Generally, the compound (5) is used preferably in an amount of 1 to 2 moles per mole of compound (1a) and the base in an amount of 1 to 1.5 moles per mole of compound (1a). The reaction is conducted at a temperature of 0° C. to 30° C. for about 1 to 3 hours.

[Reaction Formula 3]

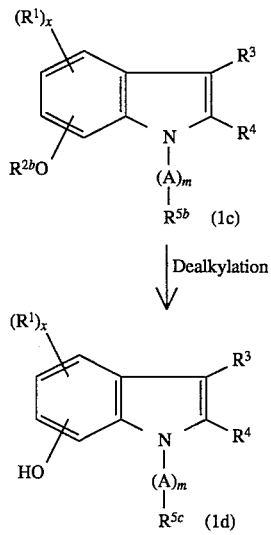

In the above formula, $R^1$, $R^3$, $R^4$, A, m and x are as defined above, $R^{2b}$ is a lower alkyl group, $R^{5b}$ is a hydrogen atom, an alkyl group or a benzoyl group having a benzyloxy group or a group of the formula —O—B—$R^{8a}$ (in which B is as defined above and $R^{8a}$ is a di-lower alkylamino, 1-pyrrolidinyl, piperidino, 1-imidazolyl or 1,2,4-triazol-1-yl group) as a substituent when m is 0 or, when m is 1, $R^{5b}$ is a lower alkoxycarbonyl group, a hydroxyl group, a group of the formula —C(=O)—$N(R^{9a})$—$R^{10a}$ ($R^{9a}$ and $R^{10a}$ being as defined above), a group of the formula —$CH_2$—$N(R^{11a})$—$R^{12a}$ (in which $R^{11a}$ and $R^{12a}$ are the same groups as the $R^{9a}$ and $R^{10a}$ groups mentioned above except that neither of them can be a lower alkylsulfonyl group), a group of the formula —$OR^{13}$ ($R^{13}$ being as defined above) or a phenyl group which may optionally have a lower alkoxy, 1-pyrrolidinylcarbonyl or 1-pyrrolidinylmethyl group as a substituent, and $R^{5C}$ is a hydrogen atom, an alkyl group or a benzoyl group having a hydroxyl group or a group of the formula —O—B—$R^{8a}$ (B and $R^{8a}$ being as defined above) as a substituent when m is 0 or, when m is 1, $R^{5c}$ is a lower alkoxycarbonyl group, a hydroxyl group, a group of the formula —C(=O)—$N(R^{9b})$—$R^{10b}$ (in which $R^{9b}$ and $R^{10b}$ are the same or different and each is a hydrogen atom, a lower alkyl group, a cycloalkyl group which may have a benzene ring condensed thereto, a phenyl group, a phenyl-lower alkyl group or a lower alkylsulfonyl group or $R^{9b}$ and $R^{10b}$ are bound to each other either directly or via an oxygen or sulfur atom to form, together with the adjacent nitrogen atom, a heterocyclic group which may optionally be substituted with a carboxyl group), a group of the formula —$CH_2$—$N(R^{11b})$—$R^{12b}$ (in which $R^{11b}$ and $R^{12b}$ are the same as the $R^{9b}$ and $R^{10b}$ groups mentioned above except that neither of them can be a lower alkylsulfonyl group), a group of the formula —$OR^{13}$ ($R^{13}$ being as defined above) or a phenyl group which may optionally have a hydroxyl, 1-pyrrolidinylcarbonyl or 1-pyrrolidinylmethyl group as a substituent.

The dealkylation of compound (1c) as shown above in Reaction Formula 3 is carried out in an inert solvent, such as dichloromethane or 1,2-dichloroethane, in the presence of a Lewis acid. Said Lewis acid is, for example, boron tribromide, anhydrous aluminum chloride, anhydrous aluminum bromide or boron trifluoride diethyl ether complex, and is recommendably used in an amount of 1 to 3 mole equivalents relative to compound (1c). In carrying out this reaction, an adequate amount of a thiol, such as ethanethiol, or an iodide salt, such as sodium iodide, may be added to the reaction system, when necessary. The reaction is carried out at a temperature between 0° C. and the boiling point of the solvent, preferably at room temperature, for about 0.5 to 5 hours, whereby the compound (1d) of the invention can be obtained.

When the compound (1c) has a halogen atom at each of the 3 and 6 positions and an $R^{2c}O$— group at the 5 position, dealkylation of said compound using anhydrous aluminum chloride in the presence of a thiol can give a compound resulting from the dealkylation and simultaneous dehalogenation, namely substitution of the halogen atoms at positions 3 and 6 each with a hydrogen atom.

[Reaction Formula 4]

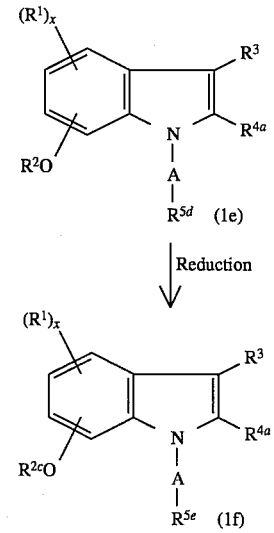

In the above formula, $R^1$, $R^3$, $R^4$, A and x are as defined above, $R^{2c}$ is a hydrogen atom or a lower alkyl group, $R^{4a}$ is a thienyl group or a group of the formula

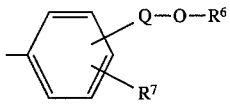

($R^6$, $R^7$ and Q being as defined above), $R^{5d}$ is a group of the formula —C(=O)—N($R^9c$)—$R^{10c}$ (in which $R^{9c}$ and $R^{10c}$ are the same or different and each is a hydrogen atom, a lower alkyl group, a cycloalkyl group which may have a benzene ring condensed thereto, a phenyl group or a phenyl-lower alkyl group or $R^{9c}$ and $R^{10c}$ are bound to each other either directly or via an oxygen or sulfur atom to form, together with the adjacent nitrogen atom, a heterocyclic group), a group of the formula —$OR^{13a}$ ($R^{13a}$ being as defined above) or a phenyl group having a 1-pyrrolidinyl-carbonyl group as a substituent, and $R^{5e}$ is a group of the formula —$CH_2$—N($R^{11c}$)—$R^{12c}$ (in which $R^{11c}$ and $R^{12c}$ are the same as the $R^{9c}$ and $R^{10c}$ groups mentioned above), a group of the formula —$OR^{13b}$ (in which $R^{13b}$ is a lower alkylaminomethylphenyl group or a 1-pyrrolidinylmethylphenyl group) or a phenyl group having a 1-pyrrolidinylmethyl group as a substituent.

As shown above in Reaction Formula 4, the compound (1f) can be produced by reducing the compound (1e).

The reduction is carried out in an inert solvent, such as diethyl ether or tetrahydrofuran (THF), using lithium aluminum hydride, diisobutylaluminum hydride (DIBAL) or the like as the reducing agent. When carried out at a temperature of 0° to 70° C., the reaction will be complete in 1 to 8 hours.

[Reaction Formula 5]

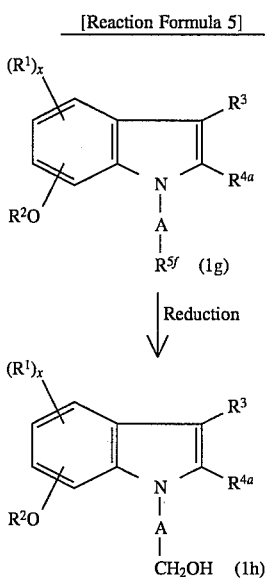

In the above formula $R^1$, $R^2$, $R^3$, $R^{4a}$, A and x are as defined above and $R^{5f}$ is a lower alkoxycarbonyl group or a carboxyl group.

The reduction of compound (1g) as shown above in Reaction Formula 5 can be carried out under substantially the same conditions as that shown by Reaction Formula 4. Thus, the solvent, reducing agent, temperature and time, for instance, can suitably be selected within the respective ranges mentioned above.

[Reaction Formula 6]

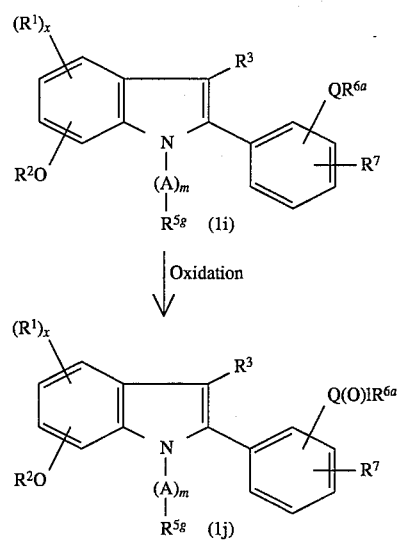

In the above formula, $R^1$, $R^2$, $R^3$, $R^7$, A, Q, m and x are as defined above and $R^{5a}$ is a hydrogen atom, an alkyl group or a benzoyl group having a hydroxyl group or a group of the formula —O—B—$R^8$ (B and $R^8$ being as defined above) as a substituent when m is 0 or, when m is 1, $R^{5a}$ is a lower alkoxycarbonyl group, a carboxyl group, a group of the formula —C(=O)—N($R^9$)—$R^{10}$ ($R^9$ and $R^{10}$ being as defined above), a group of the formula —$CH_2$—N($R^{11}$)—$R^{12}$ ($R^{11}$ and $R^{12}$ being as defined above), a group of the formula —$OR^{13b}$ (in which $R^{13b}$ is a lower alkylcarbamoylphenyl, lower alkylaminomethylphenyl, 1-pyrrolidinylcarbonylphenyl, 1-pyrrolidinylmethylphenyl or 2-di-lower alkylaminoethyl group) or a phenyl group which may optionally have a hydroxyl, lower alkoxy, 1-pyrrolidinylcarbonyl or 1-pyrrolidinylmethyl group as a substituent. $R^{6a}$ is a lower alkyl group, a cycloalkyl group, a phenyl group which may optionally have a lower alkyl group as a substituent or a phenyl-lower alkyl group, and l is an integer of 1 or 2.

As shown above in Reaction Formula 6, the compound (1j) can be produced by oxidizing the compound (1i).

The oxidation is carried out in a solvent, such as dichloromethane, 1,2-dichloroethane, chloroform, acetic acid, methanol or water, using, as the oxidizing agent, m-chloroperbenzoic acid, N-chlorosuccinimide, sodium metaperiodate, hydrogen peroxide or the like. The oxidizing agent is generally used in an amount of 1 equivalent to slight excess and, when carried out at a temperature of 0° to 100° C., the reaction will be complete in 1 to 3 hours.

Those compounds of general formula (1j) in which l=2 can be produced by adding a further 1 equivalent or slight excess of the oxidizing agent and conducting the reaction or by oxidizing again the compounds in which l=1 under the same conditions.

[Reaction Formula 7]

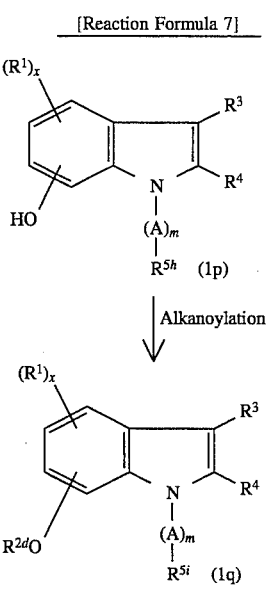

In the above formula, $R^1$, $R^3$, $R^4$, A, m and x are as defined above, $R^{2d}$ is a lower alkanoyl group, $R^{5h}$ is an alkyl group or a benzoyl group having a group of the formula —O—B—$R^8$ (B and $R^8$ being as defined above) as a substituent when m is 0 or, when m is 1, $R^{5h}$ is a lower alkoxycarbonyl group, a group of the formula —C(=O)—N($R^{9a}$)—$R^{10a}$ ($R^{9a}$ and $R^{10a}$ being as defined above ), a group of the formula —CH$_2$—N($R^{11a}$)—$R^{12a}$ ($R^{11a}$ and $R^{12a}$ being as defined above), a group of the formula —O$R^{13c}$ (in which $R^{13c}$ is a lower alkylcarbamoylphenyl group, a 1-pyrrolidinylcarbonylphenyl group, a 1-pyrrolidinylmethylphenyl group or a 2-di-lower alkylaminoethyl group) or a phenyl group which may optionally have a lower alkoxy, 1-pyrrolidinylcarbonyl or 1-pyrrolidinylmethyl group as a substituent, and $R^{5i}$ is an alkyl group or a benzoyl group having a group of the formula —O—B—$R^8$ (B and $R^8$ being as defined above) as a substituent when m is 0 or, when m is 1, $R^{5i}$ is a lower alkoxycarbonyl group, a group of the formula —C(=O)—N($R^{9a}$)—$R^{10a}$ ($R^{9a}$ and $R^{10a}$ being as defined above), a group of the formula —CH$_2$—N($R^{11d}$)—$R^{12d}$ (in which $R^{11d}$ and $R^{12d}$ are the same or different and each is a hydrogen atom, a lower alkyl group, a cycloalkyl group which may optionally have a benzene ring condensed thereto, a phenyl group, a phenyl-lower alkyl group or a lower alkanoyl group or $R^{11d}$ and $R^{12d}$ are bound to each other either directly or via an oxygen or sulfur atom to form, together with the adjacent nitrogen atom, a heterocyclic group which may optionally be substituted with a lower alkoxycarbonyl group), a group of the formula —O$^{R13c}$ ($R^{13c}$ being as defined above) or a phenyl group which may optionally have a lower alkoxy, 1-pyrrolidinylcarbonyl or 1-pyrrolidinylmethyl group as a substituent.

The alkanoylation of compound (1p) as shown above in Reaction Formula 7 can be effected by reacting the starting compound with an acid anhydride in a basic solvent, or in an inert solvent in the presence of a base catalyst. As said basic solvent, use can be made of pyridine, collidine, lutidine and triethylamine, for instance. As said inert solvent, use can be made of THF, diethyl ether, chloroform, dichloroethane, DMF, etc. and, in this case, the basic solvent mentioned above is preferably used as the base catalyst in an amount of about 1 to 3 moles per mole of compound (1p). The acid anhydride is, for example, acetic anhydride, propionic anhydride, butyric anhydride, valeric anhydride, caproic anhydride or heptanoic anhydride. When carried out at room temperature to about 100° C., the reaction will be complete in about 1 to 5 hours, thus giving the objective compound (1g).

[Reaction Formula 8]

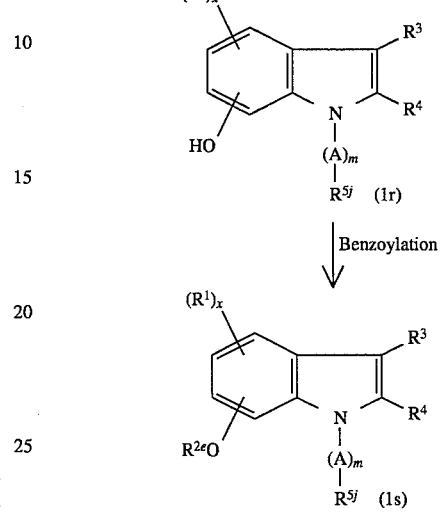

In the above formula, $R^1$, $R^3$, $R^4$, A, m and x are as defined above, $R^{2e}$ is a benzoyl group and $R^{5j}$ is an alkyl group or a benzoyl group having a group of the formula —O—B—$R^8$ (B and $R^8$ being as defined above) as a substituent when m is 0 or, when m is 1, $R^{5j}$ is a lower alkoxycarbonyl group, a group of the formula —C(=O)—N($R^{9d}$)—$R^{10d}$ (in which $R^{9d}$ and $R^{10d}$ are the same or different and each is a lower alkyl group, a cycloalkyl group which may optionally have a benzene ring condensed thereto, a phenyl group, a phenyl-lower alkyl group or a lower alkylsulfonyl group or $R^{9d}$ and $R^{10d}$ are bound to each other either directly or via an oxygen or sulfur atom to form, together with the adjacent nitrogen atom, a heterocyclic group which may optionally be substituted with a lower alkoxycarbonyl group), a group of the formula —CH$_2$—N($R^{11e}$)—$R^{12e}$ (in which $R^{11e}$ and $R^{12e}$ are the same as the $R^{9d}$ and $R^{10d}$ groups mentioned above), a group of the formula —O$R^{13c}$ ($R^{13c}$ being as defined above) or a phenyl group which may optionally have a lower alkoxy, 1-pyrrolidinylcarbonyl or 1-pyrrolidinylmethyl group as a substituent.

The benzoylation of compound (1r) as shown above in Reaction Formula 8 can be effected by reacting the starting compound with a benzoyl halide, such as benzoyl chloride or benzoyl bromide, in a basic solvent, or in an inert solvent in the presence of a base catalyst. The basic solvent and inert solvent can suitably be selected from among those mentioned above for the alkanoylation shown by Reaction Formula 7. When carried out at room temperature to about 100° C., the reaction will be complete in about 0.5 to 3 hours to give the objective compound (1s).

[Reaction Formula 9]

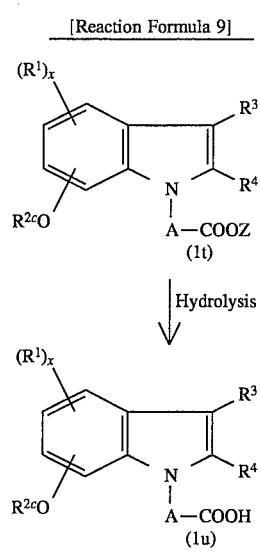

In the above formula, $R^1$, $R^{2c}$, $R^3$, $R^4$, A and x are as defined above, and Z is a lower alkyl group.

As shown above in Reaction Formula 9, the compound (1u) can be produced by hydrolyzing the compound (1t). The reaction is carried out in an inert solvent, such as methanol, ethanol, THF or dioxane, in the presence of an alkali, such as aqueous sodium hydroxide solution, aqueous potassium hydroxide solution or potassium carbonate, at a temperature around the boiling point of the solvent for about 0.5 to 2 hours.

[Reaction Formula 10]

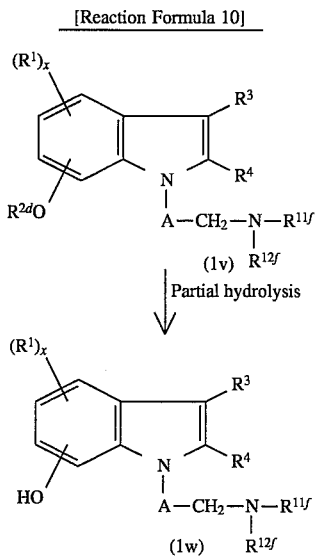

In the above formula, $R^1$, $R^{2d}$, $R^3$, $R^4$, A and x are as defined above, $R^{11f}$ is a lower alkanoyl group and $R^{12f}$ is a hydrogen atom, a lower alkyl group, a cycloalkyl group which may optionally have a benzene ring condensed thereto, a phenyl group, a phenyl-lower alkyl group or a lower alkanoyl group.

The partial hydrolysis of compound (1v) as shown above in Reaction Formula 10 can be effected by treating said compound with an alkali in an inert solvent at a temperature between room temperature and about 70° C. for 0.5 to 2 hours. As the inert solvent and alkali, there can be used the same ones as mentioned above for the hydrolysis reaction shown by Reaction Formula 9.

[Reaction Formula 11]

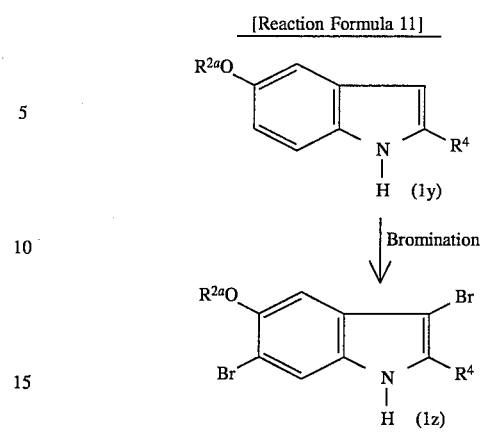

In the above formula, $R^{2a}$ and $R^4$ are as defined above.

The bromination of compound (1y) as shown above in Reaction Formula 11 is carried out in an inert solvent, such as dioxane, dichloromethane or chloroform, in the presence of a tertiary amine, such as pyridine, collidine, lutidine or N,N-dimethylaniline, using a brominating agent, such as bromine. The tertiary amine and brominating agent mentioned above are preferably used each in an amount of about 2 equivalents relative to compound (1y), and the reaction is generally carried out at −10° C. to room temperature for 5 minutes to 1 hour.

[Reaction Formula 12]

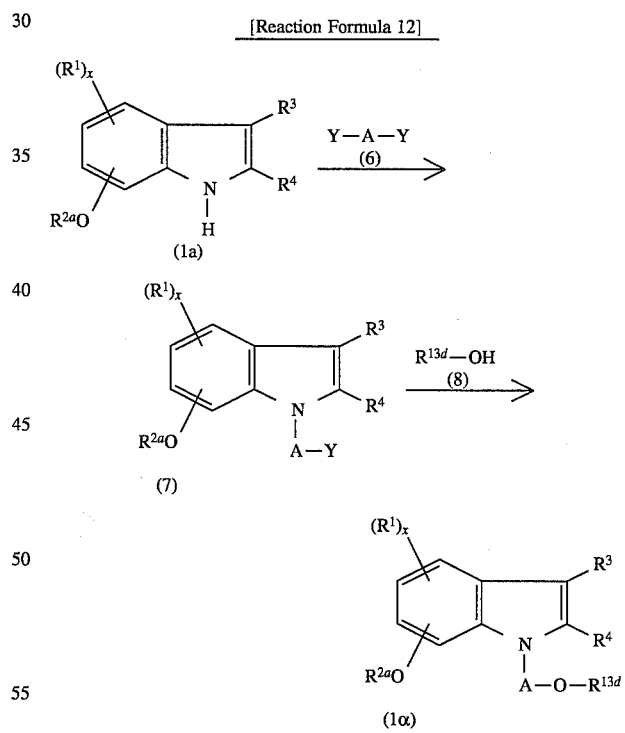

In the above formula, $R^1$, $R^{2a}$, $R^3$, $R^4$, A and x are as defined above, $R^{13d}$ is a di-lower alkylaminoethyl group and Y is a halogen atom.

The reaction between compound (1a) and compound (6) as shown above in Reaction Formula 12 can be carried out in the same manner and under the same conditions as the reaction between compound (1a) and compound (5) as shown by Reaction Formula 2. The compound (7) thus obtained can be converted to the objective compound (1α) by reacting with the compound (8). This reaction, too, can be carried out in the same manner and under the same conditions as the reaction shown by Reaction Formula 2.

[Reaction Formula 13]

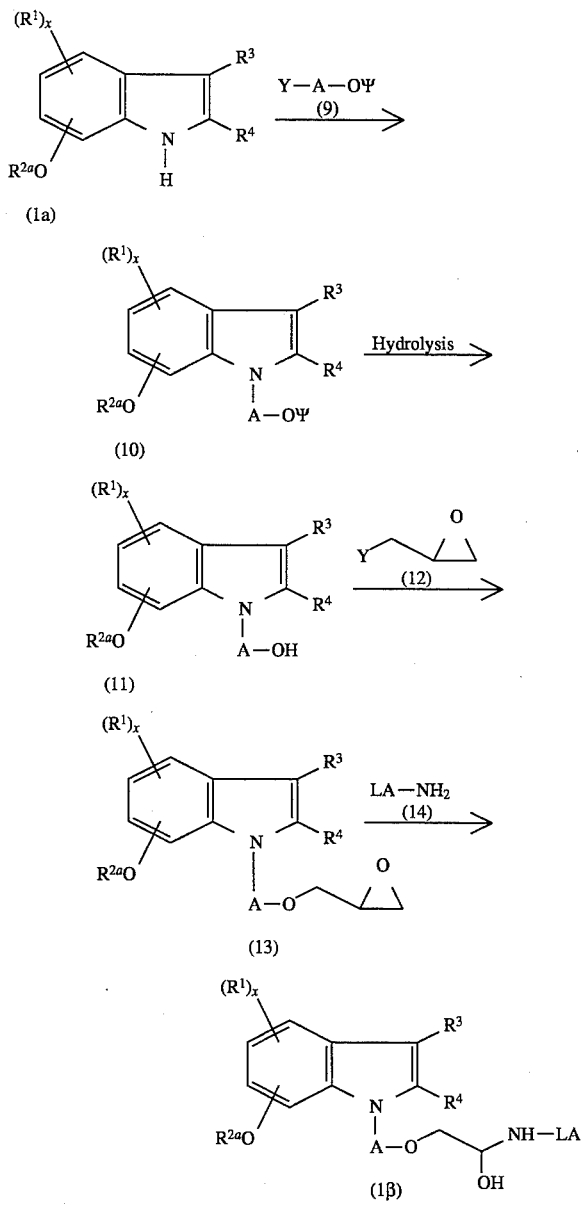

In the above formula $R^1$, $R^{2a}$, $R^3$, $R^4$, A, x and Y are as defined above ψ is a lower alkanoyl group and LA is a lower alkyl group.

The reaction between compound (1a) and compound (9) as shown above in Reaction Formula 13 can be carried out in the same manner and under the same conditions as the reaction between compound (1a) and compound (5) as shown by Reaction Formula 2. The hydrolysis of the thus-obtained compound (10) can be carried out in the same manner and under the same conditions as the hydrolysis shown by Reaction Formula 9. The subsequent reaction between compound (11) and compound (12) can be carried out in the same manner and under the same conditions as the reaction shown by Reaction Formula 2. The objective compound (1β) can be produced by reacting the compound (13) obtained further with the lower alkylamine (14). This reaction can be effected by dissolving the compound (13) in an excess of the lower alkylamine (14) and heating the mixture at around the refluxing temperature for about 20 to 30 hours.

The compound of the invention can thus be produced by the methods mentioned above.

The compounds (2a), (2b), (2c) and (2d) to serve as starting materials for the compounds of the invention can be produced, for example, by the processes shown below in terms of reaction formula.

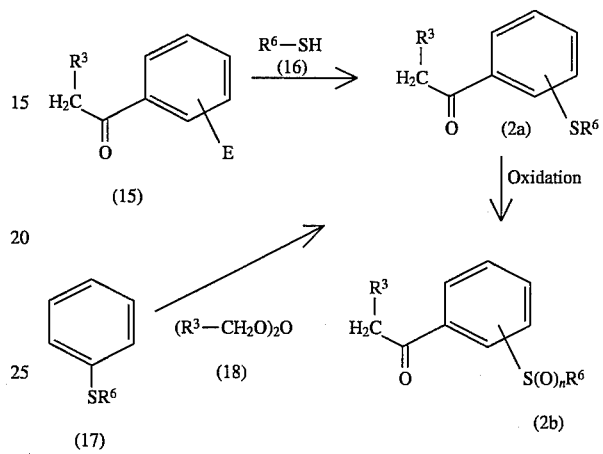

In the above formula, $R^3$, $R^6$ and n are as defined above and E is a halogen atom, a lower alkylsulfonyloxy group or a p-toluenesulfonyl group.

Thus, the compound (2a) can be prepared by reacting the compound (15) with the thiol (16) in the presence of a deacidifying agent or by treating the compound (17) with the acid anhydride (18) in the presence of a Lewis acid.

The solvent to be used in the above reaction between compound (15) and thiol (16) is suitably an aprotic polar solvent such as DMF, N,N-dimethylacetamide, dimethyl sulfoxide (DMSO) or hexamethylphosphoric triamide (HMPA). Suited for use as the deacidifying agent are inorganic salts such as sodium carbonate, potassium carbonate, sodium hydrogen carbonate and potassium hydrogen carbonate and tertiary amines such as triethylamine, pyridine and 1,8-diazabicyclo[5.4.0]-7-undecene (DBU), among others. Said reaction is carried out at 50° to 150° C., preferably around 100° C., for about 3 to 24 hours.

The reaction between compound (17) and acid anhydride (18) is carried out in an inert solvent, such as dichloromethane, chloroform, 1,2-dichloroethane or carbon disulfide, at about 0° to 80° C. for 3 to 24 hours, using, as the Lewis acid, anhydrous aluminum chloride, anhydrous aluminum bromide or the like.

The compound (2a) is then converted to the compound (2b) by oxidation. The oxidation reaction can be carried out in the same manner as that represented by Reaction Formula 6, hence the solvent, oxidizing agent and reaction conditions are to be selected within the respective ranges mentioned above.

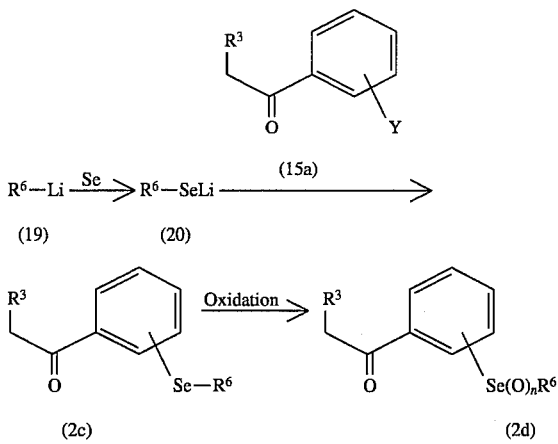

In the above formula, $R^3$, $R^6$, Y and n are as defined above.

As shown above by Reaction Formula 15, the compound (20) can first be produced by stirring the compound (19) with about 1 equivalent of selenium in an inert solvent, such as THF or diethyl ether, at a temperature between about 0° C. and room temperature for about 5 to 30 minutes. A solution of the compound (15a) is then added to the reaction mixture for further oxidation to give the compound (2c). As the solvent for the compound (15a) mentioned above, there may be mentioned, for instance, DMF, DMSO and HMPA and, when carried out at a temperature of about 50° C. to the refluxing temperature, the reaction will be complete in about 1 to 10 hours.

The compound (2c) can be converted to the compound (2d) by carrying out the oxidation in the same manner.

Among the compounds of the invention, which are represented by general formula (1), those compounds having a basic group readily form salts when reacted with pharmaceutically acceptable acids while those compounds having an acidic group readily form salts when reacted with pharmaceutically acceptable basic compounds. Such salts also show the same pharmacological activities as the compounds of the invention and are useful as drugs. The acids mentioned above include inorganic acids such as hydrochloric acid, sulfuric acid, phosphoric acid and hydrobromic acid, and organic acids such as oxalic acid, maleic acid, fumaric acid, malic acid, tartaric acid, citric acid, benzoic acid, acetic acid and p-toluene-sulfonic acid. As said basic compounds, there may be mentioned, among others, metal hydroxides such as sodium hydroxide, potassium hydroxide and calcium hydroxide, and alkali metal carbonates and bicarbonates such as sodium carbonate, sodium hydrogen carbonate and potassium hydrogen carbonate.

Among the compounds of the invention, which are represented by general formula (1), some contain an asymmetric carbon atom or atoms. In particular, for those compounds in which n is 1, there are optical isomers with the sulfur or selenium atom as an asymmetric center. Naturally, the present invention includes these isomers as well.

The objective compounds produced in the respective reaction steps mentioned above can be readily isolated and purified by conventional means. As such means, there may be mentioned, for example, adsorption chromatography, preparative thin layer chromatography, recrystallization, and solvent extraction.

The compounds of the invention are generally put to practical use in the form of conventional pharmaceutical preparations or compositions prepared by using appropriate pharmaceutical carriers. Said pharmaceutical carriers are conventional diluents or excipients, inclusive of fillers, extenders, binders, moistening agents, disintegrators, surfactants and lubricants, depending on the usage form of the pharmaceutical preparation in question. These are suitably selected depending on the unit dosage form of the pharmaceutical preparation in question.

As typical examples of the unit dosage forms for the above-mentioned pharmaceutical preparations containing the compounds of the invention, which can be selected from among various forms depending on the therapeutic purpose, there may be mentioned tablets, pills, powders, solutions, suspensions, emulsions, granules, capsules, suppositories, injections (solutions, suspensions, etc.), and ointments.

In shaping the form of tablets, use can be made, as the pharmaceutical carries mentioned above, of excipients such as lactose, sucrose, sodium chloride, glucose, urea, starch, calcium carbonate, kaolin, crystalline cellulose, silicic acid, potassium phosphate, etc., binders such as water, ethanol, propanol, simple syrup, glucose solution, starch solution, gelatin solution, carboxymethylcellulose, hydroxypropylcellulose, methylcellulose, polyvinylpyrrolidone, etc., disintegrators such as carboxymethylcellulose sodium, carboxymethylcellulose calcium, low substitution degree hydroxypropylcellulose, dried starch, sodium alginate, agar powder, laminaran powder, sodium hydrogen carbonate, calcium carbonate, etc., surfactants such as polyoxyethylenesorbitan fatty acid esters, sodium lauryl sulfate, stearic acid monoglyceride, etc., disintegration inhibitors such as sucrose, stearin, cacao butter, hydrogenated oils, etc., absorption promoters such as quaternary ammonium bases, sodium lauryl sulfate, humectants such as glycerol, starch, etc., adsorbents such as starch, lactose, kaolin, bentonite, colloidal silicic acid, etc., and lubricants such as purified talc, stearic acid salts, boric acid powder, polyethylene glycol, etc. can be used, among others. When necessary, the tablets may be provided with a conventional coating to give sugar-coated tablets, gelatin-coated tablets, enteric coated tablets, film-coated tablets or, further, double-layer or multilayer tablets.

In shaping the form of pills, the pharmaceutical carriers that can be used are, for instance, excipients such as glucose, lactose, starch, cacao butter, hardened vegetable oils, kaolin, talc, etc., binders such as gum arabic powder, tragacanth powder, gelatin, ethanol, etc., and disintegrators such as laminaran, agar, etc. among others.

In shaping the form of suppositories, the pharmaceutical carriers that can be used are, for example, polyethylene glycol, cacao butter, higher alcohols, higher alcohol esters, gelatin, semisynthetic glycerides, etc.

Capsules are prepared in the conventional manner generally by admixing an active ingredient compound of the invention with various pharmaceutical carriers such as mentioned above and then filling the mixture into hard gelatin capsules, soft gelatin capsules, etc.

In cases where the medicinal compounds of the invention are made up into injections such as solutions, emulsions or suspensions, the injections are sterilized and are preferably isotonic with blood and, in making up into such forms, water, ethyl alcohol, macrogol, propylene glycol, ethoxylated isostearyl alcohol, polyoxylated isostearyl alcohol, polyoxyethylenesorbitan fatty acid esters and the like can be used as the diluents. In this case, sodium chloride, glucose or glycerol may be added, in an amount sufficient to prepare isotonic solutions, to the pharmaceutical preparations of the invention. Conventional solubilizing agents, buffers, anesthetics or the like may also be added.

The pharmaceutical preparations of the invention may further contain colorants, preservatives, perfumes, flavors, sweeteners and the like and, further, other drugs.

The proportion of the active ingredient compound of general formula (1) to be contained in the pharmaceutical preparations of the invention is not critical but may be selected within a wide range. It is generally preferable that the pharmaceutical preparations contain the active ingredient compound in a proportion of about 1 to 70% by weight.

The method of administration of the pharmaceutical preparations mentioned above is not critical but can suitably be selected depending on each dosage form, patient's age, sex and other conditions, severity of disease and other factors. Thus, for instance, tablets, pills, solutions, suspensions, emulsions, granules and capsules are administered orally, injections are administered intravenously either singly or in admixture with a conventional nutrient solution containing glucose, amino acids, etc., or, when necessary, singly administered intramuscularly, intradermally, subcutaneously or intraperitoneally, and suppositories are administered intrarectally.

The dose of the pharmaceutical preparations mentioned above is suitably selected depending on such factors as usage, patient's age, sex and other conditions, and severity of disease. Generally, however, the dose is recommendably about 0.5 to 20 mg as the active ingredient compound of the invention per kilogram of body weight per day, and said preparations can be administered in 1 to 4 divided doses daily.

BEST MODES FOR CARRYING OUT THE INVENTION

For illustrating the present invention in further detail, reference examples, which are concerned with the production of starting materials for the compounds of the invention, and example, which are concerned with the production of the compounds of the invention, are shown below. Furthermore, certain examples of the production of pharmaceutical preparations using the compounds of the invention and a pharmacological test example for the compounds of the invention are given.

Reference Example 1

Production of 2-bromo-4'-phenylthioacetophenone

Thiophenol (184 g) was gradually added dropwise to a suspension of 196 g of anhydrous potassium carbonate in 1,000 ml of DMF at room temperature, followed by dropwise addition of 200 g of 4'-chloroacetophenone. The resultant mixture was stirred with heating overnight at 100° C. The reaction mixture was poured into 2,000 ml of ice water and extracted with ethyl acetate. The ethyl acetate layer was washed with water and dried over anhydrous magnesium sulfate, and the solvent was distilled off under reduced pressure. n-Hexane was added to the residue, and the resultant crystals were collected by filtration and washed with n-hexane. Thus was obtained 224 g of 4'-phenylthioacetophenone as crystals (m.p. 48°–50° C.).

$^1$H-NMR ($\delta$: ppm): [Solvent: CDCl$_3$] 2.55 (3H, s), 7.21 (2H, d, J=8.7), 7.39–7.42 (3H, m), 7.48–7.51 (2H, m), 7.82 (2H, d, J=8.7)

To an ice-cooled solution of 220 g of the crystals obtained as described above in dichloromethane (1,500 ml) was added 6.5 g of anhydrous aluminum chloride, followed by gradual and dropwise addition of 162 g of bromine. The resultant mixture was stirred at room temperature for 5 hours. 1N Hydrochloric acid (500 ml) was added dropwise to the reaction mixture and, after stirring, the organic layer was separated, washed with water and dried over anhydrous magnesium sulfate, and the solvent was then distilled off under reduced pressure. n-Hexane was added to the residue. The resultant crystals were collected by filtration and washed with n-hexcane to give 151.3 g of the desired compound as crystals. The compound obtained was designated as Compound No. 1a. Its structure is shown in Table 1 and its typical physical properties are shown in Table 2.

Reference Examples 2 to 9

The compounds respectively having the structures shown in Table 1 under compounds Nos. 2a to 9a were obtained in the same manner as in Reference Example 1. Some physical properties of each compound obtained are shown in Table 2.

Reference Example 10

Production of 2-bromo-4'-methylthiopropiophenone

Propionic anhydride (93 ml) was gradually added dropwise to a solution of 100 g of thioanisole and 240 g of anhydrous aluminum chloride in 250 ml of carbon disulfide, and the mixture was stirred at 40° C. for 2 hours. The reaction mixture was poured gradually into ice-cooled 3N hydrochloric acid and extracted with dichloromethane. The organic layer was washed with water, dried over anhydrous magnesium sulfate and concentrated under reduced pressure. n-Hexane was added to the residue and the resultant crystals were collected by filtration and further washed with n-hexane. Thus was obtained 92.0 g of 4'-methylthiopropiophenone as crystals (m.p. 55°–56° C.).

$^1$H-NMR ($\delta$: ppm): [Solvent: CDCl$_3$] 1.21 (3H, t, J=7.3), 2.52 (3H, s), 2.95 (2H, q, J=7.3), 7.26 (2H, d, J=8.6), 7.88 (2H, d, J=8.6)

The crystals obtained above were brominated in the same manner as in Reference Example 1 to give the objective compound. The compound obtained was designated as Compound No. 10a. Its structure is shown in Table 1 and typical physical properties thereof are shown in Table 2.

Reference Example 11

Production of 2-bromo-4'-phenylsulfonylpropiophenone

4'-Phenylthiopropiophenone (26 g) was dissolved in 100 ml of acetic acid, 41 ml of 31% aqueous hydrogen peroxide was added, and the mixture was heated at 80° C. for 5 hours. After completion of the reaction, the mixture was concentrated and extracted with dichloromethane. The organic layer was dried over anhydrous magnesium sulfate and concentrated under reduced pressure, followed by addition of n-hexane. The resultant crystals were collected by filtration and further washed with n-hexane to give 21.4 g of 4'-phenylsulfonylpropiophenone as crystals (m.p. 83°–84° C.).

$^1$H-NMR ($\delta$: ppm): [Solvent: CDCl$_3$] 1.22 (3H, t, J=7.3), 3.03 (2H, q, J-7.3), 7.38–7.63 (3H, m), 7.94–8.16 (6H, m)

The crystals obtained above were brominated in the same manner as in Reference Example 1 to give the objective compound. The compound obtained was designated as Compound No. 11a. Its structure is shown in Table 1 and typical physical properties thereof are shown in Table 2.

Reference Example 12

Production of 2-bromo-4'-phenylselenylpropiophenone

Selenium (7.1 g) was suspended in 60 ml of anhydrous THF under nitrogen. Thereto was added dropwise 55 ml of 1.8M phenyl-lithium at room temperature. The mixture was stirred for 15 minutes. Then, a solution of 12.6 g of 4'-chloropropiophenone in 20 ml of DMF was added dropwise to the mixture obtained above. The resultant mixture was stirred at 100° C. for 3 hours. After allowing to cool, 50 ml of water was added, and the mixture was extracted with diethyl ether (100 ml×3 times). The organic layers were combined, washed with water, dried over anhydrous magnesium sulfate and concentrated under reduced pressure to give 16.4 g of 4'-phenylselenylpropiophenone as crystals (m.p. 63°–65° C.).

A 12.7-g portion of the crystals obtained were dissolved in 100 ml of dichloromethane, 300 mg of anhydrous aluminum chloride was added at 0° C. with stirring, and 7.1 g of bromine was further added dropwise. After stirring at 0° C. for 1 hour, water was added, and the mixture was extracted with dichloromethane (100 ml×3 times). The organic layers were combined, washed with water, dried over anhydrous magnesium sulfate and concentrated under reduced pressure. The residue obtained was purified by silica gel chromatography (developing solvent: dichloromethane) to give 11.5 g of the objective compound as crystals (m.p. 70°–71° C.).

$^1$H-NMR ($\delta$: ppm): [Solvent: CDCl$_3$] 1.87 (3H, d, J=6.6), 5.20 (1H, q, J=6.6), 7.30–7.65 (7H, m), 7.84 (2H, d, J=8.6)

Reference Example 13

Production of 2-bromo-3'-isopropyl-4'-methylthiopropiophenone

The procedure of Reference Example 10 was followed using 1-isopropyl-2-methylthiobenzene, to give the objective compound as an oil.

$^1$H-NMR ($\delta$: ppm): [Solvent: CDCl$_3$] 1.29 (6H, d, J=6.9), 1.90 (3H, d, J=6.6), 2.52 (3H, s), 5.28 (1H, q, J=6.6), 7.19 (1H, d, J=8.4), 7.83 (1H, dd, J=8.4, 2.0), 7.91 (1H, d, J=2.0)

Example 1

Production of 5-methoxy-2-(4-phenylthiophenyl)indole

A mixture of 212 g of p-anisidine and 300 ml of N,N-dimethylaniline was heated to 170° C. Thereto was added portionwise 150 g of Compound 1a, followed by 3 hours of stirring at 170° C. The reaction mixture was poured into 1,500 ml of ice-cooled 3N hydrochloric acid, and extracted with ethyl acetate. The ethyl acetate layer was washed twice with 3N hydrochloric acid, dried over anhydrous magnesium sulfate and concentrated under reduced pressure. The residue obtained was purified by silica gel column chromatography (developing solvent: dichloromethane) to give 84.9 g of the objective compound.

The structure of the compound obtained is shown in Table 3 and typical physical properties of said compound are shown in Table 4.

Examples 2 to 13

The compounds specified in Table 3 were obtained in the same manner as in Example 1. Typical physical properties of each compound obtained are shown in Table 4.

Example 14

Production of 1-ethyl-5-methoxy-2-(4-phenylthiophenyl)indole

A 6 g portion of the compound obtained in Example 1 was dissolved in 50 ml of DMF, and 850 mg of sodium amide was added with ice cooling. The mixture was stirred for 20 minutes. Thereto was gradually added dropwise a solution of 1.41 ml of bromoethane in DMF (25 ml). The mixture was stirred overnight at 20° C. The reaction mixture was poured into water and extracted with ethyl acetate. The organic layer was dried over anhydrous magnesium sulfate and concentrated under reduced pressure. The residue obtained was purified by silica gel column chromatography (developing solvent: dichloromethane:n-hexane=1:1) to give 2.62 g of the objective compound.

The structure of the compound obtained is shown in Table 5 and typical physical properties thereof are shown in Table 6.

Examples 15 to 24

The compounds specified in Table 5 were obtained in the same manner as in Example 14. Typical physical properties of each compound obtained are shown in Table 6.

Example 25

Production of 5-methoxy-3-methyl-1-[6-oxo-6-(1-pyrrolidinyl)hexyl]-2-(4-phenylthiophenyl)indole A 5.35 g quantity of the compound obtained in Example 2 was dissolved in 30 ml of N,N-dimethylacetamide. With ice cooling, 1.14 g of 60% sodium hydride was added and the mixture was stirred for 20 minutes. Thereto was gradually added dropwise 6 g of 6-bromohexanepyrrolidineamide. The mixture was stirred at 20° C. for 3 hours. The reaction mixture was poured into ice water and extracted with ethyl acetate. The organic layer was dried over anhydrous magnesium sulfate and concentrated under reduced pressure. The residue obtained was purified by silica gel column chromatography (developing solvent: dichloromethane:methanol=50:1) to give 5.48 g of the objective compound.

The structure of the compound obtained is shown in Table 7 and typical physical properties thereof are shown in Table 8.

Examples 26 to 83

The compounds specified in Table 7 were obtained in the same manner as in Example 25. Typical physical properties of each compound obtained are shown in Table 8.

Example 84

Production of 1-ethyl-5-hydroxy-2-(4-phenylthiophenyl)indole

A 1.3 g quantity of the compound obtained in Example 14 was dissolved in 30 ml of dichloromethane and the solution was cooled to −60° C. in an acetone-dry ice bath. Thereto was gradually added dropwise 9.1 ml of 1M boron tribromide. The mixture was then stirred overnight at room temperature. A saturated aqueous solution of sodium hydrogen carbonate was gradually added dropwise to the reaction mixture. The organic layer was separated, washed with water, dried over anhydrous magnesium sulfate and concentrated under reduced pressure. Diethyl ether and n-hexane were added to the residue and the resultant solid was collected by filtration and recrystallized from ethyl acetate-diethyl ether-n-hexane to give 730 mg of the objective compound as crystals.

The structure of the compound obtained is shown in Table 9 and typical physical properties thereof are shown in Table 10.

Examples 85 to 95

The compounds specified in Table 9 were obtained in the same manner as in Example 84. Typical physical properties of each compound obtained are shown in Table 10.

Examples 96–154

The compounds specified in Table 11 were obtained in the same manner as in Example 84. Typical physical properties of each compound obtained are shown in Table 12.

Example 155

Production of 1-(5-ethoxycarbonylpentyl)-5-hydroxy-2-(4-phenylthiophenyl)indole

The procedure of Example 25 was followed using the compound obtained in Example 1 and ethyl 6-bromohexanoate, to give 1-(5-ethoxycarbonylpentyl)-5-methoxy-2-(4-phenylthiophenyl)indole. Using this crude product, the objective compound was obtained in the same manner as in Example 84. The structure of the compound obtained is shown in Table 11 and typical physical properties thereof are shown in Table 12.

Example 156

Production of 5-hydroxy-3-methyl-2-(4-phenylthiophenyl)-1-(6-pyrrolidinylhexyl)indole A solution of 2.3 g of the compound obtained in Example 96 in 100 ml of anhydrous THF was gradually added dropwise to a suspension of 875 mg of lithium aluminum hydride in anhydrous THF (100 ml). After heating under reflux for 2 hours, the reaction mixture was cooled with ice and a saturated aqueous solution of sodium hydrogen carbonate was gradually added dropwise. The mixture was extracted with ethyl acetate. The organic layer was washed with water, dried over anhydrous magnesium sulfate and concentrated under reduced pressure. The residue obtained was purified by silica gel column chromatography (developing solvent: dichloromethane:methanol=10:1→5:1) to give 1.53 g of the objective compound.

The structure of the compound obtained is shown in Table 13 and typical physical properties thereof are shown in Table 14.

Examples 157 to 182

The compounds specified in Table 13 were obtained in the same manner as in Example 156. Typical physical properties of each compound obtained are shown in Table 14.

Example 183

Production of 5-hydroxy-3-methyl-2-(4-methylsulfinyl-phenyl)-1-[6 -oxo-6-(1-pyrrolidinyl)hexyl]indol A 1 g quantity of the compound obtained in Example 131 was dissolved in 10 ml of dichloromethane, 465 mg of 80% m-chloroperbenzoic acid was added, and the mixture was stirred overnight at 0° C. After completion of the reaction, gaseous ammonia was blown into the reaction mixture. The resultant precipitate was filtered off and the filtrate was concentrated under reduced pressure. The residue was purified by silica gel column chromatography (dichloromethane:methanol=15:1) to give 450 mg of the-objective compound as an amorphous powder.

$^1$H-NMR (δ: ppm): [CDCl$_3$] 1.07–1.97 (10H, m), 2.13 (2H, t, J=7.4), 2.17 (3H, s), 2.84 (3H, s), 3.32 (2H, t, J=6.7), 3.44 (2H, t, J=6.7), 3.94 (2H, t, J=7.3), 6.06 (1H, brs), 6.85 (1H, dd, J=8.7, 2.4), 7.02 (1H, d, J=2.4), 7.17 (1H, d, J=8.7), 7.51 (2H, d, J=8.4), 7.76 (2H, d, J=8.4)

Example 184

Production of 5-hydroxy-3-methyl-1-[6-oxo-6-(1-pyrrolidinyl)hexyl]-2-(4 -phenylsulfinylphenyl)indole Using the compound obtained in Example 96, the above objective compound was obtained in the same manner as in Example 183 as an amorphous powder.

$^1$H-NMR (δ: ppm): [CDCl$_3$] 1.03–1.98 (10H, m), 2.07–2.15 (5H, m), 3.31 (2H, t, J=6.8), 3.43 (2H, t, J=6.8), 3.92 (2H, t, J=7.6), 6.82 (1H, dd, J=8.7, 2.4), 6.98 (1H, d, J=2.4), 7.16 (1H, d, J=8.7), 7.26–7.75 (9H, m)

Example 185

Production of 5-benzoyloxy-3-methyl-2-(4-methylthio-phenyl)-1-[6-oxo-6 -(1-pyrrolidinyl)hexyl]indole A 1.5 g quantity of the compound obtained in Example 131 was dissolved in 20 ml of pyridine, 0.66 ml of benzoyl chloride was added, and the mixture was stirred at 20° C. for 3 hours. After completion of the reaction, 1N hydrochloric acid was added to make the mixture acidic, followed by extraction with ethyl acetate. The organic layer was dried over anhydrous magnesium sulfate and concentrated under reduced pressure. The residue was purified by silica gel column chromatography (dichloromethane:methanol=50:1) to give 1.54 g of the objective compound as crystals (m.p. 100°–102° C.).

$^1$H-NMR (δ: ppm): [CDCl$_3$] 1.12–1.92 (10H, m), 2.13 (2H, d, J=7.4), 2.19 (3H, s), 2.56 (3H, s), 3.32 (2H, t, J=6.6), 3.43 (2H, t, J=6.6), 4.03 (2H, d, J=7.4), 7.05 (1H, dd, J=8.9, 2.3), 7.27–8.28 (11H, m)

Example 186

Production of 5-acetoxy-3-methyl-2-(4-methylthiophenyl)-1-[6 -oxo-6-(1-pyrrolidinyl)hexyl]indole A 1.7 g quantity of the compound obtained in Example 131 was dissolved in 15 ml of pyridine and 1.1 ml of acetic anhydride, and the mixture was stirred at 20° C. for 1.5 hours. The reaction mixture was cooled with ice, acidified by addition of 1N hydrochloric acid and extracted with ethyl acetate. The organic layer was washed with water, dried over anhydrous magnesium sulfate and concentrated under reduced pressure to give 970 mg of the objective compound as an oil.

$^1$H-NMR (δ: ppm): [CDCl$_3$] 1.16–1.94 (10H, m), 2.11 (2H, d, J=7.5), 2.169 (3H, s), 2.171 (3H, s), 2.33 (3H, s), 2.55 (3H, s), 3.30 (2H, t, J=6.7), 3.42 (2H, t, J=6.7), 4.00 (2H, d, J=7.4), 6.92 (1H, dd, J=8.7, 2.2), 7.24–7.36 (6H, m)

Example 187

Production of 5-acetoxy-1-[6-(N-acetyl-N-cyclopentylamino)hexyl]-3-methyl-2-(4-phenylthiophenyl)indole Using the compound obtained in Example 159, the above objective compound was obtained as an amorphous powder in the same manner as in Example 186.

$^1$H-NMR (δ: ppm): [CDCl$_3$] 1.03–1.90 (16H, m), 2.02, 2.09 (total 3H, each s), 2.17 (3H, m), 2.95–3.07 (2H, m), 3.90–4.03 (3H, m), 4.57–4.63 (1H, m), 6.90–7.50 (12H, m)

Example 188

Production of 1-[6-(N-acetyl-N-cyclopentylamino)hexyl]-5 -hydroxy-3-methyl-2-(4-phenylthiophenyl)indole A 2.65 g quantity of the compound obtained in Example 187 was dissolved in 10 ml of dioxane, 10 ml of 30% aqueous sodium hydroxide was added, and the mixture was heated at 60° C. for 3 hours. After completion of the reaction, the mixture was extracted with ethyl acetate. The ethyl acetate layer was dried and concentrated, and the residue obtained was purified by silica gel column chromatography (dichloromethane:methanol=15:1) to give the above objective compound as an amorphous powder.

$^1$H-NMR (δ: ppm): [CDCl$_3$] 1.03–1.98 (16H, m), 2.11 (3H, s), 2.16 (3H, s), 3.01 (2H, t, J=7.3), 3.98 (2H, t, J=7.2), 4.43–4.61 (1H, m), 4.83–5.08 (1H, brs), 6.83 (1H, dd, J=2.3, 8.6), 6.99 (1H, d, J=2.3), 7.13 (1H, d, J=8.6), 7.20–7.50 (9H, m)

Example 189

Production of 1-(5-carboxypentyl)-5-hydroxy-3-methyl-2-(4-phenylthiophenyl)indole A 1 g quantity of the compound obtained in Example 151 was dissolved in 7 ml of dioxane, 7 ml of 2N aqueous sodium hydroxide was added, and the mixture was heated at 60° C. for 2 hours. After completion of the reaction, the mixture was acidified by addition of diluted hydrochloric acid and extracted with ethyl acetate. The organic layer was dried and concentrated to give 910 mg of the objective compound as an amorphous powder.

$^1$H-NMR (δ: ppm): [CDCl$_3$] 1.06–1.63 (6H, m), 2.15 (3H, s), 2.20 (2H, t, J=7.5), 3.95 (2H, t, J=7.2), 6.79 (1H, dd, J=8.7, 2.4), 6.97 (1H, d, J=2.4), 7.15 (1H, d, J=8.7), 7.23–7.48 (9H, m)

Example 190

Production of 1-(5-carboxypentyl)-2-(4-ethylthiophenyl)-5-hydroxy-3-methylindole The procedure of Example 189 was followed using the compound obtained in Example 153 to give the objective compound as an amorphous powder.

$^1$H-NMR (δ: ppm): [CDCl$_3$] 1.33–1.65 (6H, m), 1.38 (3H, t, J=7.4), 2.16 (3H, s), 2.21 (2H, t, J=7.5), 3.02 (2H, q, J=7.4), 3.97 (2H, t, J=7.3), 6.79 (1H, dd, J=8.6, 2.4), 6.98 (1H, d, J=2.4), 7.17 (1H, d, J=8.6), 7.27 (2H, d, J=8.3), 7.39 (2H, d, J=8.3)

Example 191

Production of 5-hydroxy-1-(6-hydroxyhexyl)-3-methyl-2-(4-phenylthiophenyl)indole A solution of 1.08 g of the compound obtained in Example 151 in 15 ml of THF was gradually added dropwise to a suspension of 1 g of lithium aluminum hydride in 35 ml of THF, and the mixture was stirred at 0° C. for 2 hours. After completion of the reaction, the mixture was acidified by gradual dropwise addition of diluted sulfuric acid, the resultant precipitate was filtered off, and the filtrate was extracted with ethyl acetate. The organic layer was dried and concentrated under reduced pressure to give 600 mg of the objective compound as an amorphous powder.

$^1$H-NMR (δ: ppm): [CDCl$_3$] 1.06–1.90 (8H, m), 2.17 (3H, s), 3.54 (2H, t, J=6.5), 3.73 (1H, t, J=6.5), 3.97 (2H, t, J=7.4), 6.79 (1H, dd, J=8.7, 2.3), 6.97 (1H, d, J=2.3), 7.18 (1H, d, J=8.7), 7.25–7.50 (9H, m)

Example 192

Production of 3,6-dibromo-5-methoxy-2-(4-phenylthiophenyl)indole

A 5.0 g quantity of the compound obtained in Example 1 was dissolved in 20 ml of dioxane, 2.8 g of pyridine was added and, with ice cooling and stirring, 4.8 g of bromine was added dropwise, followed by 2 hours of stirring at 10° C. After completion of the reaction, 10 ml of water was added and the mixture was extracted with dichloromethane. The organic layer was dried over anhydrous magnesium sulfate and concentrated under reduced pressure. The residue was purified by silica gel column chromatography (dichloromethane) to give 4.1 g of the objective compound as crystals (m.p. 138°–139° C.).

$^1$H-NMR (δ: ppm): [CDCl$_3$] 3.93 (3H, s), 7.01 (1H, s), 7.30–7.51 (7H, m), 7.55 (1H, s), 7.70 (2H, dd, J=6.7, 2.0), 8.15 (1H, brs)

Example 193

Production of 1-(5-ethoxycarbonylpentyl)-5-hydroxy-2-(4-phenylthiophenyl)indole

A solution of 2.5 g of the compound obtained in Example 83 in dichloromethane (10 ml) was added dropwise to a mixture of 10 ml of ethanethiol and 2.1 g of anhydrous aluminum chloride with cooling in an ice-water bath. The mixture was stirred at room temperature for 2.5 hours, then acidified by dropwise addition of 2N hydrochloric acid, and extracted with chloroform. The chloroform layer was washed with saturated saline, dried over anhydrous magnesium sulfate and concentrated under reduced pressure. The residue was recrystallized from n-hexane-diethyl ether to give 480 mg of the objective compound as crystals. The melting point and $^1$H-NMR spectrum of the compound obtained were in agreement with those of the compound obtained in Example 155.

Example 194

Production of 2-(3-isopropyl-4-methylthiophenyl)-5-methoxy-3-methylindole

The procedure of Example 1 was followed using the compound obtained in Reference Example 13 to give the objective compound as crystals (m.p. 138°–140° C.).

$^1$H-NMR (δ: ppm): [CDCl$_3$] 1.29 (3H, s), 1.32 (3H, s), 2.42 (3H, s), 2.50 (3H, s), 3.35–3.50 (1H, m), 3.89 (3H, s), 6.85 (1H, dd, J=8.6, 2.3), 7.02 (1H, d, J=2.3), 7.24 (1H, d, J=8.6), 7.26 (1H, d, J=8.2), 7.36 (1H, dd, J=8.2, 1.9), 7.43 (1H, d, J=1.9), 7.89 (1H, brs)

Examples 195 to 231

The compounds specified in Table 15 were obtained in the same manner as in Example 25. Typical physical properties of each compound obtained are shown in Table 16.

Example 232

Production of 2-(3-isopropyl-4-methylthiophenyl)-5-methoxy-3-methyl-1-[8-oxo-8-(1-pyrrolidinyl)octyl]indole The procedure of Example 25 was followed using the compound obtained in Example 194 to give the objective compound as an oil.

$^1$H-NMR (δ: ppm): [CDCl$_3$] 1.00–2.01 (14H, m), 1.25 (3H, s), 1.28 (3H, s), 2.23 (3H, s), 2.25 (2H, t, J=7.6), 2.53 (3H, s), 3.31–3.51 (4H, m), 3.90 (3H, s), 3.95 (2H, t, J=7.6), 6.87 (1H, dd, J=8.9, 2.3), 7.02 (1H, d, J=2.3), 7.16–7.30 (4H, m)

Example 233

Production of 1-(8-isopropylcarbamoyloctyl)-2-(3-iso-propyl-4-methylthiophenyl)-5-methoxy-3-methylindole The procedure of Example 25 was followed using the compound obtained in Example 194 to give the objective compound as an oil.

$^1$H-NMR (δ: ppm): [CDCl$_3$] 1.00–1.68 (10H, m), 1.12 (3H, s), 1.14 (3H, s), 1.26 (3H, s), 1.29 (3H, s), 2.03 (2H, t, J=7.6), 2.22 (3H, s), 2.53 (3H, s), 3.33–3.50 (1H, m), 3.89 (3H, s), 3.96 (2H, t, J=7.6), 3.99–4.17 (1H, m), 5.22 (1H, br), 6.88 (1H, dd, J=8.9, 2.3), 7.03 (1H, d, J=2.3), 7.16–7.29 (4H, m)

Example 234

Production of 5-hydroxy-2-(4-phenylthiophenyl)-1-[4-{2-(1-pyrrolidinyl)ethoxy}benzoyl]indole Ethanethiol (3.7 ml) was added dropwise to 2.65 g of anhydrous aluminum chloride with ice cooling. The mixture was stirred at room temperature for 10 minutes and then again cooled with ice, and a solution of the compound obtained in Example 196 in 50 ml of dichloromethane was gradually added dropwise. The mixture was stirred at room temperature for 1 hour, then cooled with ice, diluted with water, made neutral by dropwise addition of saturated aqueous sodium hydrogen carbonate, and extracted with dichloromethane-methanol (10:1). The organic layer was washed with saturated saline, dried over anhydrous magnesium sulfate and concentrated under reduced pressure. The residue was purified by silica gel chromatography (developing solvent: dichloromethane:methanol=30:1) and further recrystallized from n-hexane-dichloromethane to give 1.89 g of the objective compound as crystals.

The structure of the compound obtained is shown in Table 17 and typical physical properties thereof are shown in Table 18.

Examples 235 to 271

The compounds specified in Table 17 were obtained in the same manner as in Example 234. Typical physical properties of each compound obtained are shown in Table 18.

Examples 272 to 292

The compounds specified in Table 19 were obtained in the same manner as in Example 156. Typical physical properties of each compound obtained are shown in Table 20.

TABLE 1

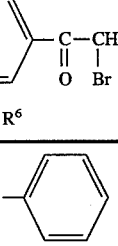

| No. | R$^3$ | R$^6$ | X |
|---|---|---|---|
| 1a | H | phenyl | 0 |
| 2a | CH$_3$ | phenyl | 0 |

TABLE 1-continued

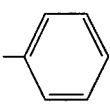

| No. | R$^3$ | R$^6$ | X |
|---|---|---|---|
| 3a | —C$_2$H$_5$ | phenyl | 0 |
| 4a | CH$_3$ | cyclohexyl | 0 |
| 5a | CH$_3$ | —C$_2$H$_5$ | 0 |
| 6a | CH$_3$ | —CH$_2$-phenyl | 0 |
| 7a | CH$_3$ | -n-C$_4$H$_9$ | 0 |
| 8a | CH$_3$ | 4-methylphenyl | 0 |
| 9a | CH$_3$ | pyridyl | 0 |
| 10a | CH$_3$ | —CH$_3$ | 0 |
| 11a | CH$_3$ | phenyl | 2 |

TABLE 2

| No. | mp (°C.) | $^1$H-NMR(CDCl$_3$) |
|---|---|---|
| 1a | 52–53 | 4.37(2H, s), 7.19(2H, d, J=8.8), 7.41–7.45(3H, m), 7.50–7.54(2H, m), 7.84 (2H, d, J=8.8) |
| 2a | 82–84 | 1.88(3H, d, J=6.6), 7.40–7.43(3H, m), 5.21(1H, q, J=6.6), 7.50–7.54(2H, m), 7.19(2H, d, J=8.6), 7.88(2H, d, J=8.6) |
| 3a | Oil | 1.06(3H, t, J=7.4), 2.05–2.30(2H, m), 4.99(1H, dd, J=6.6, 6.3), 7.20(2H, d, J=8.6), 7.36–7.44(3H, m), 7.48–7.54 (2H, m), 7.87(2H, d, J=8.6) |
| 4a | 77–81 | 1.33–2.08(10H, m), 1.89(3H, d, J=6.7) 3.30–3.41(1H, m), 5.24(1H, q, J=6.7), 7.35(2H, d, J=8.9), 7.91(2H, d, J=8.9 |
| 5a | 59–60 | 1.39(3H, t, J=7.4), 1.89(3H, d, J=6.6) 3.04(2H, q, J=6.6), 5.25(1H, q, J=6.6) 7.31(2H, d, J=8.5) |
| 6a | Oil | 1.88(3H, d, J=6.6), 4.23(2H, s), 5.22 (1H, q, J=6.6), 7.25–7.40(7H, m), 7.90(2H, d, J=8.9) |
| 7a | 62–63 | 0.96(3H, t, J=7.3), 1.42–1.76(4H, m), 1.89(3H, d, J=6.7), 3.01(2H, t, J=7.3) 5.25(1H, q, J=6.7), 7.31(2H, d, J= 8.6) 7.92(2H, d, J=8.6) |
| 8a | Oil | 1.87(3H, d, J=6.7), 2.41(3H, s), 5.20 (1H, q, J=6.7), 7.15(2H, d, J=8.5), 7.24(2H, d, J=8.1), 7.43(2H, d, J=8.1) |

TABLE 2-continued

| No. | mp (°C.) | ¹H-NMR(CDCl₃) |
|---|---|---|
| 9a | Oil | 7.86(2H, d, J=8.5)<br>1.92(3H, d, J=6.6), 5.26(1H, q, J=6.6)<br>7.18–7.27(3H, m), 7.62–7.73(3H, m),<br>8.0(2H, d, J=8.4), 8.51–8.57(1H, m) |
| 10a | 81~83 | 1.89(3H, d, J=6.6), 2.53(3H, s), 5.25<br>(1H, q, J=6.6), 7.28(2H, d, J=8.3)<br>7.93(2H, d, J=8.3) |
| 11a | 83~84 | 1.90(3H, d, J=6.6), 5.30(1H, q, J=6.6)<br>7.54–7.67(3H, m), 7.95–8.19(6H, m) |

TABLE 3

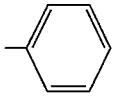

| Example | (R¹)x | R²O— | R³ | R⁶ | n |
|---|---|---|---|---|---|
| 1 | H | 5CH₃O— | H | phenyl | 0 |
| 2 | H | 5CH₃O— | —CH₃ | phenyl | 0 |
| 3 | H | 6CH₃O— | —CH₃ | phenyl | 0 |
| 4 | 4,6-di-Br | 5CH₃O— | —CH₃ | phenyl | 0 |
| 5 | H | 5CH₃O— | —C₂H₅ | phenyl | 0 |
| 6 | H | 5CH₃O— | —CH₃ | cyclohexyl | 0 |
| 7 | H | 5CH₃O— | —CH₃ | —C₂H₅ | 0 |
| 8 | H | 5CH₃O— | —CH₃ | —CH₂-phenyl | 0 |
| 9 | H | 5CH₃O— | —CH₃ | nC₄H₉— | 0 |
| 10 | H | 5CH₃O— | —CH₃ | 4-CH₃-phenyl | 0 |
| 11 | H | 5CH₃O— | —CH₃ | 2-pyridyl | 0 |

TABLE 3-continued

| Example | (R¹)x | R²O— | R³ | R⁶ | n |
|---|---|---|---|---|---|
| 12 | H | 5CH₃O— | —CH₃ | —CH₃ | 0 |
| 13 | H | 5CH₃O— | —CH₃ | phenyl | 2 |

TABLE 4

| No. | mp (°C.) | ¹H-NMR(CDCl₃) |
|---|---|---|
| 1 | 112~118 | 3.86(3H, s), 6.74(1H,(1H, d, J=2.1), 6.85<br>(1H, dd, J=8.7, 2.4), 7.08(1H, d, J=<br>2.4), 7.27–7.41(8H, m), 7.55(2H, d,<br>J=6.4), 8.20(1H, brs) |
| 2 | 112~116 | 2.42(3H, s), 3.88(3H, s), 6.87(1H, dd,<br>J=8.7, 2.5), 7.02(1H, d, J=2.5),<br>7.22–7.50(10H, m), 7.86(1H, brs) |
| 3 | 108~110 | 2.41(3H, s), 3.84(3H, s), 6.81(1H, dd,<br>J=8.4, 2.3), 6.83(1H, d, J=2.3),<br>7.24–7.47(10H, m), 7.87(1H, brs) |
| 4 | Oil | 2.62(3H, s), 3.90(3H, s),<br>7.34–7.47(10H, m), 7.98(1H, brs) |
| 5 | Oil | 1.32(3H, t, J=7.6), 2.87 (2H, q, J=<br>7.6), 3.88(3H, s), 6.87(1H, dd, J=8.4,<br>2.3), 7.06(1H, d, J=2.3), 7.26–7.50<br>(9H, m), 7.84(1H, brs) |
| 6 | 103~104 | 1.20–2.04(10H, m), 2.42(3H, s),<br>3.10–3.20(1H, m), 3.88(3H, s),<br>6.86(1H, dd, J=8.3, 2.4),<br>7.02(1H, d, J=2.4), 7.23(1H, d, J=<br>8.3), 7.46(4H, s), 7.88(1H, brs) |
| 7 | 93~97 | 1.35(3H, t, J=7.4), 2.41(3H, s), 2.98<br>(2H, q, J=7.4), 3.88(3H, s), 6.85<br>(1H, dd, J=8.5, 2.4), 7.01(1H, d, J=<br>2.4), 7.20(1H, d, J=8.5), 7.37(2H, d,<br>J=8.7), 7.65(2H, d, J=8.7) |
| 8 | 125~127 | 2.41(3H, s), 3.68(3H, s), 4.17(2H,<br>s), 6.86(1H, dd, J=8.7, 2.4), 7.02<br>(1H, d, J=2.4), 7.23–7.64(10H, m),<br>7.87(1H, brs) |
| 9 | 82~83 | 0.94(3H, t, J=7.3), 1.41–1.72(4H, m)<br>2.42(3H, s), 2.94(2H, t, J=7.3),<br>3.89(3H, s), 6.86(1H, dd, J=8.5, 2.4)<br>7.02 (1H, d, J=2.4), 7.23(1H, d, J=<br>8.5), 7.37(2H, d, J=8.6), 7.47(2H, d,<br>J=8.6), 7.88(1H, brs) |
| 10 | 89~91 | 2.37(3H, s), 2.41(3H, s), 3.88(3H, s)<br>6.86(1H, dd, J=8.7, 2.5), 7.01(1H, d,<br>J=2.5), 7.22–7.46(9H, m), 7.85(1H,<br>brs) |
| 11 | 144~147 | 2.44(3H, s), 3.89(3H, s),<br>88(1H, dd, J=8.7, 2.4),<br>7.00–7.67(9H, m), 8.02(1H, brs),<br>8.43–8.46(1H, m) |
| 12 | 132~134 | 2.40(3H, s), 2.51(3H, s), 3.88(3H, s)<br>6.85(1H, dd, J=8.6, 2.4),<br>7.01(1H, d, J=2.4), 7.21(1H, d, J=<br>8.6), 7.31(2H, d, J=8.4), 7.45(2H, d,<br>J=8.4), 7.87(1H, brs) |
| 13 | 163~166 | 2.43(3H, s), 3.88(3H, s),<br>6.90(1H, dd, J=8.6, 2.3), 7.01(1H, d, |

TABLE 4-continued

| No. | mp (°C.) | ¹H-NMR(CDCl₃) |
|---|---|---|
| | | J=2.3), 7.26–8.10(11H, m) |

TABLE 6

| No. | mp (°C.) | ¹H-NMR(CDCl₃) |
|---|---|---|
| 14 | 66–67 | 1.30(3H, t, J=7.22), 3.86(3H, s), 4.15(2H, q, J=7.2), 6.44(1H, d, J= |

TABLE 5

$$\text{(R}^1\text{)x} \text{ indole with R}^2\text{O-, R}^3, R^5\text{ on N, and 2-position bearing phenyl-S(O)}_n\text{R}^6$$

| Example | (R¹) x | R²O— | R³ | R⁶ | n | R⁵ |
|---|---|---|---|---|---|---|
| 14 | H | 5CH₃O— | H | phenyl | 0 | —C₂H₅ |
| 15 | H | 5CH₃O— | H | phenyl | 0 | —CH₂CH₂CH₃ |
| 16 | H | 5CH₃O— | CH₃ | phenyl | 0 | —C₂H₅ |
| 17 | H | 5CH₃O— | CH₃ | phenyl | 0 | —(CH₂)₃CH₃ |
| 18 | H | 5CH₃O— | CH₃ | phenyl | 0 | —(CH₂)₅CH₃ |
| 19 | H | 5CH₃O— | —CH₃ | phenyl | 0 | —(CH₂)₉CH₃ |
| 20 | H | 5CH₃O— | —CH₃ | phenyl | 0 | —CH₂CH₂CH₃ |
| 21 | H | 6CH₃O— | —CH₃ | phenyl | 0 | —C₂H₅ |
| 22 | H | 6CH₃O— | —CH₃ | phenyl | 0 | —(CH₂)₂CH₃ |
| 23 | H | 5CH₃O— | —CH₃ | —CH₃ | 2 | —(CH₂)₃CH₃ |
| 24 | H | 5CH₃O— | —CH₃ | phenyl | 2 | —(CH₂)₂CH₃ |

TABLE 6-continued

| No. | mp (°C.) | ¹H-NMR(CDCl₃) |
|---|---|---|
| 15 | 75~77 | 0.83), 6.89(1H, dd, J=8.9, 2.4), 7.09 (1H, d, J=2.4), 7.26–7.48(10H, m) 0.76(3H, t, J=7.4), 1.70(2H, q, J=7.4) 3.86(3H, 4.07(2H, t, J=7.6), 6.43(1H, dd, J=8.9, 2.5), 7.08(1H, d, J=2.5), 7.25–7.50(10H, m) |
| 16 | 98~100 | 1.18(3H, t, J=7.2), 2.21(3H, s), 3.89(3H, s), 4.03(2H, q, J=7.6), 6.90(1H, dd, J=8.7, 2.4), 7.03(1H, d, J=2.4), 7.23–7.50(10H, m) |
| 17 | Oil | 0.76(3H, t, J=7.3), 1.07–1.57(4H, m), 2.21(3H, s), 3.88(3H, s), 3.97(2H, t, J=7.5), 6.89(1H, dd, J=8.6, 2.3), 7.02(1H, d, J=2.3), 7.21–7.47(10H, m) |
| 18 | Oil | 0.80(3H, t, J=7.1), 1.09–1.57(8H, m) 2.21(3H, s), 3.88(3H, s), 3.96(2H, t, J=7.6), 6.89(1H, dd, J=8.8, 2.4), 7.02(1H, d, J=2.4), 7.21–7.47(10H, m) |
| 19 | Oil | 0.87(3H, t, J=7.2), 1.05–1.62(16H, m) 2.21(3H, s), 3.88(3H, s), 3.96(2H, t, J=7.6), 6.89(1H, dd, J=8.7, 2.4), 7.02(1H, d, J=2.4), 7.21–7.48(10H, m) |
| 20 | Oil | 0.73(3H, t, J=7.4), 1.61(2H, q, J=7.6) 2.21(3H, s), 3.89(3H, s), 3.92(2H, t, J=7.4), 6.78–6.83(2H, m), 7.24–7.48(10H, m) |
| 21 | 80~81 | 1.19(3H, t, J=7.1), 2.21(3H, s), 3.89(3H, s), 4.01(2H, q, J=7.1), 6.79–6.82(2H, m), 7.24–7.50(10H, m) |
| 22 | Oil | 0.73(3H, t, J=7.4), 1.61(2H, q, J=7.6) 2.21(3H, s), 3.89(3H, s), 3.92(2H, t, J=7.4), 6.78–6.83(2H, m), 7.24–7.48(10H, m) |
| 23 | 87~89 | 0.77(3H, t, J=7.3), 1.08–1.62(4H, m) 2.18(3H, s), 2.55(3H, s), 3.88(3H, s) 3.97(2H, t, J=7.5), 6.81(1H, dd, J=8.6, 2.5), 6.98(1H, d, J=2.5), 7.18 (1H, d, J=8.6), 7.29(2H, d, J=8.5), 7.34(2H, d, J=8.5) |
| 24 | 147~151 | 0.67(3H, t, J=7.3), 1.56(2H, m), 2.19(3H, s), 3.88(3H, s), 3.93(2H, t, J=7.3), 6.92(1H, dd, J=8.6, 2.5), 7.01(1H, d, J=2.5), 7.24(1H, d, J=8.6) 7.49–8.06(9H, m) |

TABLE 7

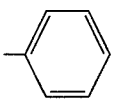

| Example | (R¹)x | R²O— | R³ | R⁶ | n | A | R⁵ |
|---|---|---|---|---|---|---|---|
| 25 | H | 5CH₃O— | —CH₃ | 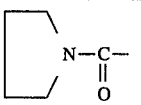 | 0 | —(CH₂)₅— | 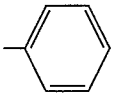 |
| 26 | H | 5CH₃O— | —CH₃ | 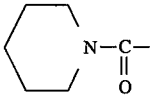 | 0 | —(CH₂)₅— | 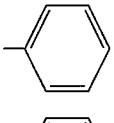 |
| 27 | H | 5CH₃O— | —CH₃ | 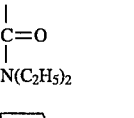 | 0 | —(CH₂)₅— | 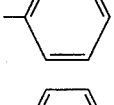 |
| 28 | H | 5CH₃O— | —CH₃ | 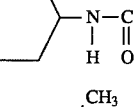 | 0 | —(CH₂)₅— | 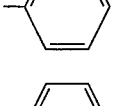 |
| 29 | H | 5CH₃O— | —CH₃ | 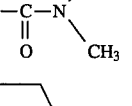 | 0 | —(CH₂)₅— | 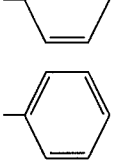 |
| 30 | H | 5CH₃O— | —CH₃ | 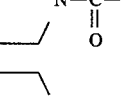 | 0 | —(CH₂)₇— |  |
| 31 | H | 5CH₃O— | —CH₃ | 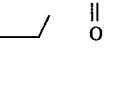 | 0 | —(CH₂)₄— | |

TABLE 7-continued

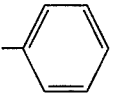

| Example | (R¹) x | R²O— | R³ | R⁶ | n | A | R⁵ |
|---|---|---|---|---|---|---|---|
| 32 | H | 5CH₃O— | —CH₃ | phenyl | 0 | —(CH₂)₄— | —C(=O)—N(CH₃)₂ |
| 33 | H | 5CH₃O— | —CH₃ | phenyl | 0 | —(CH₂)₅— | phenyl-NH—C(=O)— |
| 34 | H | 5CH₃O— | —CH₃ | phenyl | 0 | —(CH₂)₅— | CH(CH₃)₂–NH–C(=O)– |
| 35 | H | 5CH₃O— | —CH₃ | phenyl | 0 | —(CH₂)₅— | cyclohexyl-NH—C(=O)— |
| 36 | H | 5CH₃O— | —CH₃ | phenyl | 0 | —(CH₂)₅— | cycloheptyl-NH—C(=O)— |
| 37 | H | 5CH₃O— | —CH₃ | phenyl | 0 | —CH₂— | phenyl |
| 38 | H | 6CH₃O— | —CH₃ | phenyl | 0 | —(CH₂)₅— | pyrrolidinyl-C(=O)— |
| 39 | 4,6-di-Br | 5CH₃O— | —CH₃ | phenyl | 0 | —CH₂)₅— | pyrrolidinyl-C(=O)— |
| 40 | H | 5CH₃O— | —C₂H₅ | pyridyl | 0 | —(CH₂)₅— | pyrrolidinyl-C(=O)— |
| 41 | H | 5CH₃O— | —CH₃ | cyclohexyl | 0 | —(CH₂)₅— | pyrrolidinyl-C(=O)— |
| 42 | H | 5CH₃O— | —CH₃ | cyclohexyl | 0 | —(CH₂)₅— | —C(=O)—N(CH₃)₂ |
| 43 | H | 5CH₃O— | —CH₃ | —C₂H₅ | 0 | —(CH₂)₅— | pyrrolidinyl-C(=O)— |

TABLE 7-continued
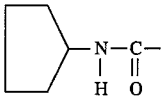
| Example | (R¹) x | R²O— | R³ | R⁶ | n | A | R⁵ |
|---|---|---|---|---|---|---|---|
| 44 | H | 5CH$_3$O— | —CH$_3$ | —C$_2$H$_5$ | 0 | —(CH$_2$)$_5$— | 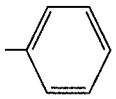 |
| 45 | H | 5CH$_3$O— | —CH$_3$ | —C$_2$H$_5$ | 0 | —CH$_2$— | 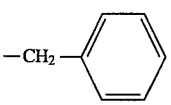 |
| 46 | H | 5CH$_3$O— | —CH$_3$ | —CH$_2$–C$_6$H$_5$ | 0 | —(CH$_2$)$_5$— | 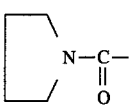 |
| 47 | H | 5CH$_3$O— | —CH$_3$ | —CH$_2$–C$_6$H$_5$ | 0 | —(CH$_2$)$_5$— | 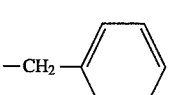 |
| 48 | H | 5CH$_3$O— | —CH$_3$ | C$_2$H$_5$ | 0 | —(CH$_2$)$_5$— | 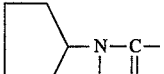 |
| 49 | H | 5CH$_3$O— | —CH$_3$ | (CH$_2$)$_3$–CH$_3$ | 0 | —(CH$_2$)$_5$— | 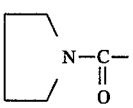 |
| 50 | H | 5CH$_3$O— | —CH$_3$ | (CH$_2$)$_3$–CH$_3$ | 0 | —(CH$_2$)$_5$— |  |
| 51 | H | 5CH$_3$O— | —CH$_3$ | 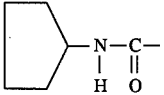 | 0 | —(CH$_2$)$_5$— |  |
| 52 | H | 5CH$_3$O— | —CH$_3$ | 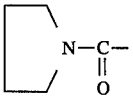 | 0 | —(CH$_2$)$_5$— | 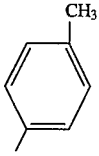 |
| 53 | H | 5CH$_3$O— | —CH$_3$ | 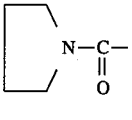 | 0 | —(CH$_2$)$_5$— | 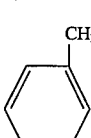 |

TABLE 7-continued

| Example | (R¹) x | R²O— | R³ | R⁶ | n | A | R⁵ |
|---|---|---|---|---|---|---|---|
| 54 | H | 5CH₃O— | —CH₃ | 4-methylphenyl (p-tolyl) | 0 | —(CH₂)₅— | cyclobutyl-NH-C(=O)— |
| 55 | H | 5CH₃O— | —CH₃ | 2-pyridyl | 0 | —(CH₂)₅— | cyclopropyl-NH-C(=O)— |
| 56 | H | 5CH₃O— | —CH₃ | 2-pyridyl | 0 | —(CH₂)₅— | cyclobutyl-NH-C(=O)— |
| 57 | 6Br— | 5CH₃O— | —Br | phenyl | 0 | —CH₂— | phenyl |
| 58 | H | 5CH₃O— | —CH₃ | —CH₃ | 0 | —CH₂— | phenyl |
| 59 | H | 5CH₃O— | —CH₃ | —CH₃ | 0 | —CH₂— | 4-methoxyphenyl |
| 60 | H | 5CH₃O— | —CH₃ | —CH₃ | 0 | —(CH₂)₅— | pyrrolidin-1-yl-C(=O)— |
| 61 | H | 5CH₃O— | —CH₃ | —CH₃ | 0 | —(CH₂)₅— | piperidin-1-yl-C(=O)— |
| 62 | H | 5CH₃O— | —CH₃ | —CH₃ | 0 | —(CH₂)₅— | —C(=O)—N(CH₃)₂ |
| 63 | H | 5CH₃O— | —CH₃ | —CH₃ | 0 | —(CH₂)₅— | cyclopentyl-NH-C(=O)— |
| 64 | H | 5CH₃O— | —CH₃ | —CH₃ | 0 | —(CH₂)₇— | pyrrolidin-1-yl-C(=O)— |

TABLE 7-continued

| Example | (R¹) x | R²O— | R³ | R⁶ | n | A | R⁵ |
|---|---|---|---|---|---|---|---|
| 65 | H | 5CH₃O— | —CH₃ | —CH₃ | 0 | —(CH₂)₅— | pyrrolidine N–C(=O)– with C(=O)OC(CH₃)₃ substituent |
| 66 | H | 5CH₃O— | —CH₃ | —CH₃ | 0 | —(CH₂)₅— | indanyl–NH–C(=O)– |
| 67 | H | 5CH₃O— | —CH₃ | —CH₃ | 0 | —(CH₂)₅— | —C(=O)—N(H)—C₂H₅ |
| 68 | H | 5CH₃O— | —CH₃ | —CH₃ | 0 | —(CH₂)₅— | —C(=O)—N(H)—CH(CH₃)₂ |
| 69 | H | 5CH₃O— | —CH₃ | —CH₃ | 0 | —(CH₂)₅— | —C(=O)—N(H)—CH₃ |
| 70 | H | 5CH₃O— | —CH₃ | —CH₃ | 0 | —(CH₂)₅— | cyclobutyl–NH–C(=O)– |
| 71 | H | 5CH₃O— | —CH₃ | —CH₃ | 0 | —(CH₂)₅— | cyclopropyl–NH–C(=O)– |
| 72 | H | 5CH₃O— | —CH₃ | —CH₃ | 0 | —(CH₂)₅— | —C(=O)—N(H)—SO₂—CH₃ |
| 73 | H | 5CH₃O— | —CH₃ | —CH₃ | 0 | —(CH₂)₅— | —C(=O)—N(H)—C(CH₃)₃ |
| 74 | H | 5CH₃O— | —CH₃ | —CH₃ | 0 | —(CH₂)₅— | —C(=O)—N(CH₂-phenyl)—CH(CH₃)₂ |

TABLE 7-continued

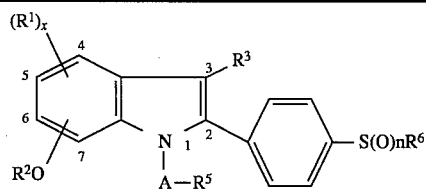

| Example | (R¹) x | R²O— | R³ | R⁶ | n | A | R⁵ |
|---|---|---|---|---|---|---|---|
| 75 | H | 5CH₃O— | —CH₃ | —CH₃ | 0 | —(CH₂)₅— | —C(=O)—NH—CH(CH₃)—C₂H₅ |
| 76 | H | 5CH₃O— | —CH₃ | —CH₃ | 0 | —(CH₂)₅— | —C(=O)—NH—CH₂—CH(CH₃)₂ |
| 77 | H | 5CH₃O— | —CH₃ | —CH₃ | 0 | —(CH₂)₅— | —C(=O)—N(H)—CH₂—C₆H₅ |
| 78 | H | 5CH₃O— | —CH₃ | —CH₃ | 0 | —(CH₂)₅— | —C(=O)—NH—C(CH₃)₂—CH₂CH₃ |
| 79 | H | 5CH₃O— | —CH₃ | —C₆H₅ | 2 | —(CH₂)₅— | piperidine-N—C(=O)— |
| 80 | H | 5CH₃O— | —CH₃ | —C₆H₅ | 0 | —(CH₂)₅— | —C(=O)—OC₂H₅ |
| 81 | H | 5CH₃O— | —CH₃ | —CH₂—C₆H₅ | 0 | —(CH₂)₅— | —C(=O)—OC₂H₅ |
| 82 | H | 5CH₃O— | —CH₃ | —C₂H₅ | 0 | —(CH₂)₅— | —C(=O)—OC₂H₅ |
| 83 | 6-Br | 5CH₃O— | Br | —C₆H₅ | 0 | —(CH₂)₅— | —C(=O)—OC₂H₅ |

TABLE 8

| No. | mp (°C.) | ¹H-NMR(CDCl₃) |
|---|---|---|
| 25 | Oil | 1.14–1.94(10H, m), 2.11(2H, t, J=7.2) 2.20(3H, s), 3.30(2H, t, J=6.7), 3.42(2H, t, J=6.7), 3.88(3H, s) 3.99(2H, t, J=7.4), 6.88(1H, dd, J= |

TABLE 8-continued

| No. | mp (°C.) | $^1$H-NMR(CDCl$_3$) |
|---|---|---|
| 26 | Oil | 8.9, 2.5), 7.01(1H, d, J=2.5), 7.20–7.49(10H, m) |
| 26 | Oil | 1.11–1.65(12H, m), 2.17(2H, J=7.97), 2.20(3H, s), 3.27–3.52(4H, m), 3.88(3H, s), 6.88(1H, dd, J=8.6, 2.3), 7.01(1H, d, J=2.3), 7.20–7.50(10H, m) |
| 27 | Oil | 1.04–1.19(8H, m), 1.48–1.60(4H, m), 2.15(2H, t, J=7.4), 2.20(3H, s), 3.16–3.37(4H, m), 3.88(3H, s), 3.99(2H, t, J=7.4), 6.88(1H, dd, J=8.9, 2.3), 7.01(1H, d, J=2.3), 7.20–7.50(10H, m) |
| 28 | 104–107 | 1.08–1.73(10H, m), 1.97(2H, t, J=7.2) 2.20(3H, s), 3.88(3H, s), 3.98(2H, t, J=7.2), 4.10–4.18(1H, m), 5.2–5.4 (1H, m), 6.88(1H, dd, J=8.8, 2.7), 7.0 (1H, d, J=2.7), 7.21(1H, d, J=8.8), 7.25–7.49(9H, m) |
| 29 | Oil | 1.11–1.67(6H, m), 2.16(2H, t, J=7.2), 2.20(3H, s), 2.91(6H, s), 3.88(3H, s), 3.99(2H, t, J=7.4), 6.88(1H, dd, J=8.8, 2.4), 7.01(1H, d, J=2.4), 7.22(1H, d, J=8.8), 7.25–7.49(9H, m) |
| 30 | Oil | 1.04–1.96(14H, m), 2.17(2H, t, J=4.0), 3.36(2H, t, J=6.7), 3.44(2H, t, J=6.7), 3.88(3H, s), 4.00(2H, t, J=7.4), 6.88(1H, dd, J=8.9, 2.4), 7.02 (1H, d, J=2.4), 7.22(1H, d, J=8.9), 7.25–7.49(9H, m) |
| 31 | Oil | 1.25–2.04(10H, m), 2.20(3H, s), 3.20(2H, t, J=6.7), 3.39(2H, t, J=6.7) 3.88(3H, s), 4.01(2H, t, J=7.3), 6.88(1H, dd, J=8.7, 2.5), 7.01(1H, d, J=2.5), 7.21–7.50(10H, m) |
| 32 | Oil | 1.37–1.67(8H, m), 2.06(2H, t, J=7.3), 2.20(3H, s), 2.84(3H, s), 2.87(3H, s), 3.88(3H, s), 4.01(2H, t, J=7.3), 6.88(1H, dd, J=8.9, 2.3), 7.01(1H, d, J=2.3), 7.21–7.50(10H, m) |
| 33 | Oil | 1.07–1.63(6H, m), 2.15(2H, t, J=7.4), 2.19(3H, s), 3.87(3H, s), 3.99(2H, t, J=7.3), 4.12(1H, q, J=7.1), 6.88(1H, dd. J=8.8, 2.4), 7.01(1H, d, J=2.4), 7.07–7.48(15H, m) |
| 34 | 101–102 | 1.09(3H, s), 1.11(3H, s), 1.40–1.64 (6H, m), 1.96(2H, t, J=7.5), 2.20(3H, s), 3.88(3H, s), 3.95–4.10(3H, m), 5.07–5.12(1H, br), 6.88(1H, dd, J=8.8, 2.3), 7.01(1H, d, J=2.3), 7.22 (1H, d, J=8.8), 7.25–7.50(9H, m) |
| 35 | 79–80 | 0.96–1.88(16H, m), 1.97(2H, t, J=7.4) 2.20(3H, s ), 3.6–3.78(1H, m), 3.88(3H, s), 3.98(2H, t, J=7.4), 5.08–5.15(1H, br), 6.88(1H, dd, J=8.8, 2.5), 7.01(1H, d, J=2.5), 7.21 (1H, d, J=8.8), 7.25–7.50(9H, m) |
| 36 | 74–76 | 1.05–1.90(18H, m), 1.96(2H, t, J=7.4), 2.20(3H, s), 3.88(3H, s), 3.82–3.95(1H, m), 3.98(2H, t, J=7.3), 5.20–5.26(1H, brs), 6.88(1H, dd, J=8.8, 2.4), 7.01(1H, d, J=2.4), 7.21(1H, d, J=8.9), 7.25–7.50(9H, m) |
| 37 | Oil | 2.28(3H, s), 3.88(3H, s), 5.18(2H, s), 6.81(1H, dd, J=8.9, 2.5), 6.92(1H, d, J=2.5), 7.02–7.45(15H, m) |
| 38 | Oil | 1.19–1.93(10H, m), 2.11(2H, t, J=7.3) 2.20(3H, s), 3.30(2H, t, J=6.6), 3.42(2H, t, J=6.6), 3.89(3H, t, J=7.3) 3.98(2H, t, J=7.3), 6.78–6.82(2H, m), 7.25–7.49(10H, m) |
| 39 | Oil | 1.06–1.98(10H, m), 2.12(2H, t, J=7.47), 2.39(3H, s), 3.28–3.48(4H, m) 3.88(3H, s), 7.19–7.51(10H, m) |
| 40 | Oil | 1.18(3H, t, J=7.2), 1.12–1.94(10H, m) 2.11(2H, t, J=7.2), 2.63(2H, q, J=7.2) 3.29(2H, t, J=6.8), 3.42(2H, t, J=6.8) 3.88(3H, s), 3.95(2H, t, J=7.2), |

TABLE 8-continued

| No. | mp (°C.) | $^1$H-NMR(CDCl$_3$) |
|---|---|---|
| | | 6.88(1H, dd, J=8.8, 2.4), 7.07(1H, d, J=2.4), 7.22–7.49(10H, m) |
| 41 | Oil | 1.14–2.17(22H, m), 2.21(3H, s), 3.20–3.45(5H, m), 3.89(3H, s), 3.99(2H, t, J=7.4), 6.88(1H, dd, J=8.7, 2.5), 7.02(1H, d, J=2.5), 7.21–7.46(5H, m) |
| 42 | Oil | 1.14–2.18(18H, m), 2.21(3H, s), 2.90(3H, s), 2.91(3H, s), 3.10–3.30 (1H, m), 3.89(3H, s), 3.99(2H, t, J=7.5), 6.88(1H, dd, J=8.9, 2.4), 7.02 (1H, d, J=2.4), 7.21–7.29(3H, m), 7.45(2H, d, J=8.2) |
| 43 | Oil | 1.14–1.93(10H, m), 2.11(2H, t, J=7.4) 2.20(3H, s), 3.03(2H, q, J=7.4), 3.29(2H, t, J=6.8), 3.42(2H, t, J=6.8) 3.96(3H, s), 3.99(2H, t, J=7.4), 6.79(1H, dd, J=8.7, 2.3), 7.02(1H, d, J=2.3), 7.23(1H, d, J=8.7), 7.27(1H, d, J=8.6), 7.36(1H, d, J=8.6) |
| 44 | 95–98 | 1.05–2.02(16H, m), 1.39(3H, t, J=7.3) 2.20(3H, s), 3.03(2H, q, J=7.4), 3.89(3H, s), 3.93(2H, t, J=7.4), 4.15(1H, q, J=7.1), 5.24–5.28(1H, br) 6.88(1H, dd, J=8.8, 2.4), 7.02(1H, d, J=2.4), 7.22(1H, d, J=8.9), 7.27(2H, d, J=8.5), 7.39(2H, d, J=8.5) |
| 45 | 93–94 | 1.35(3H, t, J=7.3), 2.28(3H, s), 2.98(2H, q, J=7.3), 3.88(3H, s), 5.19(2H, s), 6.81(1H, dd, J=8.6, 2.1) 6.93–7.30(11H, m) |
| 46 | Oil | 1.07–1.98(10H, m), 2.10(2H, t, J=7.5) 2.19(3H, s, 3.29(2H, t, J=6.6), 3.42(2H, t, J=6.6), 3.89(3H, s), 3.97(2H, t, J=7.5), 4.20(2H, s), 6.88(1H, dd, J=8.8, 2.4), 7.01(1H, d, J=2.4), 7.20–7.40(10H, m) |
| 47 | Oil | 1.04–1.80(14H, m), 1.97(2H, t, J=7.5) 2.19(3H, s), 3.89(3H, s), 3.97(2H, t, J=7.6), 4.05–4.24(1H, m), 4.20(2H, s) 6.88(1H, dd, J=8.7, 2.5), 7.01(1H, d, J=2.5), 7.19–7.40(10H, m) |
| 48 | Oil | 1.03–1.96(17H, m), 2.18(2H, t, J=7.9) 2.20(3H, s), 3.03(2H, q, J=7.3), 3.34–3.46(4H, m), 3.89(3H, s), 3.96 (2H, t, J=7.5), 6.88(1H, dd, J=8.9, 2.4), 7.02(1H, d, J=2.4), 7.22(1H, J=8.9), 7.28(1H, d, J=8.7), 7.40(1H, d, J=8.7) |
| 49 | 90–92 | 0.96(3H, t, J=7.3), 1.05–1.99(20H, m) 2.20(3H, s), 3.00(2H, t, J=7.3), 3.89(3H, s), 3.98(2H, t, J=7.4), 4.15(1H, q, J=7.0), 5.20–5.26(1H, br) 6.88(1H, dd, J=8.9, 2.4), 6.99(1H, d, J=2.4), 7.21(1H, d, J=8.9), 7.26(1H, d, J=8.2), 7.38(1H, d, J=8.2) |
| 50 | Oil | 0.96(3H, t, J=7.3), 1.15–1.97(14H, m) 2.11(2H, t, 7.4), 2.20(3H, s), 3.00 (2H, t, J=7.3), 3.29(2H, t, J=6.7), 3.42(2H, t, J=6.7), 3.89(3H, s), 3.99 (2H, t, J=7.4), 6.88(1H, dd, J=8.7, 2.5), 7.02(1H, d, J=2.5), 7.23(1H, d, J=8.7), 7.27(2H, d, J=8.5), 7.38(2H, d, J=8.5) |
| 51 | Oil | 1.08–1.94(10H, m), 2.11(2H, t, J=7.5) 2.19(3H, s), 2.38(3H, s), 3.30(2H, t, J=6.6), 3.42(2H, t, J=6.6), 3.88(3H, s), 3.98(2H, t, J=7.3), 6.88(1H, dd, J=8.7, 2.4), 7.01(1H, d, J=2.4), 7.19–7.44(9H, m) |
| 52 | Oil | 1.03–1.83(14H, m), 1.97(2H, t, J=7.5) 2.19(3H, s), 2.38(3H, s), 3.88(3H, s), 3.97(2H, t, J=7.3), 4.05–4.26(1H, m), 6.87(1H, dd, J=8.9, 2.4), 7.01(1H, d, J=2.4), 7.19–7.44(9H, m) |
| 53 | Oil | 0.43–1.72(6H, m), 1.94(2H, t, J=7.5) 2.18(3H, s), 2.38(3H, s), 2.6–2.75 (1H, m), 3.38–3.42(1H, m), 3.88(3H, |

TABLE 8-continued

| No. | mp (°C.) | $^1$H-NMR(CDCl$_3$) |
|---|---|---|
| | | s), 3.97(2H, t, J=7.3), 6.88(1H, dd, J=8.8, 2.4), 7.01(1H, d, J=2.4), 7.19 (1H, d, J=8.8), 7.21–7.44(8H, m) |
| 54 | Oil | 1.04–1.84(12H, m), 1.95(2H, t, J=7.5) 2.19(3H, s), 2.38(3H, s), 3.88(3H, s), 3.97(2H, t, J=7.3), 4.34(1H, m), 5.36–5.45(1H, br), 6.88(1H, dd, J= 8.7, 2.5), 7.01(1H, d, J=2.5), 7.19– 7.44(9H, m) |
| 55 | Oil | 0.41–1.78(10H, m), 1.95(2H, t, J=7.6) 2.24(3H, s), 2.63(1H, s), 3.89(3H, s), 4.03(2H, t, J=7.6), 5.53(1H, s), 6.90(1H, dd, J=8.9, 2.3), 7.03–7.11 (3H, m), 7.24(1H, d, J=8.9), 7.40(2H, d, J=7.9), 7.56(1H, ddd, J=7.8, 7.8, 1.9), 7.67(2H, d, J=7.9), 8.47(1H, d, J=4.6) |
| 56 | Oil | 1.01–1.86(10H, m), 1.96(2H, t, J= 7.6), 2.24(3H, s), 3.90(3H, s), 4.03 (2H, t, J=7.6), 4.34(1H, m), 5.55(1H, m), 6.90(1H, dd, J=8.9, 2.3), 7.04– 7.14(3H, m), 7.23(1H, d, J=8.9), 7.41 (2H, d, J=7.9), 7.56(1H, ddd, J=7.8, 7.8, 1.9), 7.67(2H, d, J=7.9), 8.48 (1H, d, J=4.6) |
| 57 | Amorphous | 3.97(3H, s), 5.21(2H, s), 6.87–7.49(16H, m) |
| 58 | 114–115 | 2.23(3H, s), 2.55(3H, s), 3.89(3H, s), 5.20(2H, s), 6.77(1H, dd, J=8.6, 2.5), 6.98–7.32(11H, m) |
| 59 | 106–108 | 2.27(3H, s), 2.51(3H, s), 3.74(3H, s), 3.88(3H, s), 5.12(2H, s), 6.73–7.29(11H, m) |
| 60 | 96–99 | 1.10–1.94(10H, m), 2.08(2H, t, J=7.8) 2.17(3H, s), 2.52(3H, 2), 3.27(2H, t, J=6.8), 3.39(2H, t, J=6.8), 3.86(3H, s), 3.96(2H, t, J=7.2), 6.85(1H, dd, J=8.8, 2.4), 6.97(1H, d, J=2.4), 7.18– 7.32(5H, m) |
| 61 | Oil | 1.12–1.92(12H, m), 2.16(2H, t, J=7.4) 2.20(3H, s), 2.55(3H, s), 3.29(2H, t, J=5.6), 3.49(2H, t, J=5.6), 3.89(3H, s), 3.98(2H, t, J=7.2), 6.88(1H, dd, J=8.8, 2.4), 7.02(1H, d, J=2.4), 7.22 (1H, d, J=8.8), 7.26–7.35(4H, m) |
| 62 | Oil | 1.11–1.61(6H, m), 2.16(2H, t, J=8.0), 2.20(3H, s), 2.55(3H, s), 2.90(3H, s), 2.91(3H, s), 3.89(3H, s), 3.99(2H, t, J=7.6), 6.88(1H, dd, J=8.8, 2.4), 7.02(1H, d, J=2.4), 7.22(1H, d, J=8.8) 7.25–7.35(4H, m) |
| 63 | 100–102 | 1.06–2.02(16H, m), 2.20(3H, s), 3.88(3H, s), 3.98(2H, t, J=7.3), 4.15(1H, q, J=7.1), 5.22–5.26(1H, brs), 6.88(1H, dd, J=8.7, 2.4), 7.01 (1H, d, J=2.4), 7.21(1H, d, J=8.7), 7.25–7.49(9H, m) |
| 64 | Oil | 1.04–1.96(14H, m), 2.17(2H, t, J=4.0) 2.20(3H, s), 2.55(3H, s), 3.36(2H, t, J=6.8), 3.44(2H, t, J=6.8), 3.89(3H, s), 3.96(2H, t, J=7.4), 6.88(1H, dd, J=8.8, 2.4), 7.02(1H, d, J=2.4), 7.23 (1H, d, J=8.8), 7.28(2H, d, J=8.7), 7.35(2H, d, J=8.7) |
| 65 | Oil | 1.16–2.14(12H, m), 1.44, 1.42(9H, each s), 2.19(3H, s), 2.55(3H, s), 3.30–3.63(1H, m), 3.88(3H, s), 3.97(2H, t, J=7.4), 6.88(1H, dd, J=8.6, 2.3), 7.01 (1H, d, J=2.3), 7.23(1H, d, J=8.6), 7.28(2H, d, J=8.3), 7.34(2H, d, J=8.3) |
| 66 | 110–111 | 1.14–1.83(8H, m), 2.04(2H, t, J=7.5) 2.19(3H, s), 2.52(3H, s), 2.78–3.04 (2H, m), 3.88(3H, s), 3.99(2H, t, J= 7.3), 5.4–5.64(2H, m), 6.87(1H, dd, J=8.7, 2.4), 7.00(1H, d, J=2.4), 7.19 7.35(9H, m) |
| 67 | 87– | 1.09(3H, t, J=7.3), 1.10–1.62(6H, m), |
| 88 | | 1.97(2H, t, J=7.5), 2.20(3H, s), 2.55 (3H, s), 3.23(2H, q, J=7.3), 3.98(3H, s), 3.99(2H, t, J=7.3), 5.27(1H, brs), 6.88(1H, dd, J=8.6, 2.5), 7.02(1H, d, J=2.5), 7.28(2H, d, J=8.7), 7.35(2H, d, J=8.7) |
| 68 | 91–93 | 1.09(3H, s), 1.11(3H, s), 1.07–1.65 (6H, m), 1.96(2H, t, J=7.5), 2.20(3H, s) 2.55(3H, s), 3.89(3H, s), 3.96–4.07(3H, m), 5.08–5.16(1H, br), 6.88 (1H, dd, J=8.9, 2.5), 7.02(1H, d, J= 2.5), 7.22(1H, d, J=8.9), 7.28(2H, d, J=8.9), 7.35(2H, d, J=8.7) |
| 69 | 103–105 | 1.03–1.63(6H, m), 1.97(2H, t, J=7.6), 2.20(3H, s), 2.55(3H, s), 2.74(3H, d, J=4.9), 3.89(3H, s), 3.99(2H, t, J= 7.3), 5.25(1H, br, s), 6.88(1H, dd, J= 8.9, 2.4), 7.02(1H, d, J=2.4), 7.22 (1H, d, J=8.9), 7.28(1H, d, J=8.6) 7.35(1H, d, J=8.6) |
| 70 | 154 | 1.10–1.87(12H, m), 1.95(2H, t, J=7.5) 2.19(3H, s), 2.55(3H, s), 3.89(3H, s), 3.98(2H, t, J=7.3), 4.33(1H, m), 5.37–5.48(1H, br), 6.88(1H, dd, J= 8.8, 2.4), 7.02(1H, d, J=2.4), 7.21 (1H, d, J=8.8), 7.27(1H, d, J=8.6), 7.35(1H, d, J=8.6) |
| 71 | Oil | 0.42–1.66(10H, m), 1.94(2H, t, J=7.5) 2.20(3H, s), 2.55(3H, s), 2.6–2.75 (1H, m), 3.89(3H, s), 3.98(2H, t, J= 7.3), 6.88(1H, dd, J=8.7, 2.5), 7.02 (1H, d, J=2.5), 7.21(1H, d, J=8.7), 7.27(2H, d, J=8.4), 7.35(2H, d, J=8.4) |
| 72 | 81–85 | 1.03–1.62(6H, m), 2.11(2H, t, J=7.4) 2.20(3H, s), 2.55(3H, s), 3.22(3H, s), 3.89(3H, s), 4.00(2H, t, J=7.2), 6.89(1H, dd, J=8.7, 2.3), 7.02(1H, d, J=2.3), 7.21(1H, d, J=8.7), 7.28(2H, d, J=8.4), 7.38(2H, d, J=8.4) |
| 73 | Oil | 1.04–1.76(6H, m), 1.30, 1.34(9H, each s) 1.93(2H, t, J=7.5), 2.19(3H, s), 2.55 (3H, s), 3.89(3H, s), 3.97(2H, t, J= 7.3), 5.12(1H, br), 6.88(1H, dd, J= 8.8, 2.5), 7.02(1H, d, J=2.5), 7.22 (1H, d, J=8.8), 7.28(2H, d, J=8.3), 7.33(2H, d, J=8.3) |
| 74 | Oil | 0.98–1.82(12H, m), 2.06(2H, t, J= 7.5), 2.18, 2.20(total 3H, each s), 2.54 (3H, s), 3.89(3H, s), 3.92(2H, t, J= 7.3), 4.36(2H, s), 4.85(1H, q, J=7.0), 6.87(1H, dd, J=8.6, 2.5), 7.01(1H, d, J=2.5), 7.12–7.30(10H, m) |
| 75 | 116–117 | 0.86(3H, t, J=7.4), 1.07(3H, d, J=6.6) 1.05–1.63(8H, m), 1.98(2H, t, J=7.5), 2.20(3H, s), 2.55(3H, s), 3.79–3.92 (1H, m), 3.89(3H, s), 3.98(2H, t, J= 7.3), 4.97–5.08(1H, br), 6.88(1H, dd, J=8.8, 2.5), 7.02(1H, d, J=2.5), 7.22 (1H, d, J=8.8), 7.27(2H, d, J=8.3), 7.35(2H, d, J=8.3) |
| 76 | 87– | 0.86(3H, s), 0.89(3H, s), 1.06–1.80 (7H, m), 2.00(2H, t, J=7.5), 2.20(3H, s), 2.55(3H, s), 3.02(2H, t, J=6.5), 3.89(3H, s), 3.99(2H, t, J=7.4), 5.32 (1H, br), 6.88(1H, dd, J=8.7, 2.5), 7.02(1H, d, J=8.7), 7.22(1H, d, J=8.7), 7.28(2H, d, J=8.2), 7.35(2H, d, J=8.2) |
| 77 | Oil | 1.06–1.72(6H, m), 2.03(2H, t, J=7.6), 2.19(3H, s, 2.53(3H, s), 3.88(3H, s), 3.98(2H, t, J=7.4), 4.39(2H, d, J=6.8) 5.55–5.63(1H, br), 6.87(1H, dd, J= 8.8, 2.4), 7.01(1H, d, J=2.4), 7.18– 7.35(10H, m) |
| 78 | Amorphous | 0.78–1.97(1H, m), 2.20(3H, s), 2.55 (3H, s), 3.89(3H, s), 3.98(2H, t, J= 7.4) 4.97–5.06(1H, br), 6.88(1H, dd, J=8.8, 2.4), 7.02(1H, d, J=2.4), 7.22 |

TABLE 8-continued

| No. | mp (°C.) | $^1$H-NMR(CDCl$_3$) |
|---|---|---|
| 79 | Oil | (1H, d, J=8.8), 7.26–7.36(4H, m) 1.10–1.95(10H, m), 2.10(2H, t, J=7.6) 2.19(3H, s), 3.27–3.46(4H, m), 3.88 (3H, s), 3.97(2H, t, J=7.6), 6.91(1H, dd, J=8.9, 2.5), 7.00(1H, d, J=2.5), 7.24(1H, d, J=8.9), 7.49–7.62(5H, m), 8.01–8.05(4H, m) |
| 80 | Oil | 1.12–1.82(6H, m), 1.22(3H, t, J=7.3), 2.16(2H, t, J=7.6), 2.20(3H, s), 3.89 (3H, s ), 4.01(2H, t, J=7.6), 4.08(2H, q, J=7.3), 6.88(1H, dd, J=8.8, 2.3), 7.02(1H, d, J=2.3), 7.20–7.51(10H, m) |
| 81 | Amorphous | 1.09–1.88(6H, m), 1.22(3H, t, J=7.2), 2.16(2H, t, J=7.6), 2.19(3H, s), 3.89 (3H, s), 3.96(2H, t, J=7.2), 4.12(2H, q, J=7.2), 4.20(2H, s), 6.89(1H, dd, |
| | | J=8.7, 2.5), 7.02(1H, d, J=2.5), 7.23–7.47(10H, m) |
| 82 | Oil | 1.10–1.73(6H, m), 1.22(3H, t, J=7.3), 1.39(3H, t, J=7.4), 2.16(2H, t, J=7.6) 2.20(3H, s), 3.02(2H, q, J=7.4), 3.89 (3H, s), 3.98(2H, t, J=7.6), 4.08(2H, q, J=7.3), 6.89(1H, dd, J=8.7, 2.5), 7.02(1H, d, J=2.5), 7.22(1H, d, J=8.7) 7.27(2H, d, J=8.3), 7.40(2H, d, J=8.3) |
| 83 | Amorphous | 1.10–1.95(6H, m), 1.25(3H, t, J=7.2), 2.15(2H, t, J=7.6), 3.96(3H, s), 4.01 (2H, t, J=7.3), 4.11(2H, q, J=7.2), 7.02(1H, s), 7.31–7.51(10H, m) |

TABLE 9

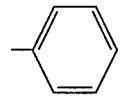

| Example | (R$^1$)x | OH group binding position | R$^3$ | R$^6$ | n | R$^5$ |
|---|---|---|---|---|---|---|
| 84 | H | 5 | H | phenyl | 0 | —CH$_2$H$_5$ |
| 85 | H | 5 | H | phenyl | 0 | —CH$_2$CH$_2$CH$_3$ |
| 86 | H | 5 | —CH$_3$ | phenyl | 0 | —C$_2$H$_5$ |
| 87 | H | 5 | —CH$_3$ | phenyl | 0 | —(CH$_2$)$_3$CH$_3$ |
| 88 | H | 5 | —CH$_3$ | phenyl | 0 | —(CH$_2$)$_5$CH$_3$ |
| 89 | H | 5 | —CH$_3$ | phenyl | 0 | —(CH$_2$)$_9$CH$_3$ |
| 90 | H | 5 | —CH$_3$ | phenyl | 0 | —CH$_2$CH$_2$CH$_3$ |
| 91 | H | 6 | —CH$_3$ | phenyl | 0 | —C$_2$H$_5$ |

TABLE 9-continued

[Structure: indole with (R¹)x at positions 4-7, R³ at position 3, S(O)nR⁶ on phenyl at position 2, R⁵ on N1, HO- attached to benzene ring]

| Example | (R¹)x | OH group binding position | R³ | R⁶ | n | R⁵ |
|---|---|---|---|---|---|---|
| 92 | H | 6 | —CH₃ | —C₆H₅ (phenyl) | 0 | —(CH₂)₂CH₃ |
| 93 | H | 5 | —CH₃ | —CH₃ | 0 | —(CH₂)₃CH₃ |
| 94 | H | 5 | —CH₃ | —C₆H₅ (phenyl) | 2 | —(CH₂)₂CH₃ |
| 95 | H | 5 | —CH₃ | —CH₃ | 0 | H |

TABLE 10

| No. | mp (°C.) | ¹H-NMR(CDCl₃) |
|---|---|---|
| 84 | 127–129 | 1.30(3H, t, J=7.2), 4.14(2H, q, J=7.2) 4.56(1H, s), 6.39(1H, s), 6.81(1H, dd, J=8.7, 2.4), 7.02(1H, d, J=2.4), 7.22–7.48(10H, m) |
| 85 | 140–142 | 0.76(3H, t, J=7.4), 1.70(2H, q, J=7.6) 4.05(2H, t, J=7.6), 4.54(1H, s), 6.38 (1H, d, J=0.7), 6.80(1H, dd, J=8.7, 2.3), 7.02(1H, d, J=2.3), 7.21–7.47 (10H, m) |
| 86 | 122–123 | 1.18(3H, t, J=7.1), 2.17(3H, s), 4.01 2H, q, J=7.1), 4.78(1H, s), 6.80(1H, dd, J=8.7, 2.4), 6.98(1H, d, J=2.4), 17–7.50(10H, m) |
| 87 | 48–49 | 0.75(3H, t, J=7.3), 1.07–1.57(4H, m), 2.16(3H, s), 3.96(2H, t, J=7.6), 4.62 (1H, s), 6.79(1H, dd, J=8.6, 2.3), 6.97(1H, d, J=2.3), 7.18(1H, d, J=8.6) 7.24–7.47(9H, m) |
| 88 | 70–72 | 0.81(3H, t, J=7.1), 1.09–1.59(8H, m), 2.16(3H, s), 3.97(2H, t, J=7.5), 6.79 (1H, dd, J=8.7, 2.4), 6.98(1H, d, J=2.4), 7.19(1H, d, J=8.7), 7.21–7.48 (10H, m) |
| 89 | Oil | 0.87(3H, t, J=7.2), 1.02–1.59((16H, m), 2.16(3H, s), 3.95(2H, t, J=7.2), 6.80(1H, dd, J=8.6, 2.4), 6.97(1H, d, J=2.4), 7.18(1H, d, J=8.6), 7.24–7.48(9H, m) |
| 90 | Oil | 0.71(3H, t, J=7.4), 1.59(2H, q, J=7.4) 2.16(3H, s), 3.92(2H, t, J=7.4), 4.99 (1H, s), 6.80(1H, dd, J=8.6, 2.3), 6.97(1H, d, J=2.3), 7.16–7.49(10H, m) |
| 91 | 91–94 | 1.17(3H, t, J=7.1), 2.20(3H, s), 3.96 (2H, q, J=7.1), 4.82(1H, s), 6.69(1H, dd, J=8.4, 2.2), 6.79(1H, d, J=2.2), 7.24–7.50(10H, m) |
| 92 | Oil | 0.71(3H, t, J=7.3), 1.53–1.61(2H, m), 2.19(3H, s), 3.87(2H, t, J=7.4), 4.90 (1H, s), 6.68(1H, dd, J=8.6, 2.3), 6.78(1H, d, J=2.3), 7.23–7.48(10H, m) |
| 93 | 70–73 | 0.77(3H, t, J=7.3), 1.08–1.61(4H, m), 2.18(3H, s), 2.55(3H, s), 3.96(2H, t, J=7.5), 4.76(1H, brs), 6.80(1H, dd, J=8.7, 2.5), 6.98(1H, d, J=2.5), 7.19 (1H, d, J=8.7), 7.29(2H, d, J=8.6), 7.35(2H, d, J=8.6) |
| 94 | 190–191 | 0.66(3H, t, J=7.3), 1.51–1.63(2H, m), 2.15(3H, s), 3.91(2H, t, J=7.5), 6.84 (1H, dd, J=8.6, 2.3), 6.97(1H, d, J=2.3), 7.19(1H, d, J=8.9), 7.48–7.62 (5H, m), 8.00–8.04(4H, m) |
| 95 | 170–171 | 2.38(3H, s), 2.54(3H, s), 6.77(1H, dd, J=8.6, 2.5), 6.99(1H, d, J=2.5), 7.22 (1H, d, J=8.6), 7.35(2H, d, J=8.2), 7.48(2H, d, J=8.2), 7.84(1H, brs) |

TABLE 11

| Example | (R¹)x | OH group binding position | R³ | R⁶ | n | A | R⁵ |
|---|---|---|---|---|---|---|---|
| 96 | H | 5 | —CH₃ | phenyl | 0 | —(CH₂)₅— | piperidinyl-C(=O)— |
| 97 | H | 5 | —CH₃ | phenyl | 0 | —(CH₂)₅— | piperidinyl-C(=O)— |
| 98 | H | 5 | —CH₃ | phenyl | 0 | —(CH₂)₅— | —C(=O)—N(C₂H₅)₂ |
| 99 | H | 5 | —CH₃ | phenyl | 0 | —(CH₂)₅— | cyclopentyl-NH—C(=O)— |
| 100 | H | 5 | —CH₃ | phenyl | 0 | —(CH₂)₅— | —C(=O)—N(CH₃)₂ |
| 101 | H | 5 | —CH₃ | phenyl | 0 | —(CH₂)₇— | piperidinyl-C(=O)— |
| 102 | H | 5 | —CH₃ | phenyl | 0 | —(CH₂)₄— | piperidinyl-C(=O)— |
| 103 | H | 5 | —CH₃ | phenyl | 0 | —(CH₂)₄— | —C(=O)—N(CH₃)₂ |
| 104 | H | 5 | —CH₃ | phenyl | 0 | —(CH₂)₅— | phenyl-NH—C(=O)— |
| 105 | H | 5 | —CH₃ | phenyl | 0 | —(CH₂)₅— | CH(CH₃)₂-NH—C(=O)— |
| 106 | H | 5 | —CH₃ | phenyl | 0 | —(CH₂)₅— | cyclohexyl-NH—C(=O)— |
| 107 | H | 5 | —CH₃ | phenyl | 0 | —(CH₂)₅— | cycloheptyl-CH—C(=O)— |

TABLE 11-continued

| Example | (R¹)x | OH group binding position | R³ | R⁶ | n | A | R⁵ |
|---|---|---|---|---|---|---|---|
| 108 | H | 5 | —CH₃ | phenyl | 0 | —CH₂— | phenyl |
| 109 | H | 6 | —CH₃ | phenyl | 0 | —(CH₂)₅— | piperidinyl-C(=O)— |
| 110 | H | 5 | —CH₃ | phenyl | 0 | —(CH₂)₅— | piperidinyl-C(=O)— |
| 111 | H | 5 | —C₂H₅ | phenyl | 0 | —(CH₂)₅— | piperidinyl-C(=O)— |
| 112 | H | 5 | —CH₃ | cyclohexyl | 0 | —(CH₂)₅— | piperidinyl-C(=O)— |
| 113 | H | 5 | —CH₃ | cyclohexyl | 0 | —(CH₂)₅— | —C(=O)—N(CH₃)₂ |
| 114 | H | 5 | —CH₃ | —C₂H₅ | 0 | —(CH₂)₅— | piperidinyl-C(=O)— |
| 115 | H | 5 | —CH₃ | —C₂H₅ | 0 | —(CH₂)₅— | cyclopentyl-NH-C(=O)— |
| 116 | H | 5 | —CH₃ | —C₂H₅ | 0 | —CH₂— | phenyl |
| 117 | H | 5 | —CH₃ | —CH₂-phenyl | 0 | (CH₂)₅— | piperidinyl-C(=O)— |
| 118 | H | 5 | —CH₃ | —CH₂-phenyl | 0 | (CH₂)₅— | cyclopentyl-NH-C(=O)— |
| 119 | H | 5 | —CH₃ | —C₂H₅ | 0 | (CH₂)₅— | piperidinyl-C(=O)— |

TABLE 11-continued

Structure: Indole with (R¹)ₓ at positions 4,5,6, HO at position 7, N1 bearing A-R⁵, position 2 bearing phenyl-S(O)nR⁶, position 3 bearing R₃.

| Example | (R¹)x | OH group binding position | R³ | R⁶ | n | A | R⁵ |
|---|---|---|---|---|---|---|---|
| 120 | H | 5 | —CH₃ | —CH(CH₃)(CH₂)₃ (isobutyl-like: —(CH₂)₃ with CH₃ branch) | 0 | —(CH₂)₅— | cyclopentyl-NH-C(=O)- |
| 121 | H | 5 | —CH₃ | —(CH₂)₃CH₃ branched | 0 | —(CH₂)₅— | pyrrolidinyl-N-C(=O)- |
| 122 | H | 6 | —CH₃ | p-tolyl | 0 | —(CH₂)₅— | pyrrolidinyl-N-C(=O)- |
| 123 | H | 5 | —CH₃ | p-tolyl | 0 | —(CH₂)₅— | cyclopentyl-NH-C(=O)- |
| 124 | H | 5 | —CH₃ | p-tolyl | 0 | —(CH₂)₅— | cyclopropyl-NH-C(=O)- |
| 125 | H | 5 | —CH₃ | p-tolyl | 0 | —(CH₂)₅— | cyclobutyl-NH-C(=O)- |
| 126 | H | 5 | —CH₃ | 2-pyridyl | 0 | —(CH₂)₅— | cyclopropyl-NH-C(=O)- |
| 127 | H | 5 | —CH₃ | 2-pyridyl | 0 | —(CH₂)₅— | cyclobutyl-NH-C(=O)- |
| 128 | 6Br | 5 | —Br | phenyl | 0 | —CH₂— | phenyl |
| 129 | H | 5 | —CH₃ | —CH₃ | 0 | —CH₂— | phenyl |

TABLE 11-continued

Structure:

indole with (R¹)ₓ at position 4/5, numbered 3,4,5,6,7 around benzene, N1 with A—R⁵ substituent, position 2 bearing phenyl-S(O)ₙR⁶, position 3 bearing R₃, and HO— at position 7.

| Example | (R¹)x | OH group binding position | R³ | R⁶ | n | A | R⁵ |
|---|---|---|---|---|---|---|---|
| 130 | H | 5 | —CH₃ | —CH₃ | 0 | —CH₂— | 4-hydroxyphenyl |
| 131 | H | 5 | —CH₃ | —CH₃ | 0 | —(CH₂)₅— | pyrrolidin-1-yl-carbonyl (N—C(=O)—) |
| 132 | H | 5 | —CH₃ | —CH₃ | 0 | —(CH₂)₅— | piperidin-1-yl-carbonyl (N—C(=O)—) |
| 133 | H | 5 | —CH₃ | —CH₃ | 0 | —(CH₂)₅— | —C(=O)—N(CH₃)₂ |
| 134 | H | 5 | —CH₃ | —CH₃ | 0 | —(CH₂)₅— | cyclopentyl-NH—C(=O)— |
| 135 | H | 5 | —CH₃ | —CH₃ | 0 | —(CH₂)₇— | pyrrolidin-1-yl-carbonyl (N—C(=O)—) |
| 136 | H | 5 | —CH₃ | —CH₃ | 0 | —(CH₂)₅— | prolyl [pyrrolidin-N-C(=O)— with α-COOH] |
| 137 | H | 5 | —CH₃ | —CH₃ | 0 | —(CH₂)₅— | indan-1-yl-NH—C(=O)— |
| 138 | H | 5 | —CH₃ | —CH₃ | 0 | —(CH₂)₅— | —C(=O)—NH—C₂H₅ |
| 139 | H | 5 | —CH₃ | —CH₃ | 0 | —(CH₂)₅— | —C(=O)—NH—CH(CH₃)₂ |
| 140 | H | 5 | —CH₃ | —CH₃ | 0 | —(CH₂)₅— | —C(=O)—NH—CH₃ |

TABLE 11-continued
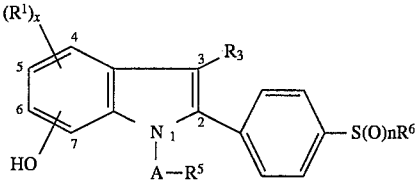
| Example | (R¹)x | OH group binding position | R³ | R⁶ | n | A | R⁵ |
|---|---|---|---|---|---|---|---|
| 141 | H | 5 | —CH₃ | —CH₃ | 0 | —(CH₂)₅— | 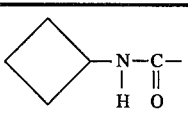 |
| 142 | H | 5 | —CH₃ | —CH₃ | 0 | —(CH₂)₅— | 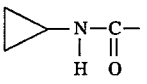 |
| 143 | H | 5 | —CH₃ | —CH₃ | 0 | —(CH₂)₅— | —C(=O)—N(H)—SO₂—CH₃ |
| 144 | H | 5 | —CH₃ | —CH₃ | 0 | —(CH₂)₅— | —C(=O)—N(H)—C(CH₃)₃ |
| 145 | H | 5 | —CH₃ | —CH₃ | 0 | —(CH₂)₅— | 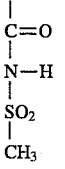 |
| 146 | H | 5 | —CH₃ | —CH₃ | 0 | —(CH₂)₅— | —C(=O)—NH—CH(CH₃)—C₂H₅ |
| 147 | H | 5 | —CH₃ | —CH₃ | 0 | —(CH₂)₅— | —C(=O)—NH—CH₂—CH(CH₃)₂ |
| 148 | H | 5 | —CH₃ | —CH₃ | 0 | —(CH₂)₅— | 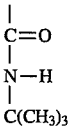 |
| 149 | H | 5 | —CH₃ | —CH₃ | 0 | —(CH₂)₅— | —C(=O)—NH—C(CH₃)₂—C₂H₅ |

TABLE 11-continued

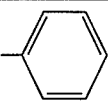

| Example | (R¹)x | OH group binding position | R³ | R⁶ | n | A | R⁵ |
|---|---|---|---|---|---|---|---|
| 150 | H | 5 | —CH₃ | 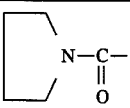 | 0 | —(CH₂)₅— |  |
| 151 | H | 5 | —CH₃ | 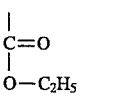 | 0 | —(CH₂)₅— | \|<br>C=O<br>\|<br>O—C₂H₅ |
| 152 | H | 5 | —CH₃ | —CH₂—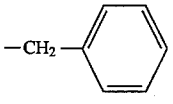 | 0 | —(CH₂)₅— | \|<br>C=O<br>\|<br>O—C₂H₅ |
| 153 | H | 5 | —CH₃ | —C₂H₅ | 0 | —(CH₂)₅— | \|<br>C=O<br>\|<br>O—C₂H₅ |
| 154 | 6Br | 5 | Br | 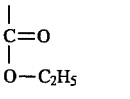 | 0 | —(CH₂)₅— | \|<br>C=O<br>\|<br>O—C₂H₅ |
| 155 | H | 5 | H | 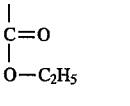 | 0 | —(CH₂)₅— | \|<br>C=O<br>\|<br>O—C₂H₅ |

TABLE 12

| No. | mp (°C.) | ¹H-NMR(CDCl₃) |
|---|---|---|
| 96 | Oil | 1.13–1.94(10H, m), 2.13(2H, t, J=7.6) 2.14(3H, s), 3.31(3H, t, J=6.6), 3.45 (2H, t, J=6.6), 3.92(3H, t, J=7.6) 5.94(1H, brs), 6.81(1H, dd, J=8.6, 2.3), 6.99(1H, d, J=2.3), 7.12–7.49 (10H, m) |
| 97 | 53–55 | 1.12–1.67(12H, m), 2.14(3H, s), 2.18 (2H, t, J=7.3), 3.27–3.57(4H, m), 3.91(2H, t, J=7.5), 5.98(1H, brs), 6.80(1H, dd, J=8.9, 2.3), 6.98(1H, d, J=2.3), 7.13(1H, d, J=8.9), 7.22–7.48(9H, m) |
| 98 | Oil | 1.07–1.14(8H, m), 1.44–1.62(4H, m), 2.14(3H, s), 2.17(2H, t, J=6.9), 3.17–3.40(4H, m), 3.92(1H, t, J=7.6), 5.84(1H, brs), 6.80(1H, dd, J=8.6, 2.3), 6.98(1H, d, J=2.3), 7.13(1H, d, J=8.6), 7.22–7.49(9H, m) |
| 99 | 65–68 | 1.03–1.99(6H, m), 2.13(3H, s), 3.90 (2H, t, J=7.4), 4.13–4.20(1H, m), 5.42(1H, d, J=7.2), 6.80(1H, dd, J= 8.6, 2.4), 6.98(1H, d, J=2.4), 7.11(1H, d, J=8.6), 7.21–7.47(9H, m) |
| 100 | 46–47 | 1.14–1.65(6H, m), 2.06(2H, t, J=7.3) 2.12(3H, s), 2.84(3H, s), 2.90(3H, s) 3.99(2H, t, J=7.2), 6.81(1H, dd, J= 8.7, 2.4), 6.98(1H, d, J=2.4), 7.15 (1H, d, J=8.7), 7.24–7.49(9H, m) |
| 101 | 115–118 | 1.09–1.95(14H, m), 2.15(3H, s), 2.20 (2H, t, J=7.6), 3.35–3.50(4H, m), 3.90(2H, t, J=7.6), 6.82(1H, dd, J= 2.3), 6.99(1H, d, J=2.3), 7.14(1H, d, J=8.6), 7.22–7.48(9H, m) |
| 102 | 200–201 | 1.32–2.07(8H, m), 2.05(3H, s), 3.18–3.41(4H, m), 3.97–4.05(3H, m), 6.70 (1H, dd, J=8.6, 2.3), 6.86(1H, d, J= 2.3), 7.07(1H, d, J=8.6), 7.17(1H, d, J=8.6), 7.21–7.37(9H, m) |
| 103 | 200–201 | 1.40–1.60(4H, m), 2.07(2H, t, J=7.3), 2.12(3H, s), 2.84(3H, s), 2.90(3H, s), 3.99(2H, t, J=7.1), 6.03(1H, brs), 6.80(1H, dd, J=8.7, 2.4), 6.98(1H, d, J=2.4), 7.15(1H, d, J=8.7), 7.24–7.49(9H, m) |
| 104 | 60 | 1.07–1.64(6H, m), 2.15(3H, s), 2.17 (2H, t, J=7.4), 3.98(2H, t, J=7.3), 4.83(1H, brs), 6.78(1H, dd, J=8.7, 2.3), 6.97(1H, d, J=2.3), 7.02–7.49(14H, m) |
| 105 | 60–62 | 1.10(3H, s), 1.12(3H, s), 1.42–1.67 (6H, m), 1.97(2H, t, J=7.5), 2.15(3H, s), 3.92–4.12(3H, m), 5.13–5.18(2H, m), 6.79(1H, dd, J=8.7, 2.4), 6.98(1H, d, J=2.4), 7.15(1H, d, J=8.7), 7.23–7.50(9H, m) |
| 106 | 106– | 1.02–1.93(16H, m), 1.98(2H, t, J=7.4 |

TABLE 12-continued

| No. | mp (°C.) | $^1$H-NMR(CDCl$_3$) |
|---|---|---|
|  | 108 | 2.14(3H, s), 3.83–4.00(3H, m), 5.22–5.26(1H, br), 6.80(1H, dd, J=8.7, 2.3) 7.12(1H, d, J=8.7), 7.21–7.48(9H, m) |
| 107 | 76~78 | 0.98–1.90(18H, m), 2.00(2H, t, J=7.2) 2.15(3H, s), 3.67–3.82(1H, m), 3.95 (2H, t, J=7.3), 5.25–5.30(1H, br), 6.09(1H, br), 6.79(1H, dd, J=8.7, 2.4) 6.97(1H, d, J=2.4), 7.16(1H, d, J=8.7) 7.23–7.50(9H, m) |
| 108 | 181~183 | 2.24(3H, s), 4.53(1H, brs), 5.17(2H, s), 6.71(1H, dd, J=8.9, 2.3), 6.91–7.45(16H, m) |
| 109 | Amorphous | 1.15–1.93(10H, m), 2.18(3H, s), 2.18 (2H, t, J=7.6), 3.33(2H, t, J=6.6), 3.47(2H, t, J=6.6), 3.91(2H, t, J=6.90), 6.74(1H, dd, J=8.2, 1.8), 6.92(1H, d, J=1.8), 7.23–7.84(10H, m) |
| 110 | 60 | 1.07–2.00(10H, m), 2.12(2H, t, J=7.3) 2.37(3H, s), 3.29–3.45(4H, m), 3.89(2H, t, J=5.9)5.77(1H, s), 7.19–7.52(10H, m) |
| 111 | Oil | 114(3H, t, J=7.4), 1.14–1.93(10H, m) 2.14(2H, t, J=7.4), 2.17(3H, s), 2.57 (2H, q, J=7.4), 3.31(2H, t, J=6.8), 3.45(2H, t, J=6.8), 3.89(2H, t, J=7.6) 6.81(1H, dd, J=8.8, 2.7), 7.05(1H, d, J=2.7), 7.14(1H, d, J=8.8), 7.22–7.49(9H, m) |
| 112 | 62~66 | 1.12–2.14(20H, m), 2.17(3H, s), 3.40–3.50(5H, m), 3.94(2H, t, J=7.4), 5.71(1H, brs), 6.81(1H, dd, J=8.6, 2.3), 6.99(1H, d, J=2.3), 7.15(1H, d, J=8.6), 7.25(1H, d, J=7.9), 7.44(1H, d, J=7.9) |
| 113 | 105~107 | 1.13–2.18(20H, m), 2.16(3H, s), 2.924(3H, s), 2.928(3H, s), 3.19–3.28(1H, m), 3.93(2H, t, J=7.4), 5.84(1H, brs), 6.81(1H, dd, J=8.7, 2.4), 6.99(1H, d, J=2.4), 7.15(1H, d, J=8.7), 7.25(2H, d, J=8.3), 7.44(2H, d, J=8.3) |
| 114 | 120~124 | 1.07–1.97(10H, m), 2.10–2.18(2H, m), 2.14(3H, s), 3.02(2H, q, J=7.3), 3.31 (2H, t, J=6.6), 3.46(2H, t, J=6.6), 3.92(2H, t, J=7.4), 6.25(1H, brs), 6.82(1H, dd, J=8.6, 2.3), 7.00(1H, d, J=2.3), 7.13(1H, d, J=8.6), 7.24 (2H, d, J=8.4), 7.37(2H, d, J=8.4) |
| 115 | Oil | 1.04–1.67(17H, m), 1.97(2H, t, J=7.5) 2.17(3H, s), 3.00(2H, J=2.8), 3.03(2H, q, J=7.4) 3.96(2H, t, J=7.4), 4.17(1H, q, J=7.2) 4.81(1H, brs), 5.23(1H, br), 6.79 (1H, dd, J=8.7, 2.4), 6.98(1H, d, J=2.4), 7.17(1H, d, J=8.7), 7.26(2H, d, J=8.3), 7.39(2H, d, J=8.3) |
| 116 | Amorphous | 1.35(3H, t, J=7.3), 2.24(3H, s), 2.98 (2H, q, J=7.4), 4.62(1H, brs), 5.18 (2H, s), 6.71(1H, dd, J=8.6, 2.3), 6.92–7.33(11H, m) |
| 117 | 139~140 | 1.07–1.97(10H m), 2.10–2.15(5H, m), 3.30(2H, t, J=6.6), 3.45(2H, t, J=6.6) 3.90(2H, t, J=7.4) 4.18(2H, s), 6.23(1H, s), 6.82(1H, dd, J=8.7, 2.4), 7.00(1H, d, J=2.4), 7.13(1H, d, J=8.7) 7.19–7.38(9H, m) |
| 118 | Amorphous | 1.02–2.03(16H, m), 2.12(3H, s), 3.86–4.23(4H, m), 5.46–5.52(1H, br), 6.82(1H, dd, J=8.6, 2.3), 7.00(1H, d, J=2.3), 7.12(1H, d, J=8.6), 7.18–7.38(9H, m) |
| 119 | 82~84 | 1.02–1.98(17H, m), 2.15(3H, s), 2.20 (2H, t, J=7.6), 3.02(2H, q, J=7.3), 3.38(2H, t, J=6.6), 3.47(2H, t, J=6.6) 3.90(2H, t, J=5.9), 6.04(1H, brs), 6.82(1H, dd, J=8.7, 2.3), 7.00(1H, d, J=2.3), 7.15(1H, d, J=8.7), 7.24(2H, d, J=8.2), 7.38(2H, d, J=8.2) |
| 120 | Oil | 0.93–2.00(20H, m), 2.15(3H, s), 3.00 (2H, t, J=7.3), 3.92(2H, t, J=7.3), 4.17(1H, q, J=7.1), 5.30–5.36(1H, br), 5.82(1H, brs), 6.80(1H, dd, J=8.7,2.4), 6.99(1H, d, J=2.4), 7.13 (1H, d, J=8.7), 7.23(2H, d, J=8.1), 7.35(2H, d, J=8.1) |
| 121 | 107~109 | 0.92–2.02(19H, m), 2.15(3H, s), 3.00 (2H, t, J=7.3), 3.30(2H, t, J=6.8), 3.42(2H, t, J=6.8), 3.93(2H, t, J=7.3), 5.20–5.25(1H, br), 6.80(1H, dd, J=8.7, 2.4), 6.99(1H, d, J=2.4), 7.13(1H, d, J=8.7), 7.24(2H, d, J=8.2), 7.35(2H, d, J=8.2) |
| 122 | Amorphous | 1.05–1.93(10H, m), 2.11(3H, s), 2.36 (3H, s), 3.28(2H, t, J=6.8), 3.46(2H, t, J=6.8), 3.88(2H, t, J=7.4), 6.82 (1H, dd, J=8.6, 2.5), 7.00(1H, d, J=2.5), 7.09(1H, d, J=8.6), 7.17–7.45 (8H, m) |
| 123 | Amorphous | 1.02–2.03(16H, m), 2.13(3H, s), 2.38 (3H, s), 3.91(2H, t, J=7.3), 4.08–4.24(1H, m), 5.33–5.38(1H, br), 5.98 (1H, brs), 6.79(1H, dd, J=8.7, 2.4), 6.98(1H, d, J=2.4), 7.12(1H, d, J=8.7) 7.18–7.43(8H, m) |
| 124 | Amorphous | 0.40–1.80(10H, m), 1.94(2H, t, J=7.4) 2.13(3H, s), 2.37(3H, s), 2.60–2.75 (1H, m), 3.92(2H, t, J=7.3), 5.52 (1H, br), 5.70–5.90(1H, br), 6.80(1H, dd, J=8.6, 2.4), 6.98(1H, d, J=2.4), 7.12(1H, d, J=8.6), 7.18–7.42(8H, m) |
| 125 | Amorphous | 1.02–1.85(10H, m), 1.95(2H, t, J=7.6), 2.13(3H, s), 2.23–2.35(2H, m), 2.38(3H, s), 3.92(2H, t, J=7.3), 4.27–4.43(1H, m), 5.46–5.63(2H, m), 6.79 (1H, dd, J=8.6, 2.4), 6.97(1H, d, J=2.4), 7.13(1H, d, J=8.6), 7.18–7.43 (8H, m) |
| 126 | Amorphous | 0.38–1.65(10H, m), 1.95(2H, t, J=7.5) 2.18(3H, s), 2.60–2.70(1H, m), 3.98(2H, t, J=7.3), 5.58(2H, br), 6.82(1H, dd, J=8.7, 2.4), 7.00(1H, d, J=2.4), 7.06–8.48(9H, m) |
| 127 | Amorphous | 1.02–1.92(8H, m), 1.96(2H, t, J=7.5), 2.17(3H, s), 2.23–2.34(2H, m), 3.95 (2H, t, J=7.3), 4.27–4.41(1H, m), 5.68–5.76(1H, br), 6.30–6.50(1H, br), 6.82(1H, dd, J=8.6, 2.3), 7.00–7.65(9H, m), 8.46–8.50(1H, m) |
| 128 | Amorphous | 5.18(2H, s), 5.36(1H, s), 6.86–7.48 (16H, m) |
| 129 | 76~79 | 2.27(3H, s),2.54(3H, s), 4.85(1H, s), 5.21(2H, s), 6.75(1H, dd, J=8.6, 2.5), 6.97–7.31(11H, m) |
| 130 | 120~122 | 2.56(3H, s), 3.26(2H, 3.51(2H, s), 3.53(3H, s), 6.34–6.77(6H, m), 7.23–7.36(3H, m), 8.00(2H, d, J=8.4) |
| 131 | 162~164 | 1.12–1.93(10H, m), 2.13(3H, t, J=7.8), 2.14(3H, s), 2.54(3H, s), 3.30 (2H, t, J=6.8), 3.45(2H, t, J=6.8), 3.93(2H, t, J=7.3) 5.30(1H, s), 6.81 (1H, dd, J=8.8, 2.4), 6.94(1H, d, J=2.4), 7.14(1H, d, J=8.8), 7.26(2H, d, J=8.3), 7.33(2H, d, J=8.3) |
| 132 | 95~97 | 1.10–1.94(12H, m), 2.13(2H, J=7.4), 2.14(3H, s), 2.55(3H, s), 3.30 (2H, t, J=6.8)13.44(2H, t, J=6.8), 3.98(2H, t, J=7.3), 5.50(1H, s), 6.81 (1H, dd, J=8.7, 2.4), 6.93(1H, d, J=2.4), 7.13(1H, d, J=8.7), 7.25(2H, d, J=8.2), 7.32(2H, d, J=8.2) |
| 133 | 65~67 | 1.13–1.64(6H, m), 2.05(2H, t, J=7.3), 2.12(3H, s), 2.55(3H, s), 2.83, 2.89 (6H, each s), 3.99(2H, t, J=7.2), 6.81 (1H, dd, J=8.7, 2.4), 6.99(1H, d, J=2.4), 7.14(1H, d, J=8.7), 7.25(2H, |

TABLE 12-continued

| No. | mp (°C.) | ¹H-NMR(CDCl₃) |
|---|---|---|
| 134 | 134–136 | d, J=8.3), 7.44(2H, d, J=8.3) 1.02–1.73(14H, m), 1.98(2H, J=7.6), 2.13(3H, s), 2.53(3H, s), 3.90 (2H, t, J=7.3), 4.10–4.24(1H, m), 5.41(1H, d, J=7.4), 6.24(1H, brs), 6.80(1H, dd, J=8.7, 2.4), 6.99(1H, d, J=2.4), 7.12(1H, d, J=8.7), 7.23 (2H, d, J=8.4), 7.31(2H, d, J=8.4) |
| 135 | 118–120 | 1.09–1.95(14H, m), 2.13–2.23(5H, m), 2.53(3H, s), 3.38(2H, t, J=6.7), 3.48 (2H, t, J=6.7), 3.89(2H, J=7.0), 6.84(1H, dd, J=8.7, 2.3) 7.02 (1H, d, J=2.3), 7.13(1H, d, J=8.7), 7.23(1H, d, J=8.6), 7.31(1H, d, J=8.6) |
| 136 | Amorphous | 1.03–2.10(12H, m), 2.15(3H, s), 2.54 (3H, s), 3.40–3.60(2H, m), 4.16–4.23 (1H, m), 6.79(1H, d, J=2.3), 7.27(2H, d, J=2.6), 7.33(2H, d, J=8.6) |
| 137 | 75–80 | 1.07–1.80(6H, m), 2.04(2H, t, J=7.5), 2.13(3H, s), 2.51(3H, s), 2.75–3.03 (2H, m), 3.94(2H, t, J=7.4), 5.43–5.61(3H, m), 6.78(1H, dd, J=8.7, 2.3), 6.95(1H, d, J=2.3), 7.13(1H, d, J=8.7), 7.21–7.33(9H, m) |
| 138 | 105–107 | 1.03–1.61(9H, m), 1.98(2H, t, J=7.6), 2.15(3H, s), 2.54(3H, s), 3.22–3.40 (2H, m), 3.94(2H, t, J=7.4), 5.28–5.36(1H, m), 6.80(1H, dd, J=8.7, 2.4), 6.98(1H, d, J=2.4), 7.3–4(1H, d, J=8.7), 7.25(2H, d, J=8.4), 7.33(2H, d, J=8.4) |
| 139 | 57–60 | 1.10(3H, s), 1.12(3H, s), 1.04–1.62 (6H, m), 1.97(2H, t, J=7.5), 2.15(3H, s), 2.55(3H, s), 3.94(2H, t, J=7.4), 4.00–4.12(1H, m), 5.10–5.24(2H, m), 6.79(1H, dd, J=8.7, 2.5), 6.98(1H, d, J=2.5), 7.15(1H, d, J=8.7), 7.26(2H, d, J=8.2), 7.33(2H, d, J=8.2) |
| 140 | 122–125 | 1.02–1.59(6H, m), 1.97(2H, t, J=7.6), 2.14(3H, s), 2.54(3H, s), 2.75(3H, d, J=4.8), 3.93(2H, t, J=7.3), 5.32–5.42(1H, br), 5.84(1H, brs), 6.80(1H, dd, J=8.7, 2.4), 6.99(1H, d, J=2.4), 7.13(1H, d, J=8.7), 7.24(2H, d, J=8.3), 7.33(2H, d, J=8.3) |
| 141 | 154 | 1.04–1.88(10H, m), 1.96(2H, t, J=7.5) 2.14(3H, s), 2.24–2.37(2H, m), 2.55 (3H, s), 3.93(2H, J=7.3), 4.29–4.43(1H, m), 5.47–5.57(2H, m), 6.80 (1H, dd, J=8.7, 2.4), 6.99(1H, d, J=2.4), 7.14(1H, d, J=8.7), 7.25(2H, d, J=8.4), 7.33(2H, d, J=8.4) |
| 142 | Amorphous | 1.40–1.80(10H, m), 1.94(2H, t, J=7.6), 2.15(3H, s), 2.54(3H, s), 2.60–2.70(1H, m), 395(2H, t, J=7.3), 5.45–5.52(1H, br), 5.50–5.60(1H, br), 6.80(1H, dd, J=8.7, 2.4), 6.99(1H, d, J=2.4), 7.15(1H, d, J=8.7), 7.26(2H, d, J=8.3), 7.33(2H, d, J=8.3) |
| 143 | 80–84 | 1.03–1.62(6H, m), 2.08(2H, t, J=7.4), 2.15(3H, s), 2.55(3H, s), 3.21(3H, s), 3.98(2H, J=7.0), 6.79(1H, dd, J=8.7, 2.4), 6.98(1H, d, J=2.4), 7.17 (1H, d, J=8.7), 7.26(2H, d, J=8.6), 7.35(2H, d, J=8.6) |
| 144 | Amorphous | 1.03–1.60(6H, m), 1.31(9H, s), 1.94 (2H, t, J=7.5), 2.14(3H, s), 2.54(3H, s), 3.93(2H, t, J=7.3), 5.17(1H, br), 5.60(1H, brs), 6.77(1H, dd, J=8.7, 2.4), 6.99(1H, d, J=2.4), 7.12(1H, d, J=8.7), 7.23(2H, d, J=8.2), 7.33(2H, |
| 145 | Amorphous | d, J=8.2) 0.97–1.65(12H, m), 2.07(2H, t, J=7.3) 2.13, 2.15(3H, each s), 2.53(3H, s), 3.84–4.17(3H, m), 4.37, 4.51(total 2H, each s), 5.39(1H, brs), 6.75–7.34(12H, m) |
| 146 | Amorphous | 0.87(3H, t, J=7.4), 1.08(3H, d, J=6.4) 1.08–1.63(8H, m), 1.99(2H, t, J=7.5), 2.15(3H, s), 2.55(3H, s), 3.85–4.00 (3H, m), 5.05–5.13(1H, br), 5.29(1H, brs), 6.79(1H, dd, J=8.7, 2.4), 6.98 (1H, d, J=2.4), 7.15(1H, d, J=8.7), 7.26(2H, d, J=8.4), 7.34(2H, d, J=8.4) |
| 147 | Amorphous | 0.88(6H, d, J=6.6), 1.05–1.82(7H, m), 2.01(2H, t, J=7.5), 2.15(3H, s), 2.54 (3H, s), 3.04(3H, t, J=6.4), 3.94(2H, t, J=7.3), 5.35–5.43(1H, br), 5.50 (1H, brs), 6.79(1H, dd, J=8.7, 2.4), 7.14(1H, d, J=8.7), 7.25(2H, d, J=8.3) 7.33(2H, d, J=8.3) |
| 148 | 127–129 | 1.10–1.63(6H, m), 2.03(2H, t, J=7.6), 2.14(3H, s), 2.53(3H, s), 3.95(2H, t, J=7.3), 4.93(2H, d, J=5.8), 5.01(1H, bs), 5.61(1H, bs), 6.78(1H, dd, J=8.7, 2.4), 6.96(1H, d, J=2.4), 7.15(1H, d, J=8.7), 7.21–7.36(9H, m) |
| 149 | Amorphous | 0.77–1.90(17H, m), 1.96(2H, t, J=7.5), 2.13(3H, s), 2.54(3H, s), 3.91 (2H, t, J=7.1), 5.11(1H, brs), 6.38 (1H, brs), 6.81(1H, dd, J=8.6, 2.4), 7.00(1H, d, J=2.4), 7.13(1H, d, J=8.6), 7.24(2H, d, J=8.5), 7.32(2H, d, J=8.5) |
| 150 | 106–107 | 1.10–2.11(12H, m), 2.13(3H, s), 3.29–3.47(4H, m), 3.93(2H, t, J=6.9), 5.49(1H, s), 6.85(1H, dd, J=8.9, 2.5), 6.98(1H, d, J=2.5), 7.15–8.04(10H, m) |
| 151 | 78–79 | 1.07–1.64(6H, m), 1.22(3H, J=7.2), 2.16(3H, s),2.16(2H, J=7.4), 3.97(2H, t, J=7.4), 4.09(2H, q, J=7.2), 4.70(1H, brs), 6.79(1H, dd, J=8.7, 2.5), 6.97(1H, d, J=2.5), 7.17 (1H, d, J=8.7), 7.24–7.50(9H, m) |
| 152 | 88–90 | 1.04–1.62(6H, m), 1.22(3H, t, J=7.2), 2.15(3H, s), 2.16(2H, t, J=7.4), 3.94 (2H, t, J=7.4), 4.09(2H, J=7.2), 4.19(2H, s), 4.78(1H, s), 6.79(1H, dd, J=8.7, 2.3), 6.97(1H, d, J=2.3), 7.17 (1H, d, J=8.7), 7.21–7.40(9H, m) |
| 153 | Amorphous | 1.04–1.62(6H, m), 1.22(3H, J=7.2), 1.38(3H, t, J=7.4), 2.15(3H, s), 2.16 (2H, t, J=7.5), 3.02(2H, q, J=7.3), 3.95(2H, t, J=7.4), 4.10(2H, q, J=7.2), 5.15(1H, s), 6.79(1H, dd, J=8.7, 2.4), 6.97(1H, d, J=2.4), 7.16(1H, d, J=8.7), 7.26(2H, d, J=8.3), 7.39 (2H, d, J=8.3) |
| 154 | Amorphous | 1.04–1.64(6H, m), 1.22(3H, q, J=7.1), 2.17(2H, t, J=7.3), 3.97(2H, t, J=7.4), 4.09(2H, q, J=7.1), 5.46(1H, s), 7.17(1H, s), 7.25–7.53(10H, m) |
| 155 | 127–129 | 11–1.72(6H, m), 1.22(3H, t, J=7.1), 2.18(2H, t, J=7.4), 4.05–4.15(4H, m), 4.73(1H, brs), 6.37(1H, s ), 6.80(1H, dd, J=8.7, 2.4), 7.02(1H, d, J=2.4), 7.20(1H, d, J=8.4), 7.30–7.47(9H, m) |

TABLE 13

[Structure: indole with R²O at position 4/5/6/7, R³ at position 3, phenyl-SR⁶ at position 2, and N1 substituted with -CH₂-A-N(R¹¹)(R¹²)]

| Example | R²O— | R³ | R⁶ | A | R¹¹ | R¹² | salt |
|---------|------|-----|-----|------|------|------|------|
| 156 | 5-OH | CH₃ | phenyl | —(CH₂)₅— | —(CH₂)₄— | | — |
| 157 | 5-OH | CH₃ | phenyl | —(CH₂)₅— | —(CH₂)₅— | | — |
| 158 | 5-OH | CH₃ | phenyl | —(CH₂)₅— | —C₂H₅ | —C₂H₅ | — |
| 159 | 5-OH | CH₃ | phenyl | —(CH₂)₅— | cyclopentyl | H | — |
| 160 | 5-OH | CH₃ | phenyl | —(CH₂)₅— | phenyl | H | — |
| 161 | 5-OH | CH₃ | phenyl | —(CH₂)₅— | —CH(CH₃)₂ | H | — |
| 162 | 5-OH | CH₃ | phenyl | —(CH₂)₅— | cyclohexyl | H | ½H₂SO₄ |
| 163 | 6-OH | CH₃ | phenyl | —(CH₂)₅— | —(CH₂)₄— | | — |
| 164 | 5-OH | CH₃ | —(CH₂)₃CH₃ | —(CH₂)₅— | cyclohexyl | H | ½H₂SO₄ |
| 165 | 5-OH | CH₃ | 4-methylphenyl | —(CH₂)₅— | cyclopentyl | H | — |
| 166 | 5-OH | CH₃ | 4-methylphenyl | —(CH₂)₅— | cyclopropyl | H | — |

TABLE 13-continued

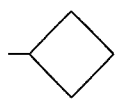

| Example | R²O— | R³ | R⁶ | A | R¹¹ | R¹² | salt |
|---|---|---|---|---|---|---|---|
| 167 | 5-OH | CH₃ | -C₆H₄-CH₃ (p-tolyl) | —(CH₂)₅— | cyclobutyl | H | — |
| 168 | 5-OH | CH₃ | 2-pyridyl | —(CH₂)₅— | cyclopropyl | H | — |
| 169 | 5-OH | CH₃ | 2-pyridyl | —(CH₂)₅— | cyclobutyl | H | — |
| 170 | 5-OH | CH₃ | C₂H₅ | —(CH₂)₅— | cyclopentyl | H | — |
| 171 | 5-OH | CH₃ | CH₃ | —(CH₂)₅— | —(CH₂)₄— | | — |
| 172 | 5-OH | CH₃ | CH₃ | —(CH₂)₅— | cyclopentyl | H | ½H₂SO₄ |
| 173 | 5-OH | CH₃ | CH₃ | —(CH₂)₅— | C₂H₅ | H | — |
| 174 | 5-OH | CH₃ | CH₃ | —(CH₂)₅— | —CH(CH₃)₂ | H | — |
| 175 | 5-OH | CH₃ | CH₃ | —(CH₂)₅— | cyclobutyl | H | — |
| 176 | 5-OH | CH₃ | CH₃ | —(CH₂)₅— | cyclopropyl | H | — |
| 177 | 5-OH | CH₃ | CH₃ | —(CH₂)₅— | —CH(CH₃)₂ | —CH₂—C₆H₅ | — |
| 178 | 5-OH | CH₃ | CH₃ | —(CH₂)₅— | —C(CH₃)₃ | H | — |
| 179 | 5-OH | CH₃ | CH₃ | —(CH₂)₅— | CH(CH₃)(C₂H₅) | H | — |
| 180 | 5-OH | CH₃ | CH₃ | —(CH₂)₅— | CH₂CH(CH₃)₂ | H | — |

TABLE 13-continued

[Structure: indole ring with positions labeled 1-7, $R_2O$ at position 4/5, $R^3$ at position 3, phenyl-$SR^6$ at position 2, and $R^{11}-N(R^{12})-CH_2-A-$ at N1]

| Example | $R^2O-$ | $R^3$ | $R^6$ | A | $R^{11}$ | $R^{12}$ | salt |
|---|---|---|---|---|---|---|---|
| 181 | 5-OH | $CH_3$ | $CH_3$ | $-(CH_2)_5-$ | $-CH_2-$phenyl | H | — |
| 182 | 5-OH | $CH_3$ | $CH_3$ | $-(CH_2)_5-$ | $-C(CH_3)_2-CH_2-CH_3$ | H | — |

TABLE 14

| No. | mp (°C.) | $^1$H-NMR |
|---|---|---|
| 156 | Amorphous | 1.07–1.85(12H, m), 2.14(3H, s), 2.41–2.65(6H, m), 3.90(2H, t, J=7.3), 6.77(1H, dd, J=8.6, 2.3), 6.94(1H, d, J=2.3), 7.12(1H, d, J=8.6), 7.21–7.48(9H, m) [CDCl$_3$] |
| 157 | 80–84 | 1.06–1.61(14H, m), 2.13(3H, s), 2.19–2.40(6H, m), 3.87(2H, t, J=7.1), 6.70–6.76(1H, m), 6.81(1H, dd, J=8.9, 2.3), 6.99(1H, d, J=2.3), 7.90–7.49(10H, m) [CDCl$_3$] |
| 158 | 98–104 | 1.00–1.56(14H, m), 2.15(3H, s), 2.64–2.70(2H, m), 2.95–3.03(4H, m), 3.92(2H, t, J=7.1), 6.89–7.49(12H, m) [CDCl$_3$] |
| 159 | 110 | 1.02–1.93(16H, m), 2.13(3H, s), 2.54(3H, t, J=7.2), 3.04–3.10(1H, m), 3.77–3.90(2H, br), 3.88(2H, t, J=7.4) 6.76(1H, dd, J=8.8, 2.1), 6.94(1H, d, J=2.1), 7.11(1H, d, J=8.8), 7.22–7.46(9H, m) [CDCl$_3$] |
| 160 | Amorphous | 1.06–1.72(8H, m), 2.17(3H, s), 2.99(2H, t, J=7.1), 3.97(2H, t, J=7.3), 6.54–7.49(17H, m) [CDCl$_3$] |
| 161 | 77–90 | 1.06(3H, s), 1.08(3H, s), 1.03–1.60(8H, m), 2.14(3H, s), 2.52(2H, t, J=7.2), 2.73–2.86(1H, m), 3.91(2H, t, J=7.1), 4.12(1H, q, J=7.1), 6.77(1H, dd, J=8.6, 2.3), 6.94(1H, d, J=2.3), 7.13(1H, d, J=8.6), 7.22–7.48(9H, m) [CDCl$_3$] |
| 162 | 133–137 | 1.03–2.07(20H, m), 2.17(3H, s), 2.72(2H, t, J=7.7), 3.00–3.12(1H, m), 3.99(2H, t, J=7.2), 6.81(1H, dd, J=8.7, 2.4), 6.97(1H, d, J=2.4), 7.17(1H, d, J=8.7), 7.26–7.49(9H, m) [CDCl$_3$+CD$_3$OD] |
| 163 | Oil | 1.15–1.81(12H, m), 2.18(3H, s), 2.38–2.54(6H, m), 3.85(2H, t, J=7.4), 6.66–6.74(2H, m), 7.22–7.48(10H, m) [CDCl$_3$] |
| 164 | 134–139 | 0.93–2.12(25H, m), 2.16(3H, s), 2.72(2H, t, J=7.7), 3.01(2H, t, J=7.1), 2.28–2.41(1H, m), 3.98(2H,t, J=7.2), 6.81(1H, dd, J=8.7, 2.9), 6.97(6H, d J=2.4), 7.17(1H, d, J=8.7), 7.27(2H, d, J=8.5), 7.39(2H, d, J=8.5) [CDCl$_3$+CD$_3$OD] |
| 165 | 74–77 | 1.00–1.92(16H, m), 2.13(3H, s), 2.37(3H, s), 2.51(3H, s), 2.98–3.20(4H, m) 3.89(2H, t, J=7.3), 6.75(1H, dd, J=8.6, 2.4), 6.93(1H, d, J=2.4), 7.12(1H, d, J=8.6), 7.18–7.34(6H, m), 7.41(2H, d, J=8.2) [CDCl$_3$] |
| 166 | 62–64 | 0.38–1.60(12H, m), 2.05–2.12(1H, m), 2.13(3H, s), 2.37(3H, s), 2.61(2H, t, J=7.3), 3.48(2H, br), 3.91(3H, t, J=7.4), 6.75(1H, dd, J=8.7, 2.4), 6.93(1H, d, J=2.4), 7.13(1H, d, J=8.7) 7.18–7.29(6H, m), 7.41(2H, d, J=8.1) [CDCl$_3$] |
| 167 | 97–100 | 1.00–1.80(14H, m), 2.12(3H, s), 2.37(3H, s), 2.44(2H, t, J=7.3), 3.18–3.30(1H, m), 3.88(2H, t, J=7.3), 3.85–4.13(2H, br), 6.75(1H, dd, J=8.6, 2.3), 6.92(1H, d, J=2.3), 7.11(1H, d, J=8.6), 7.17–7.29(6H, m), 7.38(2H, d, J=8.2) [CDCl$_3$] |
| 168 | Amorphous | 0.34–1.61(12H, m), 2.05–2.20(5H, m), 2.54–2.64(2H, m), 3.82–4.02(2H, m), 6.74–8.49(11H, m) [CDCl$_3$] |
| 169 | Amorphous | 0.97–1.82(14H, m), 2.15(3H, s), 2.09–2.18(2H, m), 2.44(2H, t, J=7.3), 3.20–3.50(4H, m), 3.93(2H, t, J=7.4), 6.77(1H, dd, J=8.6, 2.4), 6.96(1H, d, J=2.4), 7.14(1H, d, J=8.6), 7.32–8.49(8H, m) [CDCl$_3$] |
| 170 | 109–110 | 1.02–2.03(16H, m), 1.37(3H, t, J=7.3), 2.14(3H, s), 3.01(2H, q, J=7.3) 3.90(2H, t, J=7.3), 4.09–4.23(1H, m) 5.42(1H, d, J=7.6), 6.31(1H, brs), 6.80(6H, dd, J=8.6), 6.99(1H, d, J=2.3), 7.11(1H, d, J=8.7), 7.23(2H, d, J=8.3), 7.36(2H, d, J=8.3) [CDCl$_3$] |
| 171 | 107–111 | 1.07–1.83(12H, m), 2.17(3H, s), 2.33–2.5(6H, m), 2.56(3H, s), 3.37(1H, s) 3.98(2H, t, J=7.2), 6.81(1H, dd, J=8.4, 2.0), 6.97(1H, d, J=2.0), 7.18(1H, d, J=8.4), 7.27–7.67(4H, m) [CDCl$_3$] |
| 172 | 169–172 | 1.01–2.12(16H, m), 2.16(3H, s), 2.56(3H, s), 2.73(2H, t, J=7.7), 3.99(2H, t, J=7.3), 6.80(1H, dd, J=8.7, 2.4), 6.97(1H, d, J=2.4), 7.17(1H, d, J=8.7) 7.28(1H, d, J=8.4), 7.36(1H, d, J=8.4) |

TABLE 14-continued

| No. | mp (°C.) | ¹H-NMR |
|---|---|---|
| 173 | Oil | [CCDl₃+CD₃OD] 1.00–1.61(8H, m), 1.30(3H, t, J=7.3) 2.16(3H, s), 2.56(3H, s), 2.70(2H, t, J=8.0), 2.97(2H, q, J=7.3), 3.99(2H, t, J=7.2), 7.17–7.39(7H, m) [CDCl₃] |
| 174 | 82~85 | 1.02–1.62(8H, m), 1.06(3H, s), 1.08 (3H, s), 2.14(3H, s), 2.51(2H, J=7.4), 2.54(3H, s), 2.83–2.94(3H, m), 3.92(2H, t, J=7.4), 6.76(6H, dd, J=8.6, 2.4), 6.95(1H, d, J=2.4), 7.14 (1H, d, J=8.6), 7.25(2H, d, J=8.4), 7.33(2H, d, J=8.4) [CDCl₃] |
| 175 | 97~99 | 1.00–1.78(14H, m), 2.14(3H, s), 2.15–2.27(2H, m), 2.44(2H, t, J=7.3), 2.54(3H, s), 3.18–3.30(1H, m), 3.74 (2H, br), 3.90(2H, J=7.4), 6.76 (1H, dd, J=8.6, 2.3), 6.97(1H, d, J=2.3), 7.13(1H, d, J=8.6), 7.24(2H, d, J=8.4), 7.32(2H, d, J=8.4) [CDCl₃] |
| 176 | 88~91 | 0.36–1.61(12H, m), 2.06–2.12(1H, m), 2.15(3H, s), 2.54(3H, s), 2.60(2H, t, J=7.3), 2.90(2H, br), 3.93(2H, t, J=7.3), 6.76(1H, dd, J=8.7-2.4), 6.95 (1H, d, J=2.4), 7.15(1H, d, J=8.7), 7.26(2H, d, J=8.6), 7.33(2H, d, J=8.6) |
| 177 | 83~86 | 0.90–1.57(14H, m), 2.15(3H, s), 2.26–2.37(2H, m), 2.54(3H, s), 2.87–3.02 (1H, br), 3.54(2H, brs), 3.91(3H, t, J=7.4), 6.79(1H, dd, J=8.7, 2.5), 6.97(1H, d, J=2.5), 7.15(1H, d, J=8.7), 7.23–7.34(9H, m) |
| 178 | 133~135 | 1.03–1.57(8H, m), 1.13(9H, s), 2.13 (3H, s), 2.47–2.53(5H, m), 3.80–3.94 (4H, m), 6.77(1H, dd, J=8.7, 2.3), 6.94(1H, d, J=2.3), 7.11(1H, d, J=8.7), 7.23(2H, d, J=8.3), 7.31(2H, d, J=8.3) |
| 179 | 65~68 | 0.88(3H, t, J=7.5), 1.03–1.62(9H, m) 1.05(3H, d, J=6.4), 2.14(3H, s), 2.44–2.62(5H, m), 2.87–3.18(3H, br), 3.91(2H, t, J=7.3), 6.76(1H, dd, J=8.7, 2.3), 6.94(1H, d, J=2.3), 7.13 (1H, d, J=8.7), 7.25(2H, d, J=8.4), 7.33(2H, d, J=8.4) |
| 180 | Amorphous | 0.90(6H, d, J=6.8), 1.00–1.89(9H, m) 2.13(3H, s), 2.43(2H, d, J=6.9), 2.47–2.57(5H, m), 3.61–3.92(2H, br), 3.90(2H, t, J=7.3), 6.76(1H, dd, J=8.6, 2.4), 6.92(1H, d, J=2.4), 7.12 (1H, d, J=8.6), 7.24(2H, d, J=8.3), 7.32(2H, d, J=8.3) |
| 181 | 94~97 | 1.07–1.75(6H, m), 2.03(2H, t, J=7.6) 2.14(3H, s), 2.53(3H, s), 3.95(2H, t, J=7.3), 4.40(2H, d, J=5.8), 5.56–5.62(1H, br), 6.78(1H, dd, J=8.7, 2.4), 6.96(1H, d, J=2.4), 7.15(1H, d, J=8.7), 7.22–7.34(9H, m) |
| 182 | 117~119 | 0.82(3H, t, J=7.5), 1.04(6H, s), 1.04–1.61(10H, m), 2.14(3H, s), 2.42(2H, t, J=7.3), 2.54(3H, s), 3.00–3.35(2H, br), 3.91(2H, t, J=7.3), 6.76(1H, dd, J=8.7, 2.3), 6.95(1H, d, J=2.3), 7.13 (1H, d, J=8.7), 7.24(2H, d, J=8.2), 7.33(2H, d, J=8.2) |

TABLE 15

| Example | R² | R³ | R⁶ | m | A | R⁵ |
|---|---|---|---|---|---|---|
| 195 | —CH₃ | H | phenyl | 0 | — | 4-(2-piperidinoethoxy)benzoyl |
| 196 | —CH₃ | H | phenyl | 0 | — | 4-(2-pyrrolidinoethoxy)benzoyl |
| 197 | —CH₃ | H | phenyl | 0 | — | 4-(2-dimethylaminoethoxy)benzoyl |
| 198 | —CH₃ | H | phenyl | 0 | — | 4-(3-pyrrolidinopropoxy)benzoyl |
| 199 | —CH₃ | H | phenyl | 0 | — | 4-(3-piperidinopropoxy)benzoyl |

TABLE 15-continued
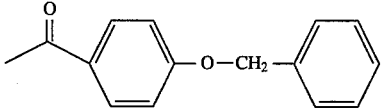
| Example | R² | R³ | R⁶ | m | A | R⁵ |
|---|---|---|---|---|---|---|
| 200 | —CH₃ | H | —C₂H₅ | 0 | — |  |
| 201 | —CH₃ | H | 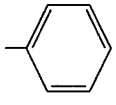 | 0 | — | 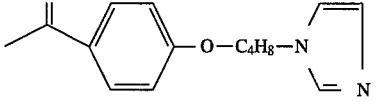 |
| 202 | —CH₃ | H |  | 0 | — | 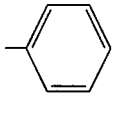 |
| 203 | —CH₃ | H | 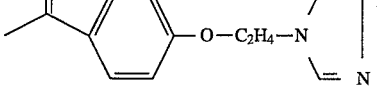 | 0 | — |  |
| 204 | —CH₃ | H | 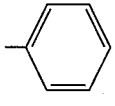 | 0 | — | 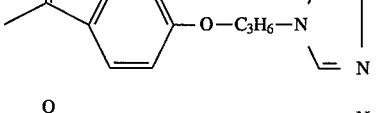 |
| 205 | —CH₃ | —CH₃ |  | 0 | — | 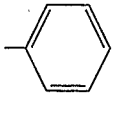 |
| 206 | —CH₃ | H | 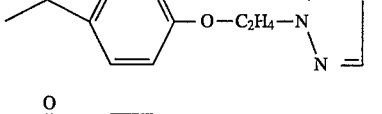 | 0 | — | 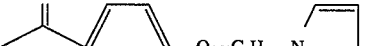 |
| 207 | —CH₃ | —CH₃ | —CH₃ | 0 | — | 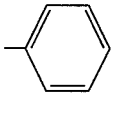 |
| 208 | —CH₃ | —CH₃ | —CH₃ | 0 | — | 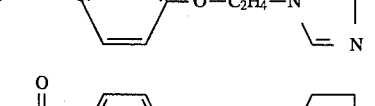 |
| 209 | —CH₃ | —CH₃ | —CH₃ | 0 | — | 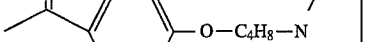 |
| 210 | —CH₃ | —CH₃ | —C₂H₅ | 0 | — | 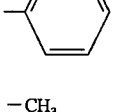 |

TABLE 15-continued
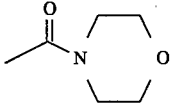
| Example | R² | R³ | R⁶ | m | A | R⁵ |
|---|---|---|---|---|---|---|
| 211 | —CH₃ | —CH₃ | —CH₃ | 1 | —(CH₂)₇— | 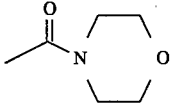 |
| 212 | —CH₃ | H | 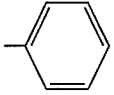 | 1 | —(CH₂)₃— | 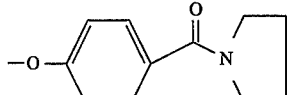 |
| 213 | —CH₃ | H | 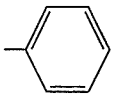 | 1 | —(CH₂)₃— | 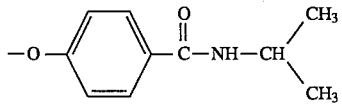 |
| 214 | —CH₃ | —CH₃ | —CH₃ | 1 | —(CH₂)₇— | 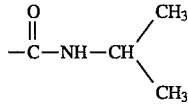 |
| 215 | —CH₃ | —CH₃ | —CH₃ | 1 | —(CH₂)₁₁— | 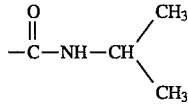 |
| 216 | —CH₃ | —CH₃ | —CH₃ | 1 | —(CH₂)₁₀— | 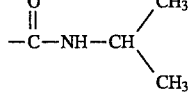 |
| 217 | —CH₃ | —CH₃ | —CH₃ | 1 | —(CH₂)₁₀— | 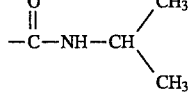 |
| 218 | —CH₃ | —CH₃ | —CH₃ | 1 | —(CH₂)₁₁— | 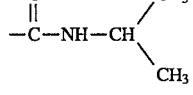 |
| 219 | —CH₃ | —CH₃ | —CH₃ | 1 | —(CH₂)₇— | 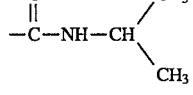 |
| 220 | —CH₃ | —CH₃ | —CH₃ | 1 | —(CH₂)₇— | 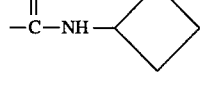 |
| 221 | —CH₃ | —CH₃ | —CH₃ | 1 | —(CH₂)₇— | —C(=O)—NH—C(CH₃)₃ |
| 222 | —CH₃ | —CH₃ | —CH₃ | 1 | —(CH₂)₇— | 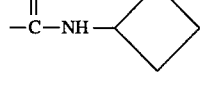 |

TABLE 15-continued

![Structure: indole with R2O at 5-position, R3 at 3-position, 2-position bears phenyl-S-R6, N substituted with (A)m-R5]

| Example | R² | R³ | R⁶ | m | A | R⁵ |
|---|---|---|---|---|---|---|
| 223 | —CH₃ | H | —C₂H₅ | 1 | —(CH₂)₇— | —C(=O)—NH—CH(CH₃)₂ |
| 224 | —CH₃ | H | —C₂H₅ | 1 | —(CH₂)₃— | —O—C₆H₄—C(=O)—N(pyrrolidine) |
| 225 | —CH₃ | H | —C₂H₅ | 1 | —(CH₂)₃— | —O—C₆H₄—C(=O)—NH—CH(CH₃)₂ |
| 226 | —CH₃ | H | —CH₃ | 1 | —CH₂— | —C₆H₄—C(=O)—N(pyrrolidine) |
| 227 | —CH₃ | H | —C₂H₅ | 1 | —CH₂— | —C₆H₄—C(=O)—N(pyrrolidine) |
| 228 | —CH₃ | H | —C₆H₅ | 1 | —(CH₂)₅— | —C(=O)—NH—CH(CH₃)₂ |
| 229 | —CH₃ | —CH₃ | —CH₃ | 1 | —CH₂— | —C₆H₄(m-OCH₃) |
| 230 | —CH₃ | —CH₃ | —CH₃ | 1 | —CH₂— | —C₆H₄(p-OCH₃) |
| 231 | —CH₃ | —CH₃ | —CH₃ | 1 | —(CH₂)₅— | —C(=O)—N(thiazolidine) |

TABLE 16

| No. | mp (°C.) | ¹H-NMR(CDCl₃) |
|---|---|---|
| 195 | Oil | 1.4–1.5(2H, m), 1.5–1.7(4H, m), 2.4–2.6(4H, m), 2.76(2H, t, J=6.1), 3.87(3H, s), 4.11(2H, t, J=6.1), 6.70(1H, s), 6.79(2H, d, J=8.9), 6.86(1H, dd, J=9.1, 2.5), 7.08(1H, d, J=2.5), 7.1–7.3(9H, m), 7.50(1H, d, J=9.1), 7.60(2H, d, J=8.9) |
| 196 | Oil | 1.7–1.9(4H, m), 2.6–2.7(4H, m), 2.90(2H, t, J=5.9), 3.87(3H, s), 4.11(2H, t, J=5.9), 6.70(1H, s), 6.80(2H, d, J=8.8), 6.86(1H, dd, J=9.1, 2.6), 7.08 (1H, d, J=2.6), 7.1–7.4(9H, m), 7.50(1H, d, J=9.1), 7.60(2H, d, J=8.8) |
| 197 | 85–86 | 2.33(6H, s), 2.72(2H, t, J=5.8), 3.87(3H, s), 4.07(2H, t, J=5.8), 6.71(1H, s), 6.80(2H, d, J=8.9), 6.86(1H, dd, J=8.9, 2.6), 7.08(1H, d, J=2.6), 7.1–7.3(9H, m), 7.49(1H, d, J=8.9), 7.60(2H, d, J=8.9) |
| 198 | 95–98 | 1.8–1.9(2H, m), 2.0–2.1(2H, m), 2.6–2.7(4H, m), 2.7–2.8(2H, m), 3.87(3H, s), 4.05(2H, t, J=6.3), 6.70(1H, s), |

TABLE 16-continued

| No. | mp (°C.) | $^1$H-NMR(CDCl$_3$) |
|---|---|---|
|  |  | 6.78(2H, d, J=8.9), 6.86(1H, dd, J=8.9, 2.3), 7.08(1H, d, J=2.3), 7.1–7.3(9H, m), 7.51(1H, d, J=8.9), 7.59(2H, d, J=8.9) |
| 199 |  | 1.4–1.5(2H, m), 1.5–1.7(4H, m), 1.9–2.1(2H, m), 2.4–2.6(6H, m), 3.87(3H, s), 4.02(2H, t, J=6.2), 6.70(1H, s), 6.77(2H, d, J=8.9), 6.86(1H, dd, J=8.9, 2.5), 7.07(1H, d, J=2.5), 7.1–7.4(9H, m), 7.51(1H, d, J=8.9), 7.59(2H, d, J=8.9) |
| 200 | 99–102 | 1.24(3H, t, J=7.4), 2.88(2H, q, J=7.4) 3.87(3H, s), 5.04(2H, s), 6.68(1H, s), 6.8–6.9(3H, m), 7.07(1H, d, J=2.5), 7.13(2H, d, J=8.4), 7.20(2H, d, J=8.4) 7.3–7.5(5H, m), 7.51(1H, d, J=8.9), 7.60(2H, d, J=8.9) |
| 201 | 125–126 | 1.7–1.8(2H, m), 1.9–2.0(2H, m), 3.87 (3H, s), 3.9–4.0(4H, m), 6.70(1H, s), 6.75(2H, d, J=8.9), 6.86(1H, dd, J=8.9, 2.5), 6.92(1H, d, J=2.5), 7.08 (2H, d, J=2.0), 7.1–7.3(9H, m), 7.48 (1H, s), 7.52(1H, d, J=8.9), 7.59(2H, d, J=8.9) |
| 202 | 135–138 | 3.86(3H, s), 4.22(2H, t, J=4.9), 4.34 (2H, t, J=4.9), 6.70(1H, s), 6.75(2H, d, J=9.0), 6.86(1H, dd, J=9.0, 2.7), 7.0–7.3(10H, m), 7.48(1H, d, J=9.0), 7.58(1H, s), 7.61(1H, d, J=9.0) |
| 203 | 130–133 | 2.2–2.3(2H, m), 3.87(3H, s ), 3.92(2H, t, J=6.2), 4.17(2H, t, J=6.2), 6.71 (1H, s), 6.76(2H, d, J=8.9), 6.87(1H, dd, J=8.9, 2.3), 7.08(2H, d, J=2.3), 7.1–7.3(11H, m), 7.48(1H, s), 7.52 (1H, d, J=8.9), 7.61(2H, d, J=8.9) |
| 204 |  | 3.86(3H, s ), 4.35(2H, t, J=5.0), 4.56 (2H, t, J=5.0), 6.70(1H, s), 6.74(2H, d, J=8.9), 6.86(1H, dd, J=9.2, 2.6), 7.07(1H, d, J=2.6), 7.1–7.3(9H, m), 7.48(1H, d, J=9.2), 7.59(2H, d, J=8.9) 7.96 (1H, s), 8.17(1H, s) |
| 205 | 65–68 | 2.28(3H, s), 3.89(3H, s), 4.2–4.4(4H, m), 6.73(2H, d, J =8.7), 6.8–7.4(11H, m), 7.49(1H, d, J =8.7), 7.54(2H, d, J=8.7) |
| 206 | 61–65 | 1.7–1.9(4H, m), 1.9–2.0(4H, m), 2.7–2.9(2H, m), 3.86(3H, s), 3.99(2H, t, J=5.4), 6.71(1H, s), 6.76(2H, d, J=8.9), 6.86(1H, dd, J=8.9, 2.5), 7.08 (1H, d, J=2.5), 7.1–7.4(9H, m), 7.50 (1H, d, J=8.9), 7.60(2H, d, J=8.9) |
| 207 | Oil | 2.27(3H, s), 2.32(6H, s), 2.43(3H, s), 2.71(2H, t, J=5.6), 3.89(3H, s), 4.04 (2H, t, J=5.6), 6.77(2H, d, J=8.7), 6.83(1H, dd, J=8.9, 2.3), 7.00(1H, d, J=2.3), 7.09–7.20(4H, m), 7.38(1H, d, J=8.7), 7.57(2H, d, J=8.9) |
| 208 | Oil | 1.35–1.52(2H, m), 1.53–1.67(4H, m), 2.28(3H, s), 2.43–2.56(4H, m), 2.76 (2H, t, J=6.0), 3.89(3H, s), 4.10(2H, t, J=6.0), 6.77(2H, d, J=8.7), 6.84 (1H, dd, J=9.0, 2.5), 7.01(1H, d, J=2.5), 7.11(2H, d, J=8.5), 7.16(2H, d, J=8.5), 7.39(1H, d, J=9.0), 7.58(2H, d, J=8.7) |
| 209 | Oil | 1.72–1.88(4H, m), 2.27(3H, s), 2.43 (3H, s), 2.55–2.70(4H, m), 2.89(2H, t, J=6.1), 3.89(3H, s), 4.11(2H, t, J=6.1), 6.84(1H, dd, J=8.9, 2.6), 7.01 (1H, d, J=2.6), 7.11(2H, d, J=8.6), 7.16(2H, d, J=8.6), 7.39(1H, d, J=8.6), 7.58(2H, d, J=8.6) |
| 210 | Oil | 1.24(3H, t, J=7.3), 1.40–1.54(2H, m), 1.54–1.70(4H, m), 2.28(3H, s), 2.44–2.58(4H, m), 2.75(2H, t, J=6.1), 2.88 (2H, q, J=7.3), 3.89(3H, s), 4.08(2H, t, J=6.1), 6.73(2H, d, J=8.9), 6.86 |

TABLE 16-continued

| No. | mp (°C.) | $^1$H-NMR(CDCl$_3$) |
|---|---|---|
|  |  | (1H, dd, J=8.9, 2.3), 7.02(1H, d, J=2.3), 7.13(2H, d, J=8.9), 7.17(2H, d, J=8.9), 7.49(1H, d, J=8.9), 7.54(2H, d, J=8.9) |
| 211 | Oil | 1.0–1.3(6H, m), 1.5–1.7(4H, m), 2.19 (3H, s), 2.2–2.3(2H, m), 2.55(3H, s), 3.4–3.5(2H, m), 3.6–3.8(6H, m), 3.88 (3H, s), 3.9–4.1(2H, m), 6.88(1H, dd, J=8.9, 2.4), 7.02(1H, d, J=2.4), 7.22 (1H, d, J=8.9), 7.3–7.4(4H, m) |
| 212 | Amorphous | 1.8–2.0(4H, m), 2.0–2.2(2H, m), 3.4–3.5(2H, m), 3.6–3.8(4H, m), 3.85(3H, s), 4.39(2H, t, J=6.9), 6.43(1H, s), 6.65(2H, d, J=8.9), 6.85(1H, dd, J=8.9, 2.5), 7.08(1H, d, J=2.5), 7.2–7.5(12H, m) |
| 213 | 178–179 | 1.26(6H, d, J=6.9), 2.0–2.2(2H, m), 3.67(2H, t, J=6.2), 3.85(3H, s), 4.2–4.3(1H, m), 4.40(2H, t, J=6.2), 5.86 (1H, d, J=7.9), 6.42(1H, s), 6.63(2H, d, J=8.9), 6.86(1H, dd, J=8.9, 2.5), 7.08(1H, d, J=2.5), 7.2–7.5(9H, m), 7.62(2H, d, J=8.9) |
| 214 | 72–76 | 1.13(6H, d, J=6.9), 2.03(2H, t, J=7.6) 2.20(3H, s), 2.55(3H, s), 3.89(3H, s), 3.96(2H, t, J=7.6), 3.98–4.16 (1H, m), 5.30(1H, br), 6.88(1H, dd, J=8.8, 2.4) 7.02(1H, d, J=2.4), 7.22(1H, d, J=8.8) 7.28(2H, d, J=8.4), 7.35(2H, d, J=8.4) |
| 215 | 82–85 | 1.14(6H, d, J=6.9), 1.05–1.67 (18H, m), 2.11(2H, J=7.6), 2.20(3H, s), 2.55(3H, s), 3.89(3H, s), 3.96(2H, t, J=7.5), 4.0–4.17(1H, m), 5.22(1H, br), 6.88(1H, dd, J=8.7, 2.4), 7.02 (1H, d, J=2.4), 7.23(1H, d, J=8.7), 7.28(2H, d, J=8.4), 7.35(2H, d, J=8.4) |
| 216 | 88–90 | 1.04–1.68(16H, m), 1.13(6H, d, J=6.9) 2.10(2H, t, J=7.6), 2.20(3H, s), 2.55(3H, s), 3.89(3H, s), 3.96 (2H, t, J=7.6), 4.12–4.28(1H, m), 5.48(1H, br), 6.88(1H, dd, J=8.8, 2.4), 7.02 (1H, d, J=2.4), 7.23(1H, d, J=8.8), 7.28(2H, d, J=8.3), 7.35(2H, d, J=8.3) |
| 217 | 103–104 | 0.96–1.92(22H, m), 2.10(2H, t, J=7.6) 2.20(3H, s), 2.55(3H, s), 3.89(3H, s), 3.96(2H, t, J=7.6), 4.30–4.47(1H, m), 5.58(1H, br), 6.89(1H, dd, J=8.9, 2.3) 7.02(1H, d, J=2.3), 7.23(1H, d, J=8.9) 7.28(2H, d, J=8.2), 7.35(2H, d, J=8.2) |
| 218 | 84–86 | 0.97–1.91(24H, m), 2.10(2H, t, J=7.5) 2.20(3H, s), 2.55(3H, s), 3.89(3H, s), 3.96(2H, t, J=7.4), 4.3–4.47(1H, m), 5.54(1H, br), 6.88(1H, dd, J=8.8, 2.4) 7.02(1H, d, J=2.4), 7.23(1H, d, J=8.8) 7.28(2H, d, J=8.6), 7.35(2H, d, J=8.6) |
| 219 | Oil | 1.02–1.67(10H, m), 2.20(3H, s), 2.23 (2H, t, J=7.4), 2.55(3H, s), 2.97. 2.92(total 6H, each s), 3.89(3H, s), 3.96 (2H, t, J=7.5), 6.88(1H, dd, J =8.7, 2.5), 7.02(1H, d, J=2.5), 7.22(1H, d, J=8.7), 7.28(2H, d, J=8.7), 7.35(2H, d, J=8.7) |
| 220 | 110–111 | 0.98–1.93(16H, m), 2.02(2H, t, J=7.7) 2.20(3H, s), 2.56(3H, s), 3.89(3H, s), 3.96(2H, t, J=7.4), 5.58(1H, br), 6.68(1H, dd, J=8.6, 2.3), 7.02(1H, d, J=2.3), 7.22(1H, d, J=8.6), 7.28(2H, d, J=8.2), 7.35(2H, d, J=8.2) |
| 221 | Oil | 1.01–1.63(10H, m), 1.33(9H, s), 2.00 (2H, t, J=7.6), 2.20(3H, s), 2.56(3H, s), 3.89(3H, s), 3.96(2H, J=7.6), 5.21(1H, br), 6.89(1H, dd, J=8.9, 2.3) 7.02(1H, d, J=2.3), 7.22(1H, d, J=8.9) 7.28(2H, d, J=8.2), 7.35(2H, d, J=8.2) |
| 222 | Oil | 1.04–1.68(14H, m), 2.20(3H, s), 2.24 (2H, t, J=7.6), 2.55(3H, s), 3.35(2H, t, J=5.3), 3.52(2H, t, J=5.3), 3.89 |

TABLE 16-continued

| No. | mp (°C.) | ¹H-NMR(CDCl₃) |
|---|---|---|
| | | (3H, s), 3.96(2H, t, J=7.6), 6.88(1H, dd, J=8.8, 2.5), 7.01(1H, d, J=2.5), 7.22(1H, d, J=8.8), 7.28(2H, d, J=8.9) 7.35(2H, d, J=8.9) |
| 223 | 104~105 | 1.02–1.72(11H, m), 1.13(6H, d, J=6.9) 1.38(3H, t, J=7.4), 2.04(2H, t, J=7.6), 3.02(2H, q, J=7.3), 3.86(3H, s), 4.09(2H, t, J=7.6), 5.14–5.30 (1H, br), 6.42(1H, s), 6.88(1H, dd, J=8.8, 2.4), 7.08(1H, d, J=2.4), 7.25 (1H, d, J=8.8), 7.38(4H, s) |
| 224 | Oil | 1.37(3H, t, J=7.4), 1.76–2.18(6H, m), 2.99(2H, q, J=7.4), 3.47(2H, t, J=6.7) 3.63(2H, t, J=6.7), 3.70(2H, t, J=5.8) 3.86(3H, s), 4.39(2H, t, J=5.8), 6.43 (1H, s), 6.66(2H, d, J=8.9), 6.85(1H, dd, J=8.7, 2.4), 7.08(1H, d, J=2.4), 7.26–7.35(5H, m), 7.45(2H, d, J=8.9) |
| 225 | 127~130 | 1.27(6H, d, J=6.9), 1.36(3H, t, J=7.4) 2.04–2.17(2H, m), 2.96(2H, q, J=7.4) 3.67(2H, t, J=5.7), 3.86(3H, s), 4.15–4.34(1H, m), 4.41(2H, t, J=6.7) 5.90(1H, d, J=6.9), 6.42(1H, s), 6.63 (2H, d, J=8.9), 6.86(1H, dd, J=8.9, 2.5), 7.08(1H, d, J=2.5), 7.20–7.31 (5H, m), 7.63(2H, d, J=8.7) |
| 226 | Oil | 1.80–2.00(4H, m), 2.50(3H, s), 3.40 (2H, t, J=6.7), 3.63(2H, t, J=6.7), 3.86(3H, s), 5.29(2H, s), 6.57(1H, s) 6.81(1H, dd, J=8.9, 2.4), 7.03(1H, d, J=8.9), 7.04(2H, d, J=8.4), 7.13(1H, d, J=2.4), 7.24(2H, d, J=8.4), 7.31 (2H, d, J=8.4), 7.44(2H, d, J=8.4) |
| 227 | Oil | 1.35(3H, t, J=7.4), 1.78–2.02(4H, m) 2.97(2H, q, J=7.5), 3.40(2H, t, J=6.4), 3.63(2H, t, J=6.4), 3.86(3H, s) 5.33(2H, s), 6.57(1H, s), 6.81(1H, dd, J=8.9, 2.5), 7.04(2H, d, J=8.4), 7.13(1H, d, J=2.5), 7.30(4H, s), 7.44 (2H, d, J=8.4) |
| 228 | 112~115 | 1.09(6H, d, J=6.4), 1.05–1.20(2H, m) 1.42–1.71(4H, m), 1.97(2H, t, J=7.3) 3.85(3H, s), 3.95–4.10(1H, m), 4.10 (2H, t, J=7.3), 5.19(2H, brs), 6.42 (1H, s), 6.87(1H, dd, J=2.4, 8.7), 7.07(1H, d, J=2.4), 7.28–7.53(10H, m) |
| 229 | | 2.27(3H, s), 2.50(3H, s), 3.69(3H, s), 3.88(3H, s), 5.15(2H, s), 6.55–7.30 (11H, m) |
| 230 | 108~110 | 2.26(3H, s), 2.49(3H, s) 3.73(3H, s) 3.87(3H, s), 5.11(2H, s), 6.70–7.28 (11H, m) |
| 231 | 94~96 | 1.05–1.20(2H, m), 1.40–1.60(4H, m), 2.11–2.20(2H, m), 2.55(3H, s), 2.95 (1H, t, J=6.4), 3.03(1H, t, J=6.3), 3.59(1H, t, J=6.3), 3.79(1H, t, J=6.4), 3.88(3H, s), 3.99(2H, t, J=7.3) 4.34(1H, s), 4.54(1H, s), 6.88(1H, dd, J=2.3, 8.7), 7.02(1H, d, J=2.3), 7.22(1H, d, J=8.7), 7.27(2H, d, J=8.2), 7.34(2H, d, J=8.3) |

TABLE 17

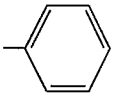

| Example | R³ | R⁶ | R⁷ | m | A | R⁵ | salt |
|---|---|---|---|---|---|---|---|
| 234 | H | 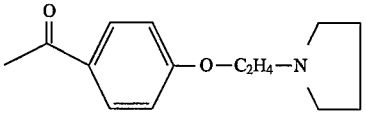 | H | 0 | — | 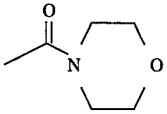 | — |
| 235 | —CH₃ | —CH₃ | H | 1 | —(CH₂)₇— | 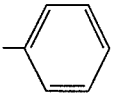 | — |
| 236 | H | 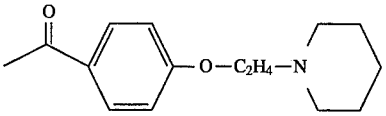 | H | 0 | — | 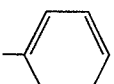 | — |
| 237 | H | 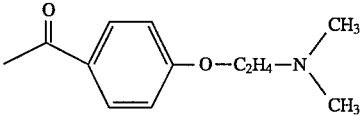 | H | 0 | — | 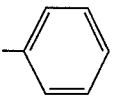 | — |
| 238 | H | 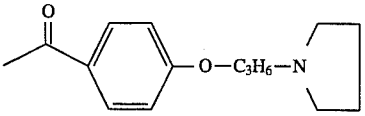 | H | 0 | — | | — |

TABLE 17-continued

Structure: 5-hydroxyindole with R³ at position 3, substituted phenyl at position 2 bearing R⁷ and S—R⁶, and N-(A)n—R⁵

| Example | R³ | R⁶ | R⁷ | m | A | R⁵ | salt |
|---|---|---|---|---|---|---|---|
| 239 | H | phenyl | H | 0 | — | —C(O)—C₆H₄—O—C₃H₆—N(piperidine) | HCl |
| 240 | H | —C₂H₅ | H | 0 | — | —C(O)—C₆H₄—OH | — |
| 241 | H | phenyl | H | 0 | — | —C(O)—C₆H₄—O—C₄H₈—N(imidazole) | — |
| 242 | H | phenyl | H | 1 | —(CH₂)₃— | —O—C₆H₄—C(O)—N(pyrrolidine) | — |
| 243 | H | phenyl | H | 1 | —(CH₂)₃— | —O—C₆H₄—C(O)—NH—CH(CH₃)₂ | — |
| 244 | H | phenyl | H | 0 | — | —C(O)—C₆H₄—O—C₂H₄—N(imidazole) | — |
| 245 | H | phenyl | H | 0 | — | —C(O)—C₆H₄—O—C₃H₆—N(imidazole) | — |
| 246 | H | phenyl | H | 0 | — | —C(O)—C₆H₄—O—C₄H₈—N(triazole) | — |
| 247 | —CH₃ | phenyl | H | 0 | — | —C(O)—C₆H₄—O—C₂H₄—N(imidazole) | — |
| 248 | —CH₃ | —CH₃ | H | 1 | —(CH₂)₇— | —C(O)—NH—CH(CH₃)₂ | — |
| 249 | —CH₃ | —CH₃ | H | 1 | —(CH₂)₁₀— | —C(O)—NH—CH(CH₃)₂ | — |

TABLE 17-continued

| Example | R³ | R⁶ | R⁷ | m | A | R⁵ | salt |
|---|---|---|---|---|---|---|---|
| 250 | —CH₃ | —CH₃ | H | 1 | —(CH₂)₁₁— | —C(O)NH—CH(CH₃)₂ | — |
| 251 | —CH₃ | —CH₃ | H | 1 | —(CH₂)₁₀— | —C(O)NH-cyclobutyl | — |
| 252 | —CH₃ | —CH₃ | H | 1 | —(CH₂)₁₁— | —C(O)NH-cyclobutyl | — |
| 253 | —CH₃ | —CH₃ | H | 1 | —(CH₂)₇— | —C(O)N(CH₃)₂ | — |
| 254 | —CH₃ | —CH₃ | H | 1 | —(CH₂)₇— | —C(O)NH-cyclobutyl | — |
| 255 | —CH₃ | —CH₃ | H | 1 | —(CH₂)₇— | —C(O)NH—C(CH₃)₃ | — |
| 256 | —CH₃ | —CH₃ | —CH(CH₃)₂ | 1 | —(CH₂)₇— | —C(O)-pyrrolidinyl | — |
| 257 | —CH₃ | —CH₃ | —CH(CH₃)₂ | 1 | —(CH₂)₇— | —C(O)NH—CH(CH₃)₂ | — |
| 258 | —CH₃ | —CH₃ | H | 1 | —(CH₂)₇— | —C(O)-piperidinyl | — |
| 259 | H | —C₂H₅ | H | 1 | —(CH₂)₃— | —O—C₆H₄—C(O)-pyrrolidinyl | — |
| 260 | H | —C₂H₅ | H | 1 | —(CH₂)₃— | —O—C₆H₄—C(O)NH—CH(CH₃)₂ | — |
| 261 | H | —C₂H₅ | H | 1 | —CH₂— | —C₆H₄—C(O)-pyrrolidinyl | — |

TABLE 17-continued

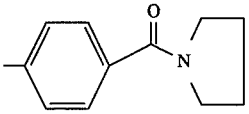

| Example | R³ | R⁶ | R⁷ | m | A | R⁵ | salt |
|---|---|---|---|---|---|---|---|
| 262 | H | —CH₃ | H | 1 | —CH₂— | 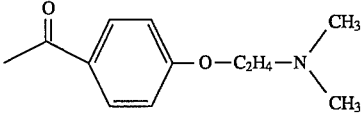 4-C(=O)N(pyrrolidinyl)phenyl | — |
| 263 | —CH₃ | —CH₃ | H | 0 | — | 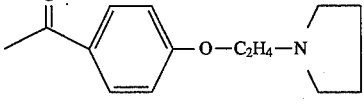 4-acetyl-phenyl-O—C₂H₄—N(CH₃)₂ | — |
| 264 | —CH₃ | —CH₃ | H | 0 | — | 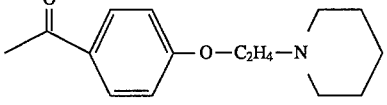 4-acetyl-phenyl-O—C₂H₄—N(pyrrolidinyl) | HCl |
| 265 | —CH₃ | —CH₃ | H | 0 | — | 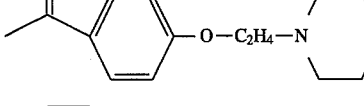 4-acetyl-phenyl-O—C₂H₄—N(piperidinyl) | — |
| 266 | —CH₃ | C₂H₅ | H | 0 | — | 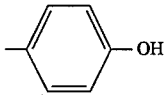 4-acetyl-phenyl-O—C₂H₄—N(piperidinyl) | — |
| 267 | —CH₃ | —CH₃ | H | 1 | —CH₂— | 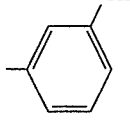 4-hydroxyphenyl | — |
| 268 | —CH₃ | —CH₃ | H | 1 | —CH₂— | 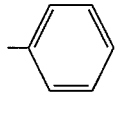 3-hydroxyphenyl | — |
| 269 | H | —C₆H₅ | H | 1 | —(CH₂)₅— | 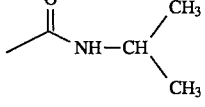 —C(=O)NH—CH(CH₃)₂ | — |
| 270 | —CH₃ | —CH₃ | H | 1 | —(CH₂)₅— | 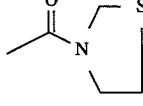 —C(=O)N(thiomorpholinyl) | — |
| 271 | H | —C₂H₅ | H | 1 | —(CH₂)₇— | 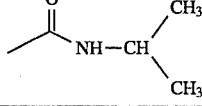 —C(=O)NH—CH(CH₃)₂ | — |

TABLE 18

| No. | mp (°C.) | ¹H-NMR |
|---|---|---|
| 234 | 153~154 | 1.7–1.9(4H, m), 2.6–2.8(4H, m), 2.95 (2H, t, J=5.7), 4.11(2H, t. J=5.7), 6.56(1H, s), 6.67(2H, d, J=8.8), 6.71 (1H, dd, J=8.9, 2.4), 6.95(1H, d, J= 2.4), 7.1–7.4(9H, m), 7.44(1H, d, J= 8.9), 7.51(2H, d, J=8.8) [CDCl₃] |
| 235 | 148~149 | 1.0–1.3(6H, m), 1.4–1.6(4H, m), 2.15 (3H, s), 2.2–2.3(2H, m), 2.54(3H, s), 3.4–3.5(2H, m), 3.6–3.7(6H, m), 3.92 (2H, t, J=7.6), 5.55(1H, brs), 6.79 (1H, dd, J=8.6, 2.3), 6.98(1H, d, J= 2.3), 7.15(1H, d, J=8.6), 7.25(2H, d, J=8.6), 7.33(2H, d, J=8.6) |
| 236 | 125~127 | 1.4–1.5(2H, m), 1.5–1.8(4H, m), 2.5–2.7(4H, m), 2.78(2H, t, J=5.9), 4.11 (2H, t, J=5.9), 6.63(1H, s), 6.72(2H, d, J=8.9), 6.75(1H, dd, J=8.9, 2.5), 7.00(1H, d, J=2.5), 7.1–7.4(9H, m), 7.48(1H, d, J=8.9), 7.55(2H, d, J=8.9) [CDCl₃] |
| 237 | 172~174 | 2.37(6H, s), 2.76(2H, t, J=5.4), 4.08 (2H, t, J=5.4), 6.62(1H, s), 6.74(2H, d, J=7.9), 7.0–7.3(11H, m), 7.45(1H, d, J=8.4), 7.55(2H, d, J=7.9) [CDCl₃] |
| 238 | 188~191 | 1.8–2.0(4H, m), 2.0–2.2(2H, m), 2.9–3.7(6H, m), 4.0–4.2(2H, m), 6.72(1H, dd, J=8.9, 2.0), 6.86(1H, s), 6.95(2H, d, J=8.9), 7.00(1H, d, J=2.0), 7.2–7.4(10H, m), 7.59(2H, d, J=8.9), 9.30 (1H, s), [DMSO-d₆] |
| 239 | 108~110 | 1.3–1.5(2H, m), 1.8–2.0(4H, m), 2.1–2.3(2H, m), 2.3–2.5(2H, m), 2.6–2.8 (2H, m), 3.4–3.6(2H, m), 4.0–4.2(2H, m), 6.66(1H, s), 6.75(2H, d, J=8.2), 6.79(1H, dd, J=8.9, 2.3), 7.04(1H, d, J=2.3), 7.1–7.4(9H, m), 7.43(1H, d, J=8.9), 7.57(2H, d, J=8.2) [DMSO-d₆] |
| 240 | 82~90 | 1.25(3H, t, J=7.4), 2.88(2H, q, J=7.4) 6.64(1H, s), 6.70(2H, d, J=8.9), 6.75 (1H, dd, J=8.7, 2.5), 7.01(1H, d, J= 2.5), 7.15(2H, d, J=8.4), 7.22(2H, d, J=8.4), 7.37(1H, d, J=8.7), 7.55(2H, d, J=8.9), s), [DMSO-d₆] |
| 241 | 145~152 | 1.7–1.8(2H, m), 1.9–2.0(2H, m), 3.9–4.0(4H, m), 6.64(1H, s), 6.73(2H, d, J=8.9), 6.81(1H, dd, J=8.9, 2.5), 7.05(1H, d, J=2.5), 7.1–7.3(9H, m), 7.44(1H, d, J=8.9), 7.58 (2H, d, J=8.9) [CDCl₃] |
| 242 | 148~151 | 1.8–2.0(4H, m), 2.0–2.1(2H, m), 3.4–3.5(2H, m), 3.6–3.8(4H, m), 4.36(2H, t, J=6.7), 5.78(1H, brs), 5.36(1H, s) 6.62(2H, d, J=8.9), 6.73(1H, dd, J = 8.4, 2.3), 7.01(1H, d, J=2.3), 7.1–7.5(12H, m) [CDCl₃] |
| 243 | 147~151 | 1.26(6H, d, J=6.4), 2.0–2.2(2H, m), 3.5–3.6(2H, m), 4.2–4.5(3H, m), 5.29 (1H, brs), 5.9(1H, d, J=7.9), 6.36 (1H, s), 6.62(2H, d, J=8.4), 6.77(1H, dd, J=8.4, 1.9), 7.03(1H, d, J=1.9), 7.1–7.5(10H, m), 7.62(2H, d, J=8.4) [CDCl₃] |
| 244 | 199~202 | 4.3–4.4(4H, m), 6.70(1H, dd, J=8.9, 2.5), 6.85(1H, s), 6.94(2H, d, J=8.7) 6.98(2H, d, J=2.5), 7.2–7.4(12H, m), 7.57(2H, d, J=8.7), 7.68(1H, d, J=8.7), 9.26 (1H, s) [DMSO-d₆] |
| 245 | 197~200 | 2.1–2.2(2H, m), 3.95(2H, t, J=6.6), 4.12(2H, t, J=6.6), 6.72(1H, dd, J= 8.9, 2.5), 6.85(1H, s), 6.92(2H, d, J= 8.9), 6.99(1H, d, J=2.5), 7.1–7.4 (12H, m), 7.54(1H, s), 7.59(2H, d, J= 8.9), 9.26 (1H, s) [DMSO-d₆] |
| 246 | 179~182 | 4.39(2H, d, J=5.0), 4.60(2H, d, J=5.0) 6.70(1H, dd, J=8.9, 2.5), 6.85(1H, s), 6.93(2H, d, J=8.9), 6.98(1H, d, J=2.5) 7.2–7.4(10H, m), 7.56(2H, d, J=8.9), 7.98(1H, s), 8.57(1H, s), 9.25(1H, s) [DMSO-d₆] |
| 247 | 195~196 | 2.50(3H, s), 4.2–4.4(4H, m), 6.73 (1H, dd, J=8.7, 2.3), 6.91(2H, d, J= 8.7), 6.94(1H, d, J=2.3), 7.1–7.5 (9H, m), 7.51(1H, d, J=8.7), 7.70(2H, d, J=8.7), 9.27(1H, s) [DMSO-d₆] |
| 248 | 145~148 | 0.98–1.62(10H, m), 1.13(6H, d, J=6.9) 2.04(2H, t, J=7.6), 2.17(3H, s), 2.54(3H, s), 3.95(2H, t, J=7.6), 3.92–4.10(1H, m), 6.81(1H, dd, J= 8.7, 2.3), 6.97(1H, d, J=2.3), 7.17 (1H, d, J=8.7), 7.23(2H, d, J=8.3), 7.34(2H, d, J=8.3) [CDCl₃+CD₃OD] |
| 249 | 85~86 | 0.94–1.67(16H, m), 1.15(6H, d, J=6.9) 2.12(2H, t, J=7.6), 2.16(3H, s), 2.54 (3H, s), 3.95(2H, t, J=7.3), 4.03–4.20(1H, m), 5.34(1H, br), 5.98(1H, br), 6.83(1H, dd, J=8.7, 2.4), 7.00 (1H, d, J=2.4), 7.17(1H, d, J=8.7), 7.27(2H, d, J=8.6), 7.33(2H, d, J=8.6) [CDCl₃] |
| 250 | Amorphous | 0.95–1.70(18H, m), 1.14(3H, s), 1.16 (3H, s), 2.14(2H, t, J=7.4) 2.15(3H, s), 2.54(3H, s), 3.94(2H, t, J=7.4), 4.04–4.20(1H, m), 5.43(1H, br), 6.45 (1H, s), 6.84(1H, dd, J=8.6, 2.3), 7.01(1H, d, J=2.3), 7.16(1H, d, J=8.6) 7.27(2H, d, J=8.4), 7.33(2H, d, J=8.4) [CDCl₃] |
| 251 | Oil | 0.95–1.92(22H, m), 2.11(2H, t, J=7.7) 2.16(3H, s), 2.55(3H, s), 3.96(2H, t, J=7.3), 4.35–4.50(1H, m), 5.57(1H, s) 5.62(1H, br), 6.82(1H, dd, J=8.7, 2.4) 6.99(1H, d, J=2.4), 7.18(1H, d, J=8.7) 7.29(2H, d, J=8.7), 7.34(2H, d, J=8.7) [CDCl₃] |
| 252 | Oil | 0.97–1.92(24H, m), 2.13(2H, t, J=7.7) 2.16(3H, s), 2.55(3H, s), 3.95(2H, t, J=7.3), 4.35–4.50(1H, m), 5.69(1H, br), 5.92(1H, brs), 6.83(1H, dd, J= 8.6, 2.4), 7.00(1H, d, J=2.4), 7.17 (1H, d, J=8.6), 7.28(2H, d, J=8.5), 7.34(2H, d, J=8.5), [CDCl₃] |
| 253 | 107~109 | 0.94–1.63(10H, m), 2.15(3H, s), 2.25 (2H, t, J=7.6), 2.54(3H, s), 2.95, 2.98,(total 6H, each s), 3.90(2H, t, J=7.4), 6.10(1H, s), 6.82(1H, dd, J=8.6, 2.4) 7.00(1H, d, J=2.4), 7.14(1H, d, J=8.6) 7.24(2H, d, J=8.2), 7.32(2H, d, J=8.2) [CDCl₃] |
| 254 | 144~146 | 0.97–1.93(16H, m), 2.03(2H, t, J=7.6) 2.16(3H, s), 2.55(3H, s), 3.94(2H, t, J=7.3), 4.25–4.40(1H, m), 6.81(1H, dd, J=8.7, 2.3), 6.98(1H, d, J=2.3), 7.16(1H, d, J=8.7), 7.28(2H, d, J=8.4) 7.35(2H, d, J=8.4) [CDCl₃+CD₃OD] |
| 255 | 175~178 | 1.00–1.62(10H, m), 1.32(9H, s), 2.01 (2H, t, J=7.6), 2.16(3H, s), 2.56(3H, s), 3.95(2H, t, 9=7.6), 6.80(1H, dd, J=8.7, 2.3), 6.97(1H, d, J=2.3), 7.16 (1H, d, J=8.7), 7.28(2H, d, J=8.2), 7.35(2H, d, J=8.2) [CDCl₃+CD₃OD] |
| 256 | Amorphous | 1.02–2.00(14H, m), 1.25(3H, s), 1.28 (3H, s), 2.17(3H, s), 2.20(2H, t, J= 7.6), 2.52(3H, s), 3.33–3.52(4H, m), 3.92(2H, t, J=7.6), 6.81(1H, dd, J= 8.7, 2.4), 7.00(1H, d, J=2.4), 7.16 (1H, d, J=8.7), 7.22–7.27(3H, m) [CDCl₃] |
| 257 | Amorphous | 1.02–1.66(10H, m), 1.14(6H, d, J=6.9) 1.27(6H, d, J=6.9), 2.04(2H, t, J=7.6) 2.17(3H, s), 2.53(3H, s), 3.35–3.49 (1H, m), 3.94(2H, t, J=7.5), 3.99–4.16(1H, m), 5.28(1H, br), 6.80(1H, dd, J=8.7, 2.4), 6.99(1H, d, J=2.4), |

TABLE 18-continued

| No. | mp (°C.) | $^1$H-NMR |
|---|---|---|
| 258 | Amorphous | 7.16–7.28(4H, m) [CDCl$_3$] 0.97–1.70(16H, m), 2.15(3H, s), 2.26 (2H, t, J=7.7), 2.54(3H, s), 3.33– 3.57(4H, m), 3.90(2H, t, J=7.4), 6.03 (1H, brs), 6.81(1H, dd, J=8.6, 2.4), 7.00(1H, d, J=2.4), 7.14(1H, d, J=8.6) 7.24(2H, d, J=8.4), 7.32(2H, d, J=8.4) [CDCl$_3$] |
| 259 | 72–75 | 1.35(3H, t, J=7.3), 1.76–2.11(5H, m), 2.97(2H, t, J=7.3), 3.37–3.73(6H, m), 4.36(2H, t, J=6.6), 6.29(1H, s), 6.34 (1H, s), 6.63(2H, d, J=2.3), 6.75(1H, dd, J=8.7, 2.3), 7.01(1H, d, J=2.3), 7.19(1H, d, J=8.7), 7.26(2H, d, J=8.3) 7.31(2H, d, J=8.3), 7.45(2H, d, J=8.6) [CDCl$_3$] |
| 260 | 75–77 | 1.27(6H, d, J=6.9), 1.35(2H, t, J= 7.3), 2.07(2H, t, J'6.10), 2.95(2H, q, J=7.3), 3.63(2H, t, J=5.6), 4.2–4.4 (1H, m), 4.38(2H, t, J=6.4), 5.80(1H, s), 5.99(1H, d, J=7.7), 6.34(1H, s), 6.60(2H, d, J=8.7), 6.79(1H, dd, J= 8.7, 2.3), 7.04(1H, d, J=2.3), 7.18– 7.29(5H, m), 7.63(2H, d, J=8.7) [CDCl$_3$] |
| 261 | 195–198 | 1.34(3H, t, J=7.4), 1.9–2.11(4H, m), 2.98(2H, q, J=7.4), 3.4–3.73(4H, m), 5.32(2H, s), 6.50(1H, s), 6.73(1H, dd, J=8.7, 2.3), 6.97(1H, d, J=8.7), 6.98(1H, d, J=2.3), 7.05(2H, d, J=8.4) 7.30(4H, s), 7.42(2H, d, J=8.4) [CDCl$_3$+CD$_3$OD] |
| 262 | 225–229 | 1.82–2.03(4H, m), 2.50(3H, s), 3.30– 3.63(4H, m), 5.32(2H, s), 6.50(1H, s) 6.72(1H, dd, J=8.9, 2.4), 6.97(1H, d, J=8.9), 7.05(2H, d, J=8.3), 7.05(1H, d, J=2.4), 7.24(2H, d, J=8.4), 7.32 (2H, d, J=8.4), 7.42(2H, d, J=8.3) [CDCl$_3$+CD$_3$OD] |
| 263 | 140–142 | 2.16(3H, s), 2.402, 2.408(total 9H, each s) 2.79(2H, t, J=34.8), 4.08(2H, t, J=4.8) 6.67(2H, d, J=8.9), 6.72(1H, dd, J= 8.7, 2.3), 6.94(1H, d, J=2.3), 7.087, 7.081(total 4H, each s), 7.31(1H, d, J=8.4) 7.50(2H, d, J=8.9) [CDCl$_3$] |
| 264 | 221–224 | 1.80–2.10(4H, m), 2.18(3H, s), 2.44 (3H, s), 2.86–3.20(2H, m), 3.45–3.70 (4H, m), 4.33–4.47(2H, m), 6.70(1H, dd, J=8.9, 2.5), 6.94(1H, d, J=2.5), 6.99(2H, d, J=8.9), 7.09(1H, d, J=8.9) 7.177, 7.181(total 4H, each s), 7.61(2H, d, J=8.9), 9.30(1H, s), 10.78(1H, br) |
| 265 | 149–151 | [DMSO-d$_6$] 1.40–155(2H, m), 1.57–1.73(4H, m), 2.42(3H, s), 2.45–2.63(4H, m), 2.80 (2H, t, J=5.8), 4.09(2H, t, J=5.8), 6.62(2H, d, J=8.7), 6.71(1H, dd, J= 8.9, 2.5), 6.92(1H, d, J=2.5), 7.08 (4H, s), 7.36(1H, d, J=8.9), 7.48(2H, d, J=8.7) [CDCl$_3$] |
| 266 | 188–191 | 1.23(3H, t, J=7.4), 1.4–1.56(2H, m), 1.56–1.74(4H, m), 2.14(3H, s), 2.5– 2.65(4H, m), 2.79(2H, t, J=5.8), 2.86 (2H, q, J=7.4), 4.06(2H, t, J=5.8), 6.56(2H, d, J=8.7), 6.74(1H, dd, J= 8.7, 2.5), 6.91(1H, d, J=2.5), 7.06 (2H, d, J=8.3), 7.12(2H, d, J=8.3), 7.42(2H, d, J=8.7), 7.49(1H, d, J=8.7) [CDCl$_3$] |
| 267 | | 2.26(3H, s), 2.50(3H, s), 5.05(2H, s), 5.83(2H, brs), 6.60–7.30(11H, m) [CDCl$_3$] |
| 268 | 155–158 | 2.22(3H, s), 2.49(3H, s), 5.08(2H, s), 5.90(2H, brs), 6.43–6.53(2H, m), 6.63–6.78(2H, m), 6.92–7.13(2H, m), 7.20–7.31(4H, m) [CDCl$_3$] |
| 269 | Amorphous | 1.11(6H, d, J=6.6), 1.05–1.15(2H, m), 1.35–1.67(4H, m), 1.99(2H, t, J=7.3), 4.04(2H, t, J=7.3), 5.20(1H, brs), 5.89(1H, brs), 6.34(1H, s), 6.79(1H, dd, J=2.3, 8.6), 7.02(1H, d, J=2.3), 7.16(1H, d, J=8.6), 7.29–7.48(9H, m) [CDCl$_3$] |
| 270 | 107–109 | 1.10–1.20(2H, m), 1.40–1.60(4H, m), 2.10–2.21(2H, m), 2.15(3H, s), 2.54 (3H, s), 2.97(1H, t, J=6.3), 3.05(1H, t, J=6.1), 3.60(1H, t, J=6.1), 3.82 (1H, t, J=6.3), 3.96(2H, J=7.3), 4.36(1H, s), 4.55(1H, s), 5.50(1H, brs), 6.80(1H, dd, J=2.3, 8.7), 6.98 (1H, d, J=2.3), 7.15(1H, d, J=8.7), 7.25(2H, d, J=8.2), 7.33(2H, d, J=8.2) [CDCl$_3$] |
| 271 | Amorphous | 1.0–1.61(10H, m), 1.13(6H, d, J=6.7), 1.36(3H, t, J=7.4) 2.04(2H, t, J=7.6) 2.55(3H, s), 2.98(2H, q, J=7.4), 3.94 (2H, t, =7.6), 6.52(1H, s), 6.82(1H, dd, J=8.7, 2.3), 6.97(1H, d, J=2.3), 7.18(1H, d, J=8.7), 7.24(2H, d, J=8.3) 7.35(2H, d, J=8.3) [CDCl$_3$] |

TABLE 19

| Example | R$^3$ | R$^6$ | R$^7$ | A | R$^5$ | salt |
|---|---|---|---|---|---|---|
| 272 | —CH$_3$ | —CH$_3$ | H | —(CH$_2$)$_8$— | (morpholine) | — |
| 273 | H | (phenyl) | H | —(CH$_2$)$_3$— | —O—(phenylene)—CH$_2$—N(piperidine) | |

TABLE 19-continued

[Structure: indole with 5-HO, 2-aryl (4-SR⁶, 3-R⁷), 3-R³, N-A-R⁵]

| Example | R³ | R⁶ | R⁷ | A | R⁵ | salt |
|---|---|---|---|---|---|---|
| 274 | —CH₃ | —CH₃ | H | —(CH₂)₈— | —NH—CH(CH₃)₂ | — |
| 275 | —CH₃ | —CH₃ | H | —(CH₂)₁₂— | —NH—CH(CH₃)₂ | — |
| 276 | —CH₃ | —CH₃ | H | —(CH₂)₁₁— | —NH—CH(CH₃)₂ | — |
| 277 | —CH₃ | —CH₃ | H | —(CH₂)₁₁— | —NH—cyclobutyl | — |
| 278 | —CH₃ | —CH₃ | H | —(CH₂)₁₂— | —NH—cyclobutyl | — |
| 279 | —CH₃ | —CH₃ | H | —(CH₂)₈— | —N(CH₃)₂ | — |
| 280 | —CH₃ | —CH₃ | H | —(CH₂)₈— | —NH—cyclobutyl | — |
| 281 | —CH₃ | —CH₃ | H | —(CH₂)₈— | —N(pyrrolidinyl) | — |
| 282 | —CH₃ | —CH₃ | H | —(CH₂)₈— | —NH—C(CH₃)₃ | — |
| 283 | —CH₃ | —CH₃ | —CH(CH₃)₂ | —(CH₂)₈— | —N(pyrrolidinyl) | — |
| 284 | —CH₃ | —CH₃ | —CH(CH₃)₂ | —(CH₂)₈— | —NH—CH(CH₃)₂ | — |
| 285 | —CH₃ | —CH₃ | H | —(CH₂)₈— | —N(piperidinyl) | HCl |
| 286 | H | —C₂H₅ | H | —(CH₂)₈— | —NH—CH(CH₃)₂ | HCl |

TABLE 19-continued

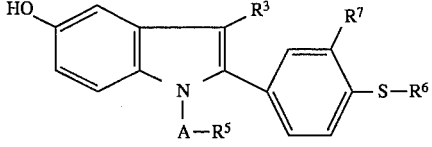

| Example | R³ | R⁶ | R⁷ | A | R⁵ | salt |
|---|---|---|---|---|---|---|
| 287 | H | —C₂H₅ | H | —(CH₂)₃— | 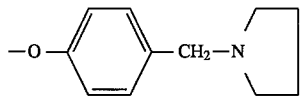 | HCl |
| 288 | H | —C₂H₅ | H | —(CH₂)₃— | 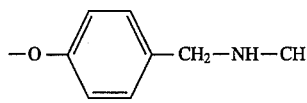 | — |
| 289 | H | —CH₃ | H | —CH₂— | 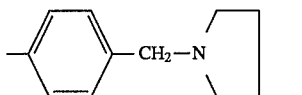 | — |
| 290 | H | —C₂H₅ | H | —CH₂— | 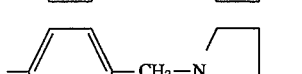 | — |
| 291 | —CH₃ | —CH₃ | H | —(CH₂)₆— | 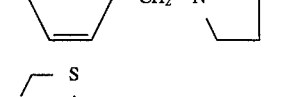 | — |
| 292 | H |  | H | —(CH₂)₆— | 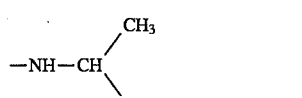 | — |

TABLE 20

| No. | mp (°C.) | ¹H-NMR(CDCl₃) |
|---|---|---|
| 272 | 101~103 | 1.0–1.2(8H, m), 1.4–1.6(4H, m), 2.15 (3H, s), 2.2–2.3(2H, m), 2.4–2.5(4H, m), 2.55(3H, s), 3.74(4H, t, J=4.6), 3.92(2H, t, J=7.6), 6.78(1H, dd, J=8.9, 2.3), 6.95(1H, d,J=2.3), 7.16 (1H, d, J=8.9), 7.25(2H, d, J=8.6), 7.32(2H, d, J=8.6) |
| 273 | 65~68 | 1.7–1.9(4H, m), 1.9–2.2(2H, m), 2.5–2.7(4H, m), 3.5–3.7(4H, m), 4.34(2H, t, J=6.7), 6.36(1H, s), 6.57(1H, d, J=8.9), 6.67(1H, dd, J=8.9, 2.1), 6.95 (1H, d, J=2.1), 7.1–7.5(9H, m) |
| 274 | 96~98 | 0.9–1.60(12H, m), 1.10(6H, d, J=6.9) 2.15(3H, s), 2.54(3H, s), 2.59(2H, t, J=7.4), 2.75–2.93(1H, m), 3.30–3.60(2H, m), 3.89(2H, t, J=7.4), 6.79 (1H, dd, J=8.6, 2.3), 6.95(1H, d, J= 2.3), 7.15(1H, d, J=8.6), 7.22(2H, d, J=8.2), 7.30(2H, d, J=8.2) |
| 275 | Oil | 0.83–1.61(20H, m), 1.14(6H, d, J=6.9) 2.15(3H, s), 2.53(3H, s), 2.65(2H, t, J=7.4), 2.80–2.96(1H, m),3.94(2H, t, J=6.8), 6.8(1H, dd, J=8.7, 2.3), 6.97(1H, d, J=2.3), 7.15(1H, d, J=8.7) 7.27(2H, d, J=8.3), 7.32(2H, d, J=8.3) |
| 276 | Oil | 1.0–1.63(16H, m), 1.14(6H, d, J=6.9) 2.15(3H, s), 2.53(3H, s), 2.64 (2H, t, J=7.4), 2.78–2.94(1H, m), 3.94(2H, t, J=7.3), 4.30(2H, br), 6.79(1H, dd, J=8.7, 2.3), 6.97(1H, d, J=2.3), 7.16(1H, d, J=8.7), 7.27(2H, d, J=8.6), 7.33(2H, d, J=8.6) |
| 277 | Oil | 0.97–1.80(24H, m), 2.16(3H, s), 2.55 (3H, s), 2.55(2H, t, J=7.4), 3.13–3.40(1H, m), 3.96(2H, t, J=7.1), 6.78 (1H, dd, J=8.6, 2.3), 6.97(1H, d, J= 2.3), 7.13(1H, d, J=8.6), 7.28(2H, d, J=8.6), 7.34(2H, d, J=8.6) |
| 278 | Oil | 0.90–1.80(26H, m), 2.17(3H, s), 2.55 (3H, s), 2.55(2H, t, J=7.1), 3.98(2H, t, J=6.9), 6.80(1H, dd, J=8.6, 2.3), 6.96(1H, d, J=2.3), 7.18(1H, d, J=8.6) 7.28(2H, d, J=8.6), 7.34(2H, d, J=8.6) |
| 279 | 75~78 | 0.96–1.60(12H, m), 2.15(3H, s), 2.27 (2H, t, J=7.4), 2.27(6H, s), 2.54(3H, s), 3.88(2H, t, J=7.4), 6.78(1H, dd, J=8.6, 2.4), 6.93(1H, d, J=2.4), 7.14 (1H, d, J=8.6), 7.22(2H, d, J=8.4), 7.30(2H, d, J=8.4), |
| 280 | 88~90 | 0.94–1.80(18H, m), 2.15(3H, s), 2.50 (2H, t, J=7.4), 2.54(3H, s), 3.27(2H, t, J=6.9), 3.90(2H, t, J=7.6), 6.78 (1H, dd, J=8.6, 2.3), 6.95(1H, d, J= 2.3), 7.15(1H, d, J=8.6), 7.23(2H, d, J=8.2), 7.31(2H, d, J=8.2) |
| 281 | 95~97 | 0.92–1.57(12H, m), 1.70–1.86(4H, m) 2.14(3H, s), 2.45(2H, t, J=7.4), 2.50–2.63(4H, m), 2.54(3H, s), 3.87(2H, |

TABLE 20-continued

| No. | mp (°C.) | ¹H-NMR(CDCl₃) |
|---|---|---|
| | | t, J=7.6), 6.78(1H, dd, J=8.7, 2.2), 6.93(1H, d, J=2.2), 7.14(1H, d, J=8.7) 7.21(2H, d, J=8.3), 7.29(2H, d, J=8.3) |
| 282 | 120– 123 | 1.00–1.60(12H, m), 1.14(9H, s), 2.15 (3H, s), 2.54(2H, t, J=7.4), 2.54(3H, s), 2.84(2H, br), 3.90(2H, t, J=7.4), 6.79(1H, dd, J=8.6, 2.3), 6.96(1H, d, J=2.3), 7.15(1H, d, J=8.6), 7.23(2H, d, J=8.4), 7.31(2H, d, J=8.4) |
| 283 | 97– 99 | 1.00–1.88(16H, m), 1.27(6H, d, J=6.9) (3H,s), 2.17(3H, s), 2.40–2.60(6H, m) 2.52(3H, s), 3.34–3.60(1H, m), 3.91 (2H, t, J=7.5), 6.77(1H, dd, J=8.7, 2.4), 6.94(1H, d, J=2.4), 7.11–7.22 (4H, m) [CDCl₃] |
| 284 | Oil | 1.00–1.66(12H, m), 1.07(3H, s), 1.10 (3H, s), 1.26(3H, s), 1.28(3H, s), 2.18(3H, s), 2.52(3H, s), 2.57(2H, t, J=7.3), 2.62–2.95(4H, m), 3.30–3.51 (1H, m), 3.93(2H, t, J=7.4), 6.79(1H, dd, J=8.7, 2.4), 6.97(1H, d, J=2.4), 7.13–7.26(4H, m) [CDCl₃] |
| 285 | 93– 94 | 0.84–1.95(18H, m), 2.16(3H, s), 2.16– 2.78(4H, m), 2.55(3H, s), 3.44–3.56 (2H, m), 3.96(2H, t, J=6.8), 6.98(1H, dd, J=8.7, 2.3), 7.05(1H, d, J=2.3), 7.15(1H, d, J=8.7), 7.26(2H, d, J=8.9) 7.33(2H, d, J=8.9) [CDCl₃] |
| 286 | 115– 118 | 1.00–1.68(12H, m), 1.12(3H, s), 1.15 (3H, s), 1.37(3H, t, J=7.3), 2.05(2H, t, J=7.7), 3.01(2H, q, J=7.3), 4.06 (2H, t, J=7.4), 5.2–5.3(1H, br), 6.37 (1H, s), 6.80(1H, d, d, J=8.9, 2.5), 7.03(1H, d, J=2.5), 7.20(1H, d, J=8.9) 7.37(4H, s) [CDCl₃] |
| 287 | 57– 60 | 1.37(3H, t, J=7.4), 1.93–2.16(6H, m) 2.99(2H, q, J=7.4), 3.40–3.65(4H, m) 4.13(2H, s), 4.37(2H, t, J=6.4), 6.37 (1H, s), 6.67(2H, d, J=8.4), 6.71(1H, dd, J=8.9, 2.3), 7.00(1H, d, J=2.3), 7.19(1H, d, J=8.9), 7.28–7.39(6H, m) [CDCl₃+CD₃OD] |
| 288 | 98– 99 | 1.12(6H, d, J=6.9), 1.39(2H, t, J=7.4), 2.04(2H, t, J=6.2), 3.01(2H, q, J=7.4), 3.71(2H, s), 3.73(2H, t, J= 5.6), 3.9–4.10(1H, m), 6.36(1H, s), 6.68(2H, d, J=8.4), 6.72(1H, dd, J= 8.9, 2.4), 7.01(1H, d, J=2.4), 7.20 (1H, d, J=8.9), 7.27–7.39(6H, m) [CDCl₃+CD₃OD] |
| 289 | 180– 183 | 1.70–1.84(4H, m), 2.40–2.57(7H, m), 3.23–3.42(4H, m), 3.57(2H, s), 5.28 (2H, s), 6.48(1H, s), 6.71(1H, dd, J=8.7, 2.5), 6.96–7.33(10H, m) [CDCl+CD₃OD] |
| 290 | 163– 167 | 1.34(3H, t, J=7.3), 1.70–1.88(4H, m) 2.43–2.58(4H, m), 2.97(2H, q, J=7.3) 3.58(2H, s), 5.29(2H, s), 6.49(1H, s) 6.71(1H, dd, J=8.8, 2.5), 6.98(2H, d, J=8.6), 6.99(1H, d, J=8.8), 7.05(1H, d, J=2.5), 7.23(2H, d, J=8.6), 7.31 (2H, s), 7.32(2H, s) [CDCl₃+CD₃OD] |
| 291 | Amor- phous | 1.01–1.20(4H, m), 1.25–1.60(4H, m), 2.15(3H, s), 2.20(2H, s), 2.27(2H, t, J=7.3), 2.54(3H, s), 2.55–2.64(4H, m), 3.71(1H, brs), 3.93(2H, t, J=7.3) 6.76(1H, dd, J=2.3, 8.7), 6.94(1H, d, J=2.3), 7.15(1H, d, J=8.7), 7.25(2H, d, J=8.3), 7.32(2H, d, J=8.3) [CDCl₃] |
| 292 | 63– 65 | 1.12(6H, d, J=6.4), 1.05–1.25(4H, m) 1.31–1.47(2H, m), 1.53–1.68(2H, m), 2.53(2H, t, J=7.4), 2.73–2.87(1H, m) 3.61(2H, brs, 4.04(2H, t, J=7.4), 6.33(1H, s), 6.76(1H, dd, J=2.4, 8.7) 6.98(1H, d, J=2.4), 7.15(1H, d, J=8.7) 7.30–7.48(10H, m) [CDCl₃] |

Example 293

Production of 5-methoxy-3-methyl-2-(2-thienyl)indole

The procedure of Example 1 was followed using 2-bromo-1-(2-thienyl)-1-propanone and p-anisidine to give the objective compound as crystals (m.p. 113°–115° C.).

¹H-NMR (δ: ppm): [CDCl₃] 2.45 (3H, s), 3.88 (3H, s), 6.85 (1H, dd, J=2.3, 8.6), 7.00 (1H, d, J=2.3) , 7.10–7.18 (1H, m), 7.20–7.27 (2H, m), 7.32 (1H, d, J=5.1), 7.89 (1H, brs)

Example 294

Production of 1-(5-isopropylcarbamoylpentyl)-5-methoxy-3-methyl-2-(2-thienyl)indole The procedure of Example 25 was followed using the compound obtained in Example 293 to give the objective compound as an oil.

¹H-NMR (δ: ppm): [CDCl₃] 1.11 (6H, d, J=6.6), 1.15–1.35 (2H, m), 1.43–1.60 (2H, m), 1.63–1.75 (2H, m), 2.00 (2H, t, J=7.3), 2.27 (3H, s) , 3.88 (3H, s), 4.07 (2H, t, J=7.3), 5.15 (1H, brs), 6.89 (1H, dd, J=2.3, 8.6), 7.01 (1H, d, J=2.3), 7.07 (1H, d, J=3.6), 7.10–7.25 (2H, m), 7.46 (1H, d, J=5.1)

Example 295

Production of 5-hydroxy-1-(5-isopropylcarbamoylpentyl)-3-methyl-2-(2-thienyl)indole The procedure of Example 84 was followed using the compound obtained in Example 294 to give the objective compound as an oil.

¹H-NMR (δ: ppm): [CDCl₃] 1.11 (6H, d, J=6.6), 1.12–1.25 (2H, m), 1.48–1.67 (4H, m), 2.02 (2H, t, J=7.3), 2.21 (3H, s), 4.00 (2H, t, J=7.3), 4.03–4.15 (1H, m), 5.31 (1H, brs), 6.27 (1H, brs), 6.82 (1H, dd, J=2.3, 8.6), 6.99 (1H, d, J=2.3), 7.03 (1H, d, J=2.6), 7.10–7.18 (2H, m), 7.43 (1H, d, J=4.3)

Example 296

Production of 5-hydroxy-1-(6-isopropylaminohexyl)-3 -methyl-2-(2-thienyl)indole

The procedure of example 156 was followed using the compound obtained in Example 295 to give the objective compound as an oil.

¹H-NMR (δ: ppm): [CDCl₃] 1.10 (6H, d, J=6.3), 1.15–1.30 (4H, m), 1.35–1.69 (4H, m), 2.21 (3H, s), 2.57 (2H, t, J=7.3), 2.77–2.89 (1H, m), 3.98 (2H, t, J=7.3), 4.35 (2H, brs), 6.78 (1H, dd, J=2.3, 8.7), 6.93 (1H, d, J=2.3), 7.01 (1H, d, J=1.2), 7.05–7.17 (2H, m), 7.42 (1H, dd, J=1.2, 5.1)

Example 297

Production of 5-methoxy-3-methyl-2-(4-phenylselenylphenyl)indole

A 11.5 g quantity of the compound obtained in Reference Example 12 was dissolved in 20 ml of dimethylacetamide, 16 g of p-anisidine was added, and the mixture was stirred at 130° C. for 1 hour. The mixture was allowed to cool and extracted with ethyl acetate (200 ml× 3 times). The ethyl acetate layers were combined, washed with 4N hydrochloric acid, dried over anhydrous magnesium sulfate and concentrated under reduced pressure. The residue obtained was purified by silica gel chromatography (developing solvent: dichloromethane) to give 7.9 g of the objective compound as crystals (m.p. 95°–96° C.).

¹H-NMR (δ: ppm): [CDCl₃] 2.40 (3H, s), 3.87 (3H, s), 6.85 (1H, dd, J=2.3, 8.3), 7.01 (1H, d, J=2.3), 7.20 (1H, d, J=8.3), 7.23–7.53 (9H, m), 7.85 (1H, brs)

Example 298

Production of 5-methoxy-3-methyl-2-(4-phenylselenylphenyl)-1 -(5-propylcarbamoylpentyl)indole The procedure of Example 25 was followed using the compound obtained in Example 297 to give the objective compound as crystals (m.p. 104°–105° C.).

¹H-NMR (δ: ppm): [CDCl₃] 1.09 (6H, d, J=6.3), 1.05–1.23 (2H, m), 1.40–1.90 (4H, m), 1.96 (2H, t, J=7.3), 2.19 (3H, s), 3.88 (3H, s), 3.98 (2H, t, J=7.3), 3.99–4.10 (1H, m), 5.10 (1H, brs), 6.88 (1H, dd, J-2.3, 8.7), 7.01 (1H, d, J=2.3), 7.21 (1H, d, J=8.7), 7.29–7.61 (9H, m)

Example 299

Production of 1-(5-cyclobutylcarbamoylpentyl)-5-methoxy-3-methyl-2 -(4-phenylselenylphenyl)indole The procedure of Example 25 was followed using the compound obtained in Example 297 to give the objective compound as crystals (m.p. 58°–59° C.).

¹H-NMR (δ: ppm): [CDCl₃] 1.01–1.19 (2H, m), 1.39–1.86 (8H, m), 1.95 (2H, t, J=7.3), 2.20 (3H, s), 2.23–2.36 (2H, m), 3.88 (3H, s), 3.98 (2H, t, J=7.3), 4.25–4.45 (1H, m), 5.48 (1H, brs), 6.88 (1H, dd, J=2.3, 8.7), 7.01 (1H, d, J=2.3), 7.21 (1H, d, J=8.7), 7.29–7.75 (9H, m)

Example 300

Production of 5-hydroxy-1-(5-isopropylcarbamoylpentyl)-3 -methyl-2-(4-phenylselenylphenyl)indole The procedure of Example 234 was followed using the compound obtained in Example 298 to give the objective compound as an oil.

¹H-NMR (δ: ppm): [CDCl₃] 1.10 (6H, d, J=6.6), 1.05–1.21 (2H, m), 1.40–1.59 (4H, m), 1.97 (2H, t, J=7.3), 2.14 (3H, s), 3.92 (2H, t, J=7.3), 4.01–4.15 (1n, m), 5.20 (1H, brs), 5.83 (1H, brs ), 6.79 (1H, dd, J=2.4, 8.7), 6.98 (1H, d, J=2.4), 7.13 (1H, d, J=8.7), 7.23–7.65 (9H, m)

Example 301

Production of 1-(5-cyclobutylcarbamoylpentyl)-5-hydroxy-3-methyl-2-(4-phenylselenylphenyl)indol The procedure of Example 234 was followed using the compound obtained in Example 299 to give the objective compound as an oil.

¹H-NMR (δ: ppm): [CDCl₃] 1.01–1.18 (2H, m), 1.35–1.85 (8H, m), 1.95 (2H, t, J=7.3), 2.13 (3H, s), 2.21–2.37 (2H, m), 3.91 (2H, t, J=7.3), 4.27–4.45 (1H, m) , 5.50 (1H, brs), 6.13 (1H, brs), 6.79 (1H, dd, J=2.3, 8.7), 6.98 (1H, d, J=2.3) , 7.12 (1H, d, J=8.7), 7.20–7.61 (9H, m)

Example 302

Production of 5-hydroxy-1-(6-isopropylaminohexyl)-3 -methyl-2-(4-phenylselenylphenyl)indole The procedure of Example 156 was followed using the compound obtained in Example 300 to give the objective compound as an oil.

¹H-NMR (δ: ppm): [CDCl₃] 1.01–1.20 (4H, m), 1.08 (6H, d, J=6.3), 1.25–1.60 (4H, m), 2.15 (3H, s), 2.51 (2H, t, J=7.3), 2.73–2.88 (1H, m), 3.80 (2H, brs), 3.91 (2H, t, J=7.3), 6.76 (1H, dd, J=2.3, 8.7), 6.95 (1H, d, J=2.3), 7.14 (1H, d, J=8.7), 7.21–7.50 (9H, m)

Example 303

Production of 1-(6-cyclobutylaminohexyl)-5-hydroxy-3 -methyl-2-(4-phenylselenylphenyl)indole The procedure of Example 156 was followed using the compound obtained in Example 301 to give the objective compound as an oil.

¹H-NMR (δ: ppm): [CDCl₃] 1.02–1.75 (10H, m), 1.90–2.01 (4H, m), 2.16 (3H, s), 2.31 (2H, t, J=7.3), 3.01–3.13 (1H, m), 3.95 (2H, t, J=7.3), 4.03 (2H, brs), 6.79 (1H, dd, J=2.4, 8.7), 6.98 (1H, d, J=2.4), 7.16 (1H, d, J=8.7), 7.21–7.50 (9H, m)

Example 304

Production of 1-[3-(2-dimethylaminoethoxy)propyl]-5-methoxy-3-methyl-2 -(4-methylthiophenyl)indole A 1.08 g quantity of 60% Sodium hydride was added to 15 ml of DMF and, with stirring at 0° C., a solution of 5 g of the compound obtained in Example 12 in 10 ml of DMSO was added dropwise. The resultant mixture was stirred at 0° C. for 15 minutes. Then, 11.0 g of 1,3-dibromopropane was added, and the mixture was stirred at room temperature for 3 hours. After completion of the reaction, 10 ml of water was added and the mixture was extracted with ethyl acetate (50 ml×3 times). The organic layers were combined, washed with water (50 ml×3 times), dried over anhydrous magnesium sulfate and concentrated under reduced pressure to give crude 1-(3-bromopropyl)-5 -methoxy-3-methyl-2-(4-methylthiophenyl)indole.

Then, 1.1 g of 60% sodium hydride and 2.6 g of N,N-dimethylethanolamine were added to 15 ml of DMF. Thereto was added dropwise a solution of the compound obtained above in 10 ml of DMF. The mixture was stirred at room temperature for 12 hours. After completion of the reaction, 10 ml of water was added, and the mixture was extracted with ethyl acetate (50 ml×3 times). The organic layers were combined, washed with water (50 ml× 3 times), dried over anhydrous magnesium sulfate and concentrated under reduced pressure. The residue obtained was purified by silica gel column chromatography (developing solvent: chloroform:methanol=10:1) to give 1.0 g of the objective compound as an oil.

¹H-NMR (δ: ppm): [CDCl₃]1.76–1.82 (2H, m), 2.20 (3H, s), 2.23 (6H, s), 2.39 (2H, t, J=5.8), 2.55 (3H, s), 3.18 (2H, t, J=5.8), 3.31 (2H, t, J=5.8), 3.89 (3H, s), 4.12 (2H, t, J=6.9), 6.88 (1H, dd, J=2.3, 8.7), 7.02 (1H, d, J=2.3), 7.30 (2H, d, J=8.4), 7.34 (2H, d, J=8.4)

Example 305

Production of 1-[6-(2-dimethylaminoethoxy)hexyl]-5 -methoxy-3-methyl-2-(4-phenylthiophenyl)indole The procedure of Example 304 was followed using the compound obtained in Example 2 and 1,6-dibromohexane to give the objective compound as an oil.

1H-NMR (δ: ppm): [CDCl₃] 1.05–1.23 (4H, m), 1.39–1.65 (4H, m), 2.20 (3H, s), 2.26 (6H, s), 2.48 (2H, t, J=5.8), 3.32 (2H, t, J=5.8), 3.47 (2H, t, J=5.8), 3.88 (3H, s), 3.97 (2H, t, J=7.2), 6.88 (1H, dd, J=2.3, 8.7), 7.01 (1H, d, J=2.3), 7.21–7.53 (10H, m)

Example 306

Production of 1-[2-(2-hydroxy-2-isopropylaminoethoxy)ethyl]-5-methoxy-3-methyl-2-(4-methylthiophenyl)indole A 5.0 g quantity of the compound obtained in Example 12 was dissolved in 15 ml of DMF, 1.1 g of 60% sodium hydride was added, 4.4 g of 2-bromoethyl acetate was further added, and the mixture was stirred at room temperature for 3 hours. After completion of the reaction, 10 ml of water was added, and the mixture was extracted with ethyl acetate (50 ml×3 times). The organic layers were combined, washed with water (50 ml× 2 times), dried over anhydrous magnesium sulfate and concentrated under reduced pressure to give crude 1-(2-acetoxyethyl)-5-methoxy-3-methyl-2-(4-methylthiophenyl)indole.

The crude product obtained above was dissolved in 15 ml of 1,4-dioxane, a solution of 4.0 g of potassium hydroxide in water (10 ml) was added, and the mixture was stirred at 70° C. for 3 hours. The mixture was allowed to cool and then extracted with diethyl ether. The organic layer was collected, dried over anhydrous magnesium sulfate and concentrated under reduced pressure. The residue obtained was purified by silica gel column chromatography (developing solvent: chloroform:methanol=30:1) to give 3.6 g of 1-(2-hydroxyethyl)-5-methoxy-3-methyl-2-(4-methylthiophenyl)indole as crystals (m.p. 123°–125° C.).

$^1$H-NMR (δ: ppm): [CDCl$_3$] 2.20 (3H, s), 2.54 (3H, s), 3.65–3.79 (3H, m), 3.89 (3H, s), 4.16 (2H, t, J=5.8), 6.89 (1H, dd, J=2.3, 8.7), 7.01 (1H, d, J=2.3), 7.26 (1H, d, J=8.7), 7.28–7.37 (4H, m)

Then, 2.6 g of the crystals obtained above were dissolved in 10 ml of DMF, 420 mg of 60% sodium hydride was added and, after 10 minutes of stirring at room temperature, 3.7 g of epichlorohydrin was added. The resultant mixture was stirred at 60° C. for 4 hours. After completion of the reaction, 10 ml of water was added and the mixture was extracted with ethyl acetate. The organic layers were combined, washed with water, dried over anhydrous magnesium sulfate and concentrated under reduced pressure. The residue obtained was purified by silica gel column chromatography (developing solvent: chloroform:methanol=50:1) to give 2.5 g of 1-[2-(2,3-epoxypropoxy)ethyl]-5-methoxy-3-methyl-2-(4methylthiophenyl)indole as an oil.

$^1$H-NMR (δ: ppm): [CDCl$_3$] 2.19 (3H, s), 2.45 (1H, dd, J-2.6, 4.9), 2.55 (3H, s), 2.69 (1H, dd, J=4.9, 4.9), 2.95–3.02 (1H, m), 3.19 (1H, dd, J=5.6, 11.5), 3.55 (1H, dd, J=2.6, 11.5), 3.58–3.68 (2H, m), 3.89 (3H, s), 4.18 (2H, t, J=6.3), 6.89 (1H, dd, J=2.3, 8.9), 7.01 (1H, d, J=2.3), 7.29 (1H, d, J=8.9), 7.30–7.34 (4H, m)

Then, 2.5 g of the compound obtained above was dissolved in 50 ml of isopropylamine and the solution was heated under reflux for 24 hours. After completion of the reaction, the mixture was concentrated under reduced pressure and the residue was purified by silica gel column chromatography (developing solvent: chloroform:methanol= 5:1) to give 1.8 g of the objective compound as crystals (m.p. 70°–72° C.).

$^1$H-NMR (δ: ppm): [CDCl$_3$] 1.00 (6H, d, J=6.3), 1.85–2.15 (2H, brs), 2.19 (3H, s), 2.55 (3H, s), 2.61–2.75 (1H, m), 3.25 (2H, t, J=4.3), 3.56 (2H, t, J=5.9), 3.56–3.65 (1H, m), 3.88 (3H, s), 4.18 (2H, t, J=5.9), 6.88 (1H, dd, J=2.1, 8.6), 7.00 (1H, d, J=2.1), 7.28–7.35 (5H, m)

Example 307

Production of 1-[3-(2-dimethylaminoethoxy)propyl]-5-hydroxy-3-methyl-2-(4-methylthiophenyl)indole The procedure of Example 234 was followed using the compound obtained in Example 304 to give the objective compound as an oil.

$^1$H-NMR (δ: ppm): [CDCl$_3$] 1.67–1.75 (2H, m), 2.13 (3H, s), 2.30 (6H, s), 2.49 (2H, t, J=5.9), 2.52 (3H, s), 3.14 (2H, t, J=5.9), 3.36 (2H, t, J=5.9), 4.03 (2H, t, J=7.0), 5.90 (1H, brs), 6.76 (1H, dd, J=2.3, 8.7), 6.94 (1H, d, J=2.3), 7.15 (1H, d, J=8.7), 7.23 (2H, d, J=7.9), 7.30 (2H, d, J=7.9)

Example 308

Production of 1-[6-(2-dimethylaminoethoxy)hexyl]-5-hydroxy-3-methyl-2-(4-phenylthiophenyl)indole The procedure of Example 234 was followed using the compound obtained in Example 305 to give the objective compound as an oil.

$^1$H-NMR (δ: ppm): [CDCl$_3$] 1.01–1.23 (4H, m), 1.30–1.59 (4H, m), 2.15 (3H, s), 2.30 (6H, s), 2.55 (2H, t, J=5.8), 3.28 (2H, t,. J=5.8), 3.50 (2H, t, J=5.8), 3.90 (2H, t, J=7.2), 5.80 (1H, brs ), 6.79 (1H, dd, J=2.3, 8.7), 6.95 (1H, d, J=2.3) , 7.13 (1H, d, J=8.7), 7.21–7.50 (9H, m)

Example 309

Production of 5-hydroxy-1-[2-(2-hydroxy-2-isopropylaminoethoxy)ethyl]-3-methyl-2-(4-methylthiophenyl)indole The procedure of Example 234 was followed using the compound obtained in Example 306 to give the objective compound as an oil.

$^1$H-NMR (δ: ppm): [CDCl$_3$] 1.03 (6H, d, J=6.3), 2.15 (3H, s), 2.35–2.53 (3H, m), 2.54 (3H, s), 3.23 (2H, t, J=4.6), 3.53 (2H, t, J=5.8), 3.61–3.70 (1H, m), 4.16 (2H, t, J=5.8), 5.30 (1H, brs), 6.77 (1H, dd, J=2.3, 8.6), 6.96 (1H, d, J=2.3), 7.25–7.36 (5H, m)

Example 310

Production of 5-methoxy-3-methyl-2-(4-methylthiophenyl)-1-[ 5-(1-phenylethyl) carbamoylpentyl]indole The procedure of Example 25 was followed using the compound obtained in Example 12 to give the objective compound as crystals (m.p. 99°–101° C.).

$^1$H-NMR (δ: ppm): [CDCl$_3$] 1.05–1.20 (2H, m), 1.44 (3H, d, J=6.9), 1.47–1.63 (4H, m), 2.00 (2H, t, J=7.4), 2.19 (3H, s), 2.54 (3H, s), 3.88 (3H, s), 3.97 (2H, t, J=7.3), 5.11 (1H, m), 5.51 (1H, brs), 6.87 (1H, dd, J=2.4, 8.7), 7.01 (1H, d, J=2.4), 7.19 (1H, d, J=8.7), 7.21–7.35 (9H, m)

Example 311

Production of 5-hydroxy-3-methyl-2-(4-methylthiophenyl)-1-[5 -(1-phenylethyl)carbamoylpentyl]indole The procedure of Example 234 was followed using the compound obtained in Example 310 to give the objective compound as an oil.

$^1$H-NMR (δ: ppm): [CDCl$_3$] 1.01–1.20 (2H, m), 1.44 (3H, d, J=6.9), 1.46–1.60 (4H, m), 2.03 (2H, t, J=7.5), 2.12 (3H, s), 2.52 (3H, s), 3.90 (2H, t, J=7.3), 5.10 (1H, m), 5.67 (1H, brs), 5.92 (1H, brs), 6.77 (1H, dd, J=2.4, 8.7), 6.97 (1H, d, J=2.4), 7.10 (1H, d, J=8.7), 7.20–7.38 (9H, m)

Example 312

Production of 5-hydroxy-3-methyl-2-(4-methylthiophenyl)-1-[ 6-(1-phenylethyl)aminohexyl]indole The procedure of Example 156 was followed using the compound obtained in Example 311 to give the objective compound as crystals (m.p. 118°–120° C.).

$^1$H-NMR (δ: ppm): [CDCl$_3$] 1.01–1.21 (4H, m), 1.20–1.31 (2H, m), 1.35 (3H, d, J=6.7), 1.45–1.60 (2H, m), 2.14 (3H, s), 2.25–2.50 (2H, m), 2.54 (3H, s), 3.72 (1H, q, J=6.7), 3.88 (2H, t, J=7.3), 6.76 (1H, dd, J=2.5, 8.7), 6.95 (1H, d, J=2.5), 7.13 (1H, d, J=8.7), 7.20–7.40 (9H, m)

Dosage Form Example 1 Preparation of Tablets

Using, as the active ingredient, the compound obtained in Example 281, namely (5-hydroxy-3-methyl-2-(4 -methylthiophenyl)-1-[8-(1-pyrrolidinyl)octyl]indole, tablets (1,000 tablets) each containing 100 mg of said compound were prepared according to the following formulation.

| Ingredient | Quantity (g) |
|---|---|
| Compound of Example 281 | 100 |
| Lactose (Japanese Pharmacopeia) | 33.5 |
| Corn starch (Japanese Pharmacopeia) | 16.5 |
| Carboxymethylcellulose calcium (Japanese Pharmacopeia) | 12.5 |
| Methylcellulose (Japanese Pharmacopeia) | 6.0 |
| Magnesium stearate (Japanese Pharmacopeia) | 1.5 |
| | 170.0 |

Thus, according to the above formulation, the compound of Example 281, lactose, corn starch and carboxymethylcellulose calcium were blended up and the mixture was granulated using an aqueous solution of methylcellulose, and the granules were passed through a 24-mesh sieve and mixed with magnesium stearate, followed by pressing to give tablets.

Dosage Form Example 2 Preparation of Capsules

Using, as the active ingredient, the compound obtained in Example 175, namely 1-(6-cyclobutylaminohexyl)-5-hydroxy-3-methyl-2-(4-methylthiophenyl)indole, hard gelatin capsules (1,000 capsules) each containing 100 mg of said compound were prepared according to the following formulation.

| Ingredient | Quantity (g) |
|---|---|
| Compound of Example 175 | 100 |
| Crystalline cellulose (Japanese Pharmacopeia) | 30 |
| Corn starch (Japanese Pharmacopeia) | 15 |
| Talc (Japanese Pharmacopeia) | 2 |
| Magnesium stearate (Japanese Pharmacopeia) | 1 |
| | 148 |

Thus, according to the above formulation, the ingredients were each finely pulverized and mixed up to give a uniform mixture, which was then filled into gelatin capsules for oral administration with a desired size.

Dosage Form Example 3 Preparation of Granules

Using, as the active ingredient, the compound obtained in Example 174, namely 1-(6-isopropylaminohexyl)-5-hydroxy-3-methyl-2-(4-mthylthiophenyl)indole, granules (1,000 g) containing 500 mg of said compound per gram were prepared according to the following formulation.

| Ingredient | Quantity (g) |
|---|---|
| Compound of Example 174 | 500 |
| Lactose (Japanese Pharmacopeia) | 100 |
| Corn starch (Japanese Pharmacopeia) | 250 |
| Carboxymethylcellulose calcium (Japanese Pharmacopeia) | 40 |
| Crystalline cellulose (Japanese Pharmacopeia) | 100 |
| Hydroxypropylmethylcellulose (Japanese Pharmacopeia) | 10 |
| | 1,000 |

Thus, according to the above formulation, the compound of Example 174, lactose, corn starch, crystal line cellulose and carboxymethylcellulose calcium were blended up and, after addition of an aqueous solution of hydroxypropylcellulose, the mixture was kneaded and granulated using an extrusion granulator and the granules were dried at 50° C. for 2 hours to give the desired granules.

Pharmacological Test Example 1

Test for inhibitory activity against the specific binding of [$^3$H]-moxestrol to the rat uterus cytoplasm estrogen receptor The above activity was measured essentially as described in the literature [J. Biol. Chem., 258 (5), 3173 (1973) and Biochem. Pharmacol., 43 (12), 2511 (1992)].

Thus, the uterus was excised from female SD rats aged 3 to 4 weeks and homogenized in 6 volumes of TETG buffer (10 mM Tris-hydrochloride, 1 mM EDTA, 12 mM thioglycerol and 10% glycerol) and the homogenate was centrifuged to give a cytoplasm fraction. $^3$H-Moxestrol and each test compound were added to this cytoplasm fraction and each mixture was incubated at 4° C. for 16 hours to allow binding to the estrogen receptor in the cytoplasm fraction.

Then, the free form of $^3$H-moxestrol was removed by the DCC method and the bound form of $^3$H-moxestrol was quantitated using a liquid scintillation counter.

Moxestrol was used as a control compound and the relative binding affinity (RBA), which was defined as the $^3$H-moxestrol binding inhibiting effect (IC$_{50}$) ratio, was determined as follows:

$$RBA = \frac{IC_{50} \text{ of moxestrol}}{IC_{50} \text{ of test compound}}$$

The thus-obtained RBA values for the respective test compounds are shown below in Table 21.

From said table, it is evident that the compounds of the invention show very strong antiestrogen activity.

TABLE 21

| Test compound (Example No.) | RBA (%) |
|---|---|
| 161 | 46 |
| 172 | 44 |
| 175 | 60 |
| 176 | 64 |
| 178 | 57 |
| 179 | 60 |
| 181 | 52 |
| 182 | 57 |
| 234 | 50 |
| 236 | 53 |
| 238 | 49 |
| 239 | 73 |
| 246 | 57 |
| 253 | 94 |
| 254 | 78 |
| 255 | 41 |
| 258 | 41 |
| 272 | 48 |
| 274 | 65 |
| 279 | 82 |
| 280 | 116 |
| 281 | 121 |
| 282 | 114 |
| 285 | 93 |
| 286 | 51 |
| 291 | 70 |
| 312 | 42 |

We claim:
1. An indole derivative of the general formula

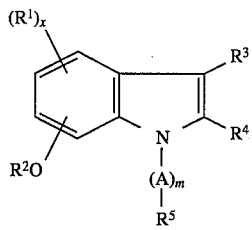

wherein $R^1$ is a halogen atom, $R^2$ is a hydrogen atom, a lower alkyl group, a lower alkanoyl group or a benzoyl group, $R^3$ is a hydrogen atom, a lower alkyl group or a halogen atom, $R^4$ is a group of the formula

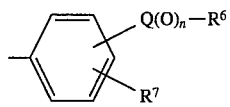

in which $R^6$ is a lower alkyl group, a cycloalkyl group, a phenyl group which may optionally have a lower alkyl group as a substituent, a phenyl-lower alkyl group or a pyridyl group, $R^7$ is a hydrogen atom or a lower alkyl group, Q is a sulfur or selenium atom and n is an integer of 0 to 2, A is an alkylene group, m is an integer of 0 to 1, $R^5$ is a hydrogen atom, an alkyl group or a benzoyl group having a hydroxyl group or a group of the formula $—O—B—R^8$ in which B is a lower alkylene group and $R^8$ is a phenyl, di-lower alkyl-amino, 1-pyrrolidinyl, piperidino, 1-imidazolyl or 1,2,4-triazol-1-yl group as a substituent when m is 0 or, when m is 1, $R^5$ is a lower alkoxycarbonyl group, a carboxyl group, a hydroxyl group, a group of the formula $—C(=O)—N(R^9)—R^{10}$ in which $R^9$ and $R^{10}$ are the same or different and each is a hydrogen atom, a lower alkyl group, a cycloalkyl group which may optionally have a benzene ring fused or condensed thereto, a phenyl group, a phenyl-lower alkyl group or a lower alkylsulfonyl group or $R^9$ and $R^{10}$ are bound to each other either directly or via an oxygen or sulfur atom to form, together with the adjacent nitrogen atom, a heterocyclic group which may optionally be substituted with a lower alkoxycarbonyl or carboxyl group, a group of the formula $—CH_2—N(R^{11})—R^{12}$ in which $R^{11}$ and $R^{12}$ are the same or different and each is a hydrogen atom, a lower alkyl group, a cycloalkyl group which may optionally have a benzene ring condensed thereto, a phenyl group, a phenyl-lower alkyl group or a lower alkanoyl group or $R^{11}$ and $R^{12}$ are bound to each other either directly or via an oxygen or sulfur atom to form, together with the adjacent nitrogen atom, a heterocyclic group which may optionally be substituted with a lower alkoxycarbonyl or carboxyl group, a group of the formula $—OR^{13}$ in which $R^{13}$ is a lower alkylcarbamoylphenyl group, a lower alkylaminomethylphenyl group, a lower alkylaminomethylpenyl group, a 1-pyrrolidinylcarbonylphenyl group, a 1-pyrrolidinylmethylphenyl group, a 2-di-lower alkylaminoethyl group or a 2-hydroxyl-2-lower alkylaminoethyl group or a phenyl group which may optionally have a hydroxyl, lower alkoxy, 1-pyrrolidinylcarbonyl or 1-pyrrolidinylmethyl group as a substituent, and x is an integer of 0 to 2.

2. An indole derivative as claimed in claim 1, wherein $R^2$ is a hydrogen atom, $R^3$ is a hydrogen atom or a lower alkyl group, $R^4$ is a group of the formula

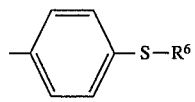

in which $R^6$ is a lower alkyl group, a cycloalkyl group, a phenyl group which may optionally have one or more lower alkyl groups as substituents, a phenyl-lower alkyl group or a pyridyl group and m is 1.

3. An indole derivative as claimed in claim 2, wherein $R^5$ is a group of the formula $—C(=O)—N(R^9)—R^{10}$ in which $R^9$ and $R^{10}$ are the same or different and each is a hydrogen atom, a lower alkyl group, a cycloalkyl group which may optionally have a benzene ring condensed thereto, a phenyl group, a phenyl-lower alkyl group or a lower alkylsulfonyl group or $R^9$ and $R^{10}$ are bound to each other either directly or via an oxygen or sulfur atom to form, together with the adjacent nitrogen atom, a heterocyclic group which may optionally be substituted with a lower alkoxycarbonyl or carboxyl group or a group of the formula $—CH_2—N(R^{11})—R^{12}$ in which $R^{11}$ and $R^{12}$ are the same or different and each is a hydrogen atom, a lower alkyl group, a cycloalkyl group which may optionally have a benzene ring condensed thereto, a phenyl group, a phenyl-lower alkyl group or a lower alkanoyl group or $R^{11}$ and $R^{12}$ are bound to each other either directly or via an oxygen or sulfur atom to form, together with the adjacent nitrogen atom, a heterocyclic group which may optionally be substituted with a lower alkoxycarbonyl or carboxyl group.

4. An indole derivative as claimed in claim 1, said derivative being of the formula

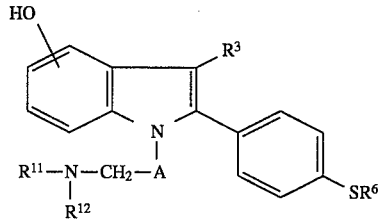

wherein $R^3$ is a hydrogen atom, a lower alkyl group or a halogen atom, $R^6$ is a lower alkyl group, a cycloalkyl group, a phenyl group which may optionally have one or more lower alkyl groups as substituents, a phenyl-lower alkyl group or a pyridyl group, and $R^{11}$ and $R^{12}$ are the same or different and each is a hydrogen atom, a lower alkyl group, a cycloalkyl group which may optionally have a benzene ring condensed thereto, a phenyl group, a phenyl-lower alkyl group or a lower alkanoyl group or R and $R^{12}$ are bound to each other either directly or via an oxygen or sulfur atom to form, together with the adjacent nitrogen atom, a heterocyclic group which may optionally be substituted with a lower alkoxycarbonyl or carboxyl group.

5. An estrogen inhibitor which comprises the indole derivative of claim 1 as an active ingredient.

6. An estrogen inhibitor which comprises the indole derivative of claim 3 as an active ingredient.

7. An estrogen inhibitor which comprises the indole derivative of claim 4 as an active ingredient.

8. A method of treating an estrogen-dependent disease which comprises administering a pharmacologically effective amount of the estrogen inhibitor of claim 5 to the patient.

* * * * *